(12) United States Patent
Stella et al.

(10) Patent No.: US 7,625,878 B2
(45) Date of Patent: Dec. 1, 2009

(54) SULFOALKYL ETHER-ALKYL ETHER CYCLODEXTRIN DERIVATIVES

(75) Inventors: Valentino J. Stella, Lawrence, KS (US); Serena Tongiani, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 513 days.

(21) Appl. No.: 11/413,597

(22) Filed: Apr. 28, 2006

(65) Prior Publication Data

US 2006/0258537 A1    Nov. 16, 2006

Related U.S. Application Data

(63) Continuation of application No. PCT/US2004/036097, filed on Oct. 29, 2004.

(60) Provisional application No. 60/516,022, filed on Oct. 31, 2003.

(51) Int. Cl.
*A61K 31/724* (2006.01)
(52) U.S. Cl. .......................... 514/58; 536/103
(58) Field of Classification Search .................. None
See application file for complete search history.

(56) References Cited

U.S. PATENT DOCUMENTS

| 5,019,562 | A | 5/1991 | Folkman et al. |
| 5,183,809 | A | 2/1993 | Weisz et al. |
| 5,241,059 | A | 8/1993 | Yoshinaga |
| 5,594,125 | A | 1/1997 | Seyschab et al. |
| 5,658,894 | A | 8/1997 | Weisz |
| 5,760,015 | A | 6/1998 | Joullie et al. |
| 5,846,954 | A | 12/1998 | Joullie et al. |
| 6,153,746 | A | 11/2000 | Shah et al. |
| 2002/0128468 | A1 | 9/2002 | Buchanan et al. |

FOREIGN PATENT DOCUMENTS

EP  0146841  4/1984

WO  WO 01/40316  6/2001

OTHER PUBLICATIONS

Szente, L. et al "Highly soluble cyclodextrin derivatives . . . " Adv. Drug Deliv. Rev. (1999) vol. 36, pp. 17-28.*
Ivanyi, R. et al "Permethyl monoamino beta-cyclodextrin . . . " Chromatographia (2001) vol. 53, pp. 166-172.*
Wistuba, D. et al "Enantiomeric separation by capillary electrochromatography . . . " Electrophoresis (2005) vol. 26, pp. 2019-2026.*
Jiczinszky ("Azido function as protecting group . . . ", Inter. Cyclo. Symp., 10th, Ann Arbor, MI, USA, May 21-24, 2000, 46-52; Wacker Biochem, Corp., Adrian, MI.
Tarver et al. ("2-O-substituted cyclodextrins . . . ", Bioorg. Med. Chem. (2002), vol. 10, 1819-1827).
Adam et al. ("Cyclodextrin derived host molecules . . . ", J. Med. Chem. (2002), vol. 45, 1806-1816).
No NPL documents listed.

* cited by examiner

*Primary Examiner*—Leigh C Maier
(74) *Attorney, Agent, or Firm*—Rick Matos; Innovac, L.L.C.

(57) ABSTRACT

A sulfoalkyl ether-alkyl ether cyclodextrin (SAE-AE-CD) derivative is provided. The SAE-AE-CD possesses advantages over known SAE-CD and AE-CD derivatives as well as over the parent cyclodextrin by being more water soluble and less membrane disturbing. The SAE-AE-CD includes at least one sulfoalkyl ether group and at least one alkyl ether group even though the degree of substitution for the functional groups can be different. The SAE functional group can be present in molar excess over the AE functional group and vice versa. The total degree of substitution of the cyclodextrin, with respect to both functional groups, can be varied such that a minority or a majority of the hydroxyl moieties of the CD are derivatized. The SAE-AE-CD derivative can be used to solubilize compounds with insufficient water solubility. In some cases, they also stabilize compounds in solution against degradation or to solubilize degradation products formed during degradation. In addition, SAE-AE-CD can also be used for other purposes such as osmotic agents, agents used to mask the taste of problematic drugs. Surprisingly, while AE-CDs are known to be toxic by being membrane disturbing, SAE-AE-CDs are less membrane disturbing and therefore have greater safety.

41 Claims, 20 Drawing Sheets

HMQC expanded: SBE4.6-Et6.0-β-CD

R= -CH$_2$CH$_2$CH$_2$CH$_2$SO$_3^-$

R= -CH$_2$CH$_3$

R= -H

SULFOALKYL ETHER-ALKYL ETHER CYCLODEXTRIN DERIVATIVES

CROSS-REFERENCE TO EARLIER FILED APPLICATIONS

The present application is a continuation of and claims the priority of PCT International Application No. PCT/US04/036097 filed Oct. 29, 2004, which claims the priority of U.S. Provisional Application No. 60/516,022 filed Oct. 31, 2003, the entire disclosures of which are hereby incorporated by reference.

FIELD OF THE INVENTION

The present invention relates to a water soluble cyclodextrin derivative comprising a mixture of sulfoalkyl ether and alkyl ether substituents on the same cyclodextrin. The invention also provides methods for its preparation and use.

BACKGROUND OF THE INVENTION

Cyclodextrins have been used widely in many different types of cosmetic, food and pharmaceutical formulations. Cyclodextrins are cyclic carbohydrates derived from starch. The unmodified (parent) cyclodextrins differ by the number of glucopyranose units joined together in the cylindrical structure. The parent cyclodextrins contain 6, 7, or 8 glucopyranose units and are referred to as α-, β-, and γ-cyclodextrin, respectively. The underivatized α-cyclodextrin and β-cyclodextrin are the most widely used cyclodextrins. Each cyclodextrin subunit has secondary hydroxyl groups at the 2 and 3 positions and a primary hydroxyl group at the 6-position. The cyclodextrins may be pictured as hollow truncated cones with hydrophilic exterior surfaces and hydrophobic interior cavities. In aqueous solutions, these hydrophobic cavities provide a haven for hydrophobic organic compounds that can fit all or part of their structure into these cavities. This process, known as inclusion complexation, may result in increased apparent aqueous solubility and stability for the complexed compound. The complex is stabilized by hydrophobic interactions and does not involve the formation of any covalent bonds.

This dynamic and reversible equilibrium process can be described by Equations 1 and 2, where the amount in the complexed form is a function of the concentrations of the drug and cyclodextrin, and the equilibrium or binding constant, $K_b$. When cyclodextrin formulations are administered by injection into the blood stream, the complex rapidly dissociates due to the effects of dilution and non-specific binding of the drug to blood and tissue components.

$$\text{Drug} + \text{Cyclodextrin} \overset{K_b}{\leftrightarrow} \text{Complex} \quad \text{Equation 1}$$

$$K_b = \frac{[\text{Complex}]}{[\text{Drug}][\text{Cyclodextrin}]} \quad \text{Equation 2}$$

Binding constants of cyclodextrin and an active agent can be determined by the equilibrium solubility technique as well as other suitable techniques (T. Higuchi et al. in "Advances in Analytical Chemistry and Instrumentation Vol. 4"; C. N. Reilly ed.; John Wiley & Sons, Inc, 1965, pp. 117-212). Generally, the higher the concentration of cyclodextrin, the more the equilibrium process of Equations 1 and 2 is shifted to the formation of more complex, meaning that the concentration of free active agent is generally decreased by increasing the concentration of cyclodextrin in solution.

α-CD and β-CD are known to be unsafe due to severe nephrotoxicity attributed to their damaging of renal epithelial cells. The mechanism of this renal toxicity is not fully understood. The parent CDs also cause red blood cells hemolysis and membrane irritation that appear to be correlated to their capacity to extract lipid membrane components. A good correlation between the ability of CDs to cause red blood cell hemolysys and their renal toxicity has been noted.

Hydrophobic, hydrophilic, polymerized, ionized, non-ionized and many other modifications of cyclodextrins have been developed, and their use in various industries has been established. Chemical modification of the parent cyclodextrins at one or more of the hydroxyl groups has resulted in derivatives with improved properties. Of the numerous derivatized cyclodextrins prepared to date, only two appear to be commercially viable for pharmaceutical usage: the 2-hydroxypropyl derivatives (HP-CD; neutral cyclodextrins being commercially developed by Janssen and others), and the sulfoalkyl ether derivatives (SAE-CD's, such as sulfobutyl ether, (SBE-CD; anionic cyclodextrins being developed by CyDex, Inc.) However, the HP-β-CD still possesses safety issues that the SBE-CD does not.

A number of references disclose water soluble sulfoalkyl ether cyclodextrins and methods for their preparation and use. An SAE-CD can be made according to the disclosures of Stella et al., Parmerter et al., Lammers et al. or Qu et al. (See citations below).

A sulfobutyl ether derivative of beta cyclodextrin (SBE-β-CD), in particular the derivative with an average of about 7 substituents per cyclodextrin molecule, has been commercialized by CyDex, Inc. as CAPTISOL®. The anionic sulfobutyl ether substituent dramatically improves the aqueous solubility and safety of the parent cyclodextrin. Reversible, non-covalent, complexation of drugs with CAPTISOL® cyclodextrin generally allows for increased solubility and, in some cases, increased stability of drugs in aqueous solutions.

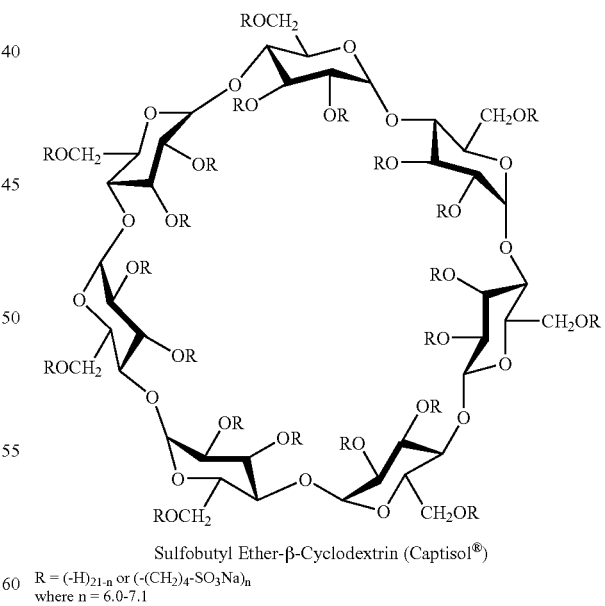

Sulfobutyl Ether-β-Cyclodextrin (Captisol®)
R = (-H)$_{21-n}$ or (-(CH$_2$)$_4$-SO$_3$Na)$_n$
where n = 6.0-7.1

Sulfoalkyl ether cyclodextrins (SAE-CD's), however, are known to have limitations concerning the molecules they can bind with. For example, SAE-CD's but especially Captisol® are known to bind compounds such as nifedipine, nimodipine, nitrendipine and clotrimazole poorly.

Various embodiments of a mixed sulfoalkyl ether cyclodextrin, i.e. a single cyclodextrin comprising two structurally different ether functional groups, are known. Some of the mixed ether cyclodextrins include eicosa-O-(methyl)-6G-O-(4-sulfobutyl)-β-cyclodextrin, heptakis-O-(sulfomethyl)-tetradecakis-O-(3-sulfopropyl)-β-cyclodextrin, heptakis-O-[(1,1-dimethylethyl)dimethylsilyl]-tetradecakis-O-(3-sulfopropyl)-β-cyclodextrin, heptakis-O-(sulfomethyl)-tetradecakis-O-(3-sulfopropyl)-β-cyclodextrin, and heptakis-O-[(1,1-dimethylethyl)dimethylsilyl]-tetradecakis-O-(sulfomethyl)-β-cyclodextrin.

Other known ether cyclodextrin derivatives containing a sulfoalkyl moiety include sulfoalkylthio and sulfoalkylthioalkyl ether derivatives such as octakis-(S-sulfopropyl)-octathio-γ-cyclodextrin, octakis-O-[3-[(2-sulfoethyl)thio]propyl]-β-cyclodextrin], and octakis-S-(2-sulfoethyl)-octathio-γ-cyclodextrin.

Japanese Patent No. JP 05001102 to Yoshinaga discloses a method of preparing sulfonic acid derivatives of cyclodextrins wherein the primary hydroxyl groups of the cyclodextrin are predominantly derivatized to form mono-, di-, tetra-, and hepta-sulfonic acid derivatized CD's.

U.S. Pat. No. 5,241,059 to Yoshinaga discloses methods of preparing cyclodextrins derivatives containing sulfoalkyl ether (SAE), ammonium, phosphoric, carboxyl, hydroxyl, tosyl, t-butyl-dimethylsilyl (TBDMS), azide, trimethyl ammonium, or carboxyalkyl ether CD's. In particular, they disclose mixed derivatives comprising SAE and TBDMS.

PCT International Publication No. WO 01/40316 to Zhang et al. discloses the preparation of 6-mercapto-cyclodextrin derivatives of the general formula CD-6-O—$CH_2$—S—R—X, wherein R can be an alkylene group and X can be an —$SO_3H$ group. The cyclodextrin can be α, β, or γ.

Adam et al. (*J. Med. Chem.* (2002), 45, 1806-1816) disclose a group of CD derivatives containing different functional groups at the C6 position. In particular, they disclose sulfoalkyl (sulfomethyl, sulfoethyl, sulfopropyl) thio ether cyclodextrin derivatives.

Tarver et al. (*Bioorganic & Medicinal Chemistry* (2002), 10, 1819-1827) disclose sulfoalkyl (sulfoethyl) thioalkyl ether cyclodextrin derivatives wherein derivatization occurs on the C6 position.

U.S. Pat. No. 5,594,125 (Jan. 14, 1997) to Seyschab et al. discloses water soluble cyclodextrin derivatives having at least one lipophilic substituent and one hydrophilic radical per cyclodextrin molecule. The hydrophilic substituent can be methyl, ethyl, hydroxyethyl, hydroxy-i-propyl, hydroxy-n-propyl, dihydroxy-i-propyl, dihydroxy-n-propyl, carboxymethyl, carboxyethyl, carboxy-i-propyl, carboxy-n-propyl or an alkali metal salt of the carboxyalkyl substituents. Particularly preferred embodiments for hydrophilic substituent include methyl, 2-hydroxypropyl, 2,3-dihydroxypropyl, Na-carboxymethyl, K-carboxymethyl or Li-carboxymethyl. The lipophilic substituent can be $C_5$-$C_{12}$ hydroxy-alkyl, $C_6$-$C_{10}$ hydroxycycloalkyl, or hydroxypropyl, which is substituted by $C_4$-$C_{12}$ alkyloxy and/or $C_6$-$C_{10}$ aryloxy and/or $C_7$-$C_{15}$ aralkyloxy radicals, where the alkyl radicals can be unbranched or branched. Particularly preferred embodiments for the lipophilic substituent include hydroxyhexyl, hydroxyoctyl, hydroxydecyl, hydroxycyclohexyl, hydroxycyclooctyl, 3-butoxy-hydroxypropyl, 3-hexyloxyhydroxypropyl, 3-(2-ethylhexyloxy)-hydroxypropyl, 3-octyloxy-hydroxypropyl, 3-phenyloxy-hydroxypropyl, 3-cresyloxy-hydroxypropyl or 3-naphthyloxy-hydroxypropyl, where the alkyl radicals are unbranched and even-numbered.

U.S. Pat. No. 5,760,015 (Jun. 2, 1998) and U.S. Pat. No. 5,846,954 to Joullie et al. disclose "one-sided" water soluble cyclodextrin derivatives having at least 10 anionic groups on one side of the CD molecule. The majority of the anionic substituents are located at the C-2 and C-3 positions of the carbohydrate rings of the cyclodextrin. The anionic substituent is the anion of "any strong acid, non-limiting examples of these anions include sulfate, nitrate, sulfonate, and phosphate. Sulfate is preferred." Several anionic substituents are listed; however, only the sulfate anion is exemplified. The derivative also includes a hydrophobic substituent located at least at the C-6 position of the carbohydrate. None of these patents includes enablement of a polymeric or non-polymeric SAE-AE-CD derivative.

U.S. Pat. No. 5,019,562 to Folkman et al. discloses anionic CD derivatives having a sulfate, phosphate, or carboxylate group. U.S. Pat. No. 5,183,809 to Weisz et al. discloses polyionic derivatives having a sulfate, phosphate, carboxylate or nitrate group. None of these patents includes enablement of a polymeric or non-polymeric SAE-AE-CD derivative.

U.S. Pat. No. 5,658,894 to Weisz et al. suggest polymeric CD derivatives, wherein the CD comprises anionic R groups selected from the group consisting of sulfate, phosphate, sulfonate, carboxylate and nitrate, and nonanionic R groups selected from the group consisting of H, alkyl, aryl, ester, ether, thioester, thioether. This patent includes no enablement of a polymeric or non-polymeric SAE-AE-CD derivative.

Alkyl ether derivatized cyclodextrins (AE-CD's) are known. They have been described in various patent literature and their synthesis and properties have been well documented in various reviews and books (see Fromming and Szejtli, Cyclodextrins in Pharmacy, Kluwer Academic Publishing, Dordrecht, 1994 and references therein). Methyl ether CDs are presumed to be strong binders by raising the "height" of the CD ring thus providing an additional area for interaction with interacting molecules. However, a key limitation of these derivatives is their water solubility. In particular, higher alkylated CDs such as ethyl and propyl ether CDs have shown decreasing water solubility with the increasing TDS (total degree of substitution).

As noted above with regard to the SAE-CD's, AE-CD's are also known to have limited utility due to their poor solubility, and lack of safety. For example, AE-CD's are also known to cause a significant amount of red blood cell hemolysis when administered to a subject. Red blood cell hemolysis has been correlated with increased renal toxicity and membrane disruption. AE-CD's, however, can solubilize some compounds better than SAE-CD's can.

To the knowledge of the present inventors, a mixed ether cyclodextrin comprising an alkyl ether functional group and a sulfoalkyl ether functional group on the same cyclodextrin has only been disclosed once. Jiczinszky et al. ("Cyclodextrin: From Basic Research to Market", *International Cyclodextrin Symposium*, 10th, Ann Arbor, Mich., United States, May 21-24, 2000 (2000), 46-52; Wacker Biochem Corp.: Adrian, Mich.) disclose a proposed synthesis of a permethylated 6-O-sulfobutyl ether cyclodextrin derivative. In particular, they disclose a 6-O-(4-sulfobutyl)-permethylated-β-cyclodextrin derivative, wherein the derivative contains only a single sulfobutyl moiety. However, in communications with the author, it was confirmed that the proposed synthesis could not be used to prepare the target derivative. This cyclodextrin derivative, therefore, likely possesses properties that are very similar to the permethylated-β-cyclodextrin, and as has been noted herein, alkylated cyclodextrin derivatives are known to cause a significant amount of hemolysis when administered to a subject. Earlier work by Rajewski et al (*Journal of Pharmaceutical Sciences*, (1995), 84, 927-932) showed that low degrees of sulfobutylation did not prevent red blood cell hemolysis and that higher degrees of substitution were preferable.

It is known in the art that the method of preparation of a cyclodextrin derivative can have a significant impact upon final structure and associated properties of a product derivative. The synthetic scheme can alter the total degree of substitution (TDS) as well as the regiochemistry of substitution (the substitution pattern). For example, the interaction of an alkylating agent with a CD during alkylation, changing of the pH of the reaction milieu, and/or varying of the molar ratio of alkylating agent to CD during alkylation can affect the TDS and the substitution pattern.

A need remains for an improved SAE-CD as well as an improved AE-CD, since each of those derivatives is known to have limitations. Modern drug discovery processes are identifying larger more complex molecules whose physical and chemical properties, especially solubility and stability are becoming more problematic. Therefore, there is a need for CDs capable of interacting with larger more complex molecules. AE-CDs of both β- and γ-CDs can provide this increased area for interaction but suffer from severe safety issues. It would be extremely beneficial to identify a cyclodextrin derivative that is able to provide enhanced properties over a structurally related SAE-CD and over an AE-CD. It would be useful to identify a CD derivative having the beneficial properties of an SAE-CD and an AE-CD but having less of the disadvantages typically associated with those derivatives.

SUMMARY OF THE INVENTION

The present invention seeks to provide water soluble cyclodextrin derivatives that exhibit improved properties and/or performance over known alkyl ether cyclodextrins and known sulfoalkyl ether cyclodextrins. The present derivatives overcome at least some of the disadvantages present in known formulations. The mixed ether cyclodextrin of the invention provides improved properties over the 6-O-(4-sulfobutyl)-permethylated-β-cyclodextrin derivative of Jicsinszky et al. by increasing the degree of substitution of the sulfoalkyl ether moiety and decreasing the degree of substitution of the alkyl ether moiety. Moreover, the mixed ether cyclodextrin of the invention provides improved properties over known SAE-CD's and known AE-CD's. Specifically, SAE-AE-CDs described here provide the ability to interact with larger more complex molecules without sacrificing safety. SAE-AE-CD's of the invention possess a lengthened binding cavity as compared to structurally related SAE-CD's; therefore, the CD derivative of the invention possesses improved binding of some active agents over that observed with a structurally related SAE-CD. The SAE-AE-CD's of the invention possess reduced hemolytic potential toward red blood cells than do AE-CD's. In many cases, the safety of the SAE-AE-CD is comparable to that of a structurally related SAE-CD even though the CD derivative of the invention possesses at least one AE functional group.

One aspect of the invention provides a water soluble sulfoalkyl ether-alkyl ether cyclodextrin derivative (an SAE-AE-CD) comprising one or more alkyl ether (AE) functional groups and one or more sulfoalkyl ether (SAE) functional groups on the same cyclodextrin moiety. The degree of substitution (DS) for each functional group is varied as desired such that the total number of the two functional groups does not exceed the number of hydroxyl groups available in the underivatized parent cyclodextrin. The SAE-AE-CD can comprise a majority of SAE functional groups and a minority of AE and OH functional groups. Alternatively, the SAE-AE-CD can comprise a majority of AE functional groups and a minority of SAE and OH functional groups.

In another embodiment, the SAE-AE-CD comprises a majority of OH functional groups and a minority of SAE and AE functional groups. Therefore, one or more hydroxyl groups in the parent cyclodextrin can remain underivatized by an SAE or AE functional group. In other words, the total degree of substitution (TDS) by both functional groups can be less than the total number of hydroxyl groups in the parent cyclodextrin. In one embodiment, a majority of the hydroxyl groups of the parent cyclodextrin is derivatized by an SAE or AE group.

The regioisomerism of derivatization by the SAE and AE groups can also be varied as desired such that a majority of the SAE groups present is preferentially located at a primary hydroxyl group or at one or both of the secondary hydroxyl groups of the parent cyclodextrin. Likewise, a majority of the AE groups present can be preferentially located at a primary hydroxyl group or at one or both of the secondary hydroxyl groups of the parent cyclodextrin. In one embodiment, the distribution of SAE or AE groups in the CD ring is 2>6>3, while in other embodiments the distribution is 6>2>3. The AE moiety and SAE moiety can be independently or dependently selected at each occurrence within an SAE-AE-CD molecule. The structure of the alkyl portion of the AE and SAE functional groups in a single SAE-AE-CD can be the same or different according to the starting materials and method of preparation employed.

Derivatization (alkylation and sulfoalkylation) of a parent cyclodextrin with precursors of the AE and SAE functional groups can be done in two steps reaction with workup after the first derivatization; in two steps reaction without workup after the first derivatization; in one step reaction with simultaneous addition of the 2 alkylating agents. In one embodiment, an AE-CD is prepared or obtained first, and then the AE-CD is derivatized with an SAE precursor to form an SAE-AE-CD. In another embodiment, an SAE-CD is prepared or obtained first, and then the SAE-CD is derivatized with an AE precursor to form an SAE-AE-CD. Alternatively, a parent cyclodextrin is derivatized in the presence of both an SAE precursor and an AE precursor.

The SAE-AE-CD can be present in less than stoichiometric, stoichiometric or greater than stoichiometric amounts with respect to the amount of another material present in the formulation. Other materials that can be included in an SAE-AE-CD-containing composition include, among other things, one or more excipients and/or one or more active agents.

The composition of the invention can include small amounts (<5%) of each of underivatized parent cyclodextrin, SAE-CD and/or AE-CD that has been added to an SAE-AE-CD-containing composition and/or that is present due to incomplete removal of the underivatized cyclodextrin during processing of an SAE-AE-CD.

The invention also provides an active composition comprising an SAE-AE-CD composition of the invention and an active agent, e.g. therapeutic agent. In this embodiment, the active composition and SAE-AE-CD composition independently and optionally comprise one or more excipients. In one embodiment, the active agent, or a majority thereof, is complexed with the SAE-AE-CD. In another embodiment, the active agent, or a majority thereof, is not complexed with the SAE-AE-CD.

Specific embodiments of the invention include those wherein: 1) the molar ratio of an active agent to SAE-AE-CD is less than one to about one; 2) the SAE-AE-CD composition comprises a compound of the formula 3 or a mixture thereof; 3) the molar ratio of an active agent to SAE-AE-CD is greater than one; 4) the cyclodextrin core of the SAE-AE-CD is β-CD or γ-CD; 5) the degree of substitution (DS) for the SAE functional group is greater than the DS for the AE functional group; 6) the DS for the AE functional group is greater than the DS for the SAE functional group; 7) more than half of the hydroxyl moieties of an SAE-AE-CD are derivatized; 8) half or less than half of the hydroxyl moieties of an SAE-AE-CD are derivatized; 9) the SAE and AE functional groups comprise a similar alkylene (alkyl) radical; and/or 10) the SAE and AE functional groups comprise different alkylene (alkyl) radicals.

An embodiment of the invention excludes an SBE1.0-Me20-β-CD. Another embodiment excludes a SBE1-Me(3v+5)-CD, wherein v is 6, 7 or 8, when the CD ring size includes 6, 7 or 8 glucopyranose units, respectively. Still another embodiment excludes a permethylated β-CD comprising a single —SBE moiety.

The invention also provides a method of preparing an SAE-AE-CD containing composition, wherein the SAE-AE-CD is a compound of the formula 3, the method comprising the steps of:

exposing an SAE-CD, wherein the SAE-CD comprises at least one underivatized hydroxyl moiety, in aqueous alkaline media to an AE precursor for a period of time sufficient, at a temperature sufficient and at a solution pH sufficient to permit formation of an SAE-AE-CD compound and processing the media containing the SAE-AE-CD compound to remove undesired components thereby forming an SAE-AE-CD containing composition.

The invention also provides a method of preparing an SAE-AE-CD containing composition, wherein the SAE-AE-CD is a compound of the formula 3, the method comprising the steps of:

a) exposing an underivatized parent CD in aqueous alkaline media to an AE precursor, an SAE precursor, or a combination of both for a period of time sufficient, at a temperature sufficient and at a solution pH sufficient to permit formation of an AE-CD, SAE-CD, or SAE-AE-CD compound, respectively; and b) if no SAE precursor was present in step a), exposing the AE-CD compound, wherein the AE-CD compound comprises at least one underivatized hydroxyl moiety, in aqueous alkaline media to an SAE precursor for a period of time sufficient, at a temperature sufficient and at a solution pH sufficient to permit formation of an SAE-AE-CD compound; or b) if no AE precursor was present in step a), exposing the SAE-CD compound, wherein the SAE-CD compound comprises at least one underivatized hydroxyl moiety, in aqueous alkaline media to an AE precursor for a period of time sufficient, at a temperature sufficient and at a solution pH sufficient to permit formation of an SAE-AE-CD compound; and c) processing the media containing the SAE-AE-CD compound to remove undesired components thereby forming an SAE-AE-CD containing composition.

The invention also provides a method of preparing an SAE-AE-CD containing composition, wherein the SAE-AE-CD is a compound of the formula 3, the method comprising the steps of:

exposing an AE-CD, wherein the AE-CD comprises at least one underivatized hydroxyl moiety, in aqueous alkaline media to an SAE precursor for a period of time sufficient, at a temperature sufficient and at a solution pH sufficient to permit formation of an SAE-AE-CD compound; and processing the media containing the SAE-AE-CD compound to remove undesired components thereby forming an SAE-AE-CD containing composition.

The invention also provides compositions comprising an SAE-AE-CD compound of the formula 3 as well as compositions comprising a mixture of SAE-AE-CD compounds of the formula 3.

Specific embodiments of an SAE-AE-CD composition can also include those wherein: 1) the composition further comprises AE-CD; 2) the composition further comprises SAE-CD; 3) the composition further comprises SAE-CD and AE-CD; 4) the composition further comprises an underivatized parent CD; 5) the composition further comprises SAE-CD, AE-CD and underivatized parent CD; 6) the composition comprises less than 50% wt. of AE-CD; 7) the composition comprises less than 50% wt. of SAE-CD; 8) the composition comprises less than 50% wt. total of SAE-CD and AE-CD; 9) the composition comprises less than 50% wt. of underivatized parent CD; 10) the composition comprises less than 50% wt. total of SAE-CD, AE-CD and underivatized parent CD; 11) the composition comprises 5% wt. or less of AE-CD; 12) the composition comprises less than 5% wt. of SAE-CD; 13) the composition comprises 5% wt. or less of total SAE-CD and AE-CD; 14) the composition comprises 5% wt. or less of underivatized parent CD; 15) the composition comprises 5% wt. or less of total SAE-CD, AE-CD and underivatized parent CD; 16) the composition comprises greater than 5% wt. and less than 50% wt. of AE-CD; 17) the composition comprises greater than 5% wt. and less than 50% wt. of SAE-CD; 18) the composition comprises greater than 5% wt. and less than 50% wt. total of SAE-CD and AE-CD; 19) the composition comprises greater than 5% wt. and less than 50% wt. of underivatized parent CD; or 20) the composition comprises greater than 5% wt. and less than 50% wt. total of SAE-CD, AE-CD and underivatized parent CD.

These and other aspects of this invention will be apparent upon reference to the following detailed description, examples, claims and attached figures.

BRIEF DESCRIPTION OF THE FIGURES

The following drawings are given by way of illustration only, and thus are not intended to limit the scope of the present invention.

DETAILED DESCRIPTION OF THE INVENTION

Figure 1:
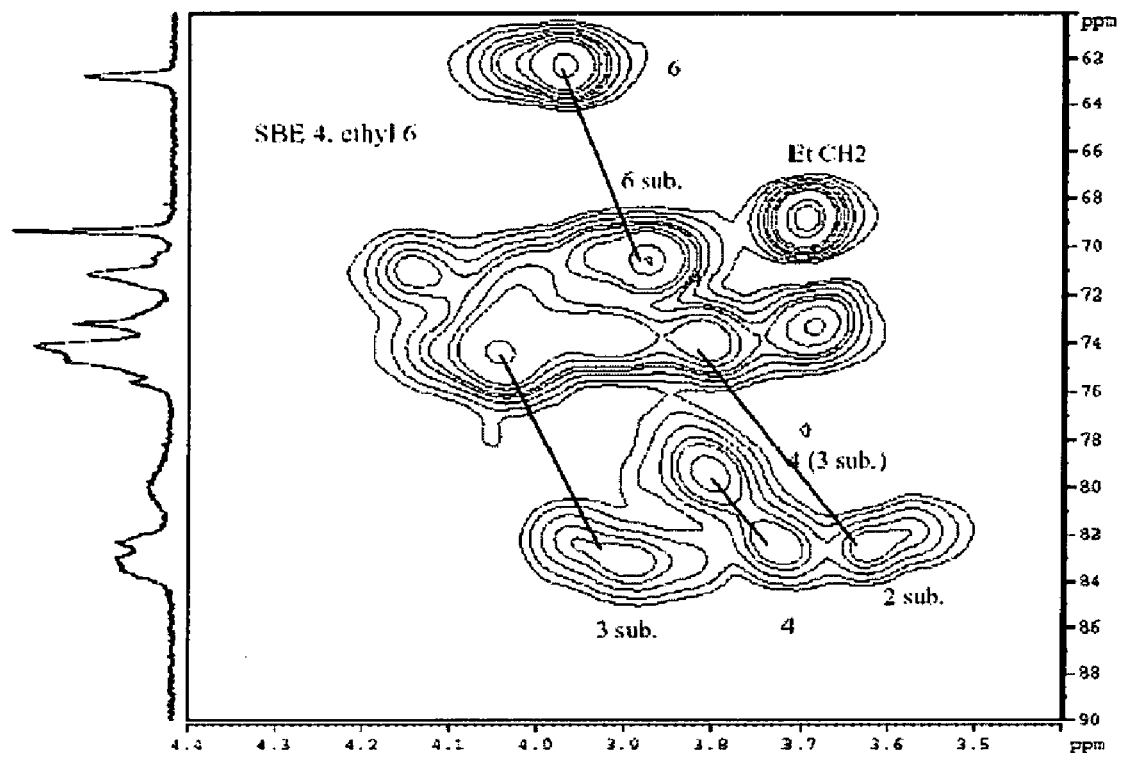
FIG. 1 depicts an HMQC spectrum of an exemplary SAE-AE-CD (SBE4.6-Et6.0-β-CD).
Figure 1:
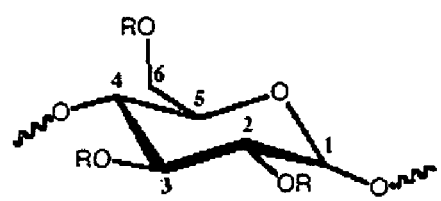
Figure 1:
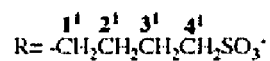
Figure 1:
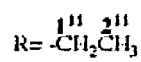
Figure 1:

An SAE-AE-CD of the invention provides unexpected advantages over a structurally related SAE-CD and/or AE-CD. By "structurally related" is meant, for example, that the SAE substituent of the SAE-CD being compared is essentially the same as the SAE substituent of SAE-AE-CD being compared, and likewise, the AE substituent of the AE-CD being compared is essentially the same as the AE substituent of SAE-AE-CD being compared. Exemplary advantages of an SAE-AE-CD over a structurally related SAE-CD may include an improved ability of the SAE-AE-CD to form complexes and thus solubilize and/or stabilize a neutral, cationic or anionic molecule better than can the structurally related SAE-CD. Exemplary advantages of an SAE-AE-CD over a structurally related AE-CD may include an improved ability of the SAE-AE-CD to solubilize and/or stabilize a cationic molecule better than can the structurally related AE-CD and more importantly be less hemolytic to red blood cells thus providing greater safety.

A composition of the invention can be a liquid, solid, suspension, colloid, pellet, bead, granule, film, powder, gel, cream, ointment, paste, stick, tablet, capsule, osmotic device, dispersion, emulsion, patch or any other type of formulation.

An SAE-AE-CD can be prepared by alkylation of an SAE-CD of the Formula 1 with an AE precursor, wherein the SAE-CD is:

Formula 1 wherein:
p is 4, 5 or 6;
$R_1$ is independently selected at each occurrence from —OH or -SAET;
-SAE is a —O—($C_2$-$C_6$ alkylene)-$SO_3^-$ group, wherein at least one SAE is independently a —O—($C_2$-$C_6$ alkylene)-$SO_3^-$ group, preferably a —O—$(CH_2)_g$$SO_3^-$ group, wherein g is 2 to 6, preferably 2 to 4, (e.g. —$OCH_2CH_2CH_2SO_3^-$ or —$OCH_2CH_2CH_2CH_2SO_3^-$);
T is independently selected at each occurrence from the group consisting of pharmaceutically acceptable cations, which group includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine, ethylenediamine and ($C_4$-$C_8$)-cycloalkanolamine among others; and provided that at least one $R_1$ is a hydroxyl moiety and at least one $R_1$ is -SAET. When at least one $R_1$ in the CD molecule is -SAET, the degree of substitution, in terms of the -SAET moiety, of the SAE-AE-CD molecule is understood to be at least one.

The SAE-CD used is described in U.S. Pat. No. 5,376,645 and U.S. Pat. No. 5,134,127 to Stella et al, the entire disclosures of which are hereby incorporated by reference. Parmerter et al. (U.S. Pat. No. 3,426,011), Lammers et al. (*Recl. Trav. Chim. Pays-Bas* (1972), 91(6), 733-742); *Staerke* (1971), 23(5), 167-171), Qu et al. (*J. Inclusion Phenom. Macro. Chem.*, (2002), 43, 213-221), Yoshinaga (Japanese Patent No. JP 05001102; U.S. Pat. No. 5,241,059), Zhang et al. (PCT International Publication No. WO 01/40316), Adam et al. (*J. Med. Chem.* (2002), 45, 1806-1816), and Tarver et al. (*Bioorganic & Medicinal Chemistry* (2002), 10, 1819-1827) disclose other suitable sulfoalkyl ether derivatized cyclodextrins for use as starting materials in preparing an SAE-AE-CD according to the invention.

A suitable SAE-CD starting material can be made according to the disclosure of Stella et al., Parmerter et al., Lammers et al., Qu et al., Yoshinaga, Zhang et al. Adam et al. or Tarver et al. A suitable SAE-CD can also be made according to the procedure(s) described herein. Prior to alkylation with an AE precursor, the SAE-CD is optionally processed to remove the major portion of the underivatized parent cyclodextrin or other contaminants.

An SAE-AE-CD can be prepared by sulfoalkylation of an AE-CD of the Formula 2 with SAE precursor, wherein the AE-CD is:

Formula 2 wherein:
m is 4, 5 or 6; and
R is independently selected at each occurrence from the group consisting of —OH and AE;
AE is —O($C_1$-$C_3$ alkyl);
provided that at least one R is —OH; and at least one AE is present.

Suitable AE-CD starting materials include, by way of example and without limitation commercially and non-commercially available AE-CDs from various sources.

An AE-CD starting material can be prepared according to standard procedures available in the literature or methods described in this invention. Dimethyl cyclodextrin is available from FLUKA Chemie (Buchs, CH) or Wacker (Iowa). Exemplary water-soluble AE-CD molecules include alkylated derivatives such as methyl, ethyl, and propyl. All of these materials can be made according to methods known in the prior art. Suitable derivatized cyclodextrins are disclosed in *Modified Cyclodextrins: Scaffolds and Templates for Supramolecular Chemistry* (Eds. Christopher J. Easton, Stephen F. Lincoln, Imperial College Press, London, UK, 1999) and *New Trends in Cyclodextrins and Derivatives* (Ed. Dominique Duchene, Editions de Santé, Paris, France, 1991).

Alternatively, an SAE-AE-CD is prepared from an underivatized parent cyclodextrin such as α-CD, β-CD or γ-CD by alkylation and sulfoalkylation, or vice versa, of the parent cyclodextrin. The α-CD, β-CD or γ-CDs are commercially available from WACKER BIOCHEM CORP. (Adrian, Mich.) and other sources. Methods for preparing an SAE-AE-CD are detailed below.

As used herein, an "alkyl ether precursor" (AE precursor) means any agent or combination of agents and reaction conditions that results in the formation of an alkyl ether substituent on a hydroxyl of a parent cyclodextrin. An AE precursor will react with the oxygen atom of a hydroxyl moiety of a parent cyclodextrin thereby converting the hydroxyl moiety to an alkyl ether moiety on the cyclodextrin. An AE precursor is also referred to herein as an alkylating agent. Exemplary alkylating agents that can be used to derivatize (etherify) the cyclodextrin include, by way of example and without limitation, various alkyl sulfate esters. Specific AE precursors include sulfate esters such as diethyl sulfate, dimethyl sulfate and dipropyl sulfate.

As used herein, a "sulfoalkyl ether precursor" (SAE precursor) means any agent or combination of agents and reaction conditions that results in the formation of a sulfoalkyl ether substituent on a hydroxyl of a parent cyclodextrin. An SAE precursor will react with the oxygen atom of a hydroxyl moiety of a parent cyclodextrin thereby converting the hydroxyl moiety to a sulfoalkyl ether moiety on the cyclodextrin. An SAE precursor is also referred to herein as a sulfoalkylating agent. Exemplary sulfoalkylating agents that can be used to derivatize (etherify) the cyclodextrin include, by way of example and without limitation, alkyl sultone. Specific SAE precursors include 1,4-butane sultone, 1,5-pentane sultone, 1,3-propane sultone, and other sulfoalkylating agents.

An (SAET)x-(AE)y-CD of the invention is represented by the Formula 3:

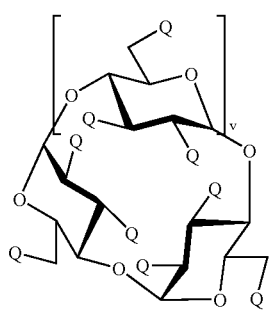

Formula 3 wherein:

v is 4, 5 or 6; and

Q is independently selected at each occurrence from the group consisting of —OH, -SAET" and -AE";

x is the degree of substitution for the SAET moiety and is 1 to 3v+5;

y is the degree of substitution for the AE moiety and is 1 to 3v+5;

-SAE is —O—($C_2$-$C_6$ alkylene)-$SO_3^-$;

T is independently at each occurrence a cation; and

AE is —O($C_1$-$C_3$ alkyl);

provided that at least one -SAET moiety and at least one -AE moiety are present; and the sum of x, y and the total number of —OH groups in a cyclodextrin derivative is 3v+6.

Specific embodiments of the derivative of the invention include those wherein: 1) the alkylene moiety of the -SAE has the same number of carbons as the alkyl moiety of the -AE; 2) the alkylene moiety of the -SAE has a different number of carbons than the alkyl moiety of the -AE; 3) the alkyl and alkylene moieties are independently selected from the group consisting of a straight chain or branched moiety; 4) the alkyl and alkylene moieties are independently selected from the group consisting of a saturated or unsaturated moiety.

The terms "alkylene" and "alkyl," as used herein (e.g., in the —O—($C_2$-$C_6$-alkylene)$SO_3^-$ group or in the alkylamines cations), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

Specific embodiments of the invention provide the SAE-AE-CD's listed in the tables below, which tables include the identity of the alkyl portion for each the SAE and AE functional groups, the degree of substitution determined for each the SAE and AE functional groups, the molar equivalents of alkylating agent (e.g., diethyl sulfate) per mole of SAE-CD used in preparing the SAE-AE-CD, and the synthetic yield for preparation of the SAE-AE-CD. The synthetic procedures for preparing these derivatives are detailed in the examples below.

| SAE-AE-γ-CD DERIVATIVES | | | |
|---|---|---|---|
| PRODUCT SAEx-AEy-γ-CD | DIALKYLSULFATE EQUIVALENTS | SYNTHETIC YIELD (%) | DS "y" |
| Et4.5-γ-CD | 5 | 60 | 4.5 |
| SBE5.2-Et1-γ-CD | 1.5 | 60 | 1.2 |
| SBE5.2-Et4.9-γ-CD | 6.5 | 85 | 4.9 |
| SBE5.2-Et6.9-γ-CD | 12 | 80 | 6.9 |
| SBE5.2-Et8.9-γ-CD | 20 | 85 | 8.9 |
| SBE9-Et4.5-γ-CD | 6.5 | 85 | 4.5 |
| SBE5.2-Me4.5-γ-CD | 5 | 60 | 4.5 |
| Me5.1-γ-CD | 5.5 | 60 | 5.1 |
| SBE5.2-Me3.5-γ-CD | 5 | 70 | 3.5 |
| SBE5.2-Me5.2-γ-CD | 6.5 | 85 | 5.2 |
| Pr5.5-γ-CD | 6.0 | 60 | 5.5 |
| SBE5.2-Pr5.4-γ-CD | 5 | 70 | 5.4 |
| SBE5.2-Pr8.1-γ-CD | 10 | 70 | 8.1 |
| SPE5.2-Pr5.5-γ-CD | 6.5 | 65 | 5.5 |

In the table above, the control AE-CD (Et4.5-γ-CD) was prepared according to the examples below, and γ-CD was used as the parent cyclodextrin for each derivative included in the table. Each SAE-AE-CD was prepared according to the examples below. The letter "x" in the formula SAEx-AEy-γ-CD denotes the degree of substitution (DS) determined experimentally for the SAE functional group, and the letter "y" denotes the degree of substitution (DS) determined experimentally for the AE functional group. The identity of the alkyl group "A" in each the SAE and AE function group is noted: SBE denotes a sulfobutyl ether group; Me denotes a methyl ether group, Et denotes an ethyl ether group; and Pr denotes a propyl ether group. The dialkylsulfate used corresponds to the alkyl ether substituent formed on the CD, i.e. diethylsulfate was used to prepare the ethyl ether derivatized CD's, dimethylsulfate for the methyl ether derivatives, and dipropylsulfate for the propyl ether derivatives.

| SAE-AE-β-CD DERIVATIVES | | | |
|---|---|---|---|
| PRODUCT SAEx-AEy-β-CD | DIALKYLSULFATE EQUIVALENTS | SYNTHETIC YIELD (%) | DS "y" |
| Et4.2-β-CD | 5 | 65 | 4.2 |
| SBE4.6-Et1-β-CD | 1.5 | 70 | 1.3 |
| SBE4.6-Et3.5-β-CD | 6.5 | 85 | 3.5 |
| SBE4.6-Et6.5-β-CD | 12 | 80 | 6.5 |
| SBE4.6-Et8.5-βCD | 20 | 85 | 8.5 |
| SBE7-Et3.5-β-CD | 6.5 | 85 | 3.5 |
| Me5.1-β-CD | 5.5 | 60 | 5.1 |
| SBE4.6-Me4.1-β-CD | 5 | 80 | 4.1 |

In the table above, the control AE-CD (Et-β-CD) was prepared according to the examples below, and β-CD was used as the parent cyclodextrin for each derivative included in the table. Each SAE-AE-CD was prepared according to the examples below.

Further exemplary SAE-AE-CD compounds of the invention include:

| SAEx-AEy-α-CD | SAEx-AEy-β-CD | SAEx-AEy-γ-CD |
|---|---|---|
| SEEx-Mey-α-CD | SEEx-Mey-β-CD | SEEx-Mey-γ-CD |
| SEEx-Ety-α-CD | SEEx-Ety-β-CD | SEEx-Ety-γ-CD |
| SEEx-Pry-α-CD | SEEx-Pry-β-CD | SEEx-Pry-γ-CD |
| SPEx-Mey-α-CD | SPEx-Mey-β-CD | SPEx-Mey-γ-CD |
| SPEx-Ety-α-CD | SPEx-Ety-β-CD | SPEx-Ety-γ-CD |
| SPEx-Pry-α-CD | SPEx-Pry-β-CD | SPEx-Pry-γ-CD |
| SBEx-Mey-α-CD | SBEx-Mey-β-CD | SBEx-Mey-γ-CD |
| SBEx-Ety-α-CD | SBEx-Ety-β-CD | SBEx-Ety-γ-CD |
| SBEx-Pry-α-CD | SBEx-Pry-β-CD | SBEx-Pry-γ-CD |
| SPtEx-Mey-α-CD | SPtEx-Mey-β-CD | SPtEx-Mey-γ-CD |
| SPtEx-Ety-α-CD | SPtEx-Ety-β-CD | SPtEx-Ety-γ-CD |
| SPtEx-Pry-α-CD | SPtEx-Pry-β-CD | SPtEx-Pry-γ-CD |
| SHEx-Mey-α-CD | SHEx-Mey-β-CD | SHEx-Mey-γ-CD |
| SHEx-Ety-α-CD | SHEx-Ety-β-CD | SHEx-Ety-γ-CD |
| SHEx-Pry-α-CD | SHEx-Pry-β-CD | SHEx-Pry-γ-CD |

An embodiment of the present invention provides compositions containing a mixture of cyclodextrin derivatives, having the structure set out in formula 3. In a single parent CD molecule, there are $3v+6$ hydroxyl moieties available for derivatization.

The degree of substitution (DS) for a specific moiety (SAE or AE, for example) is a measure of the number of SAE (or AE) substituents attached to an individual CD molecule, in other words, the moles of substituent per mole of CD. Therefore, each substituent has its own DS for an SAE-AE-CD of the invention. The total degree of substitution (TDS) for an SAE-AE-CD is a measure of the total number of SAE and AE substituents present per CD molecule. Therefore, SAE4.0-AE5.0-CD has a TDS (per CD molecule) of 9.0 (4.0+5.0), and it has a DS (per CD molecule) of 4.0 for the SAE group and DS of 5.0 for the AE group. The TDS can be as high as $3v+6$ (the maximum number of available hydroxyl groups) or as low as 2 (wherein, on average, a single CD comprises a single SAE moiety and a single AE moiety). For example, a TDS of 10 means that the values of x and y, in an SAEx-AEy-CD, add up to 10, wherein x can range from 1 to 9 and y and range from 9 to 1, respectively.

A composition of the invention comprises a mixture of different SAE-AE-CD molecules. More specifically, an SAEx-AEy-CD composition comprises plural SAE-AE-CD molecules each having a specific degree of substitution for each substituent. As a consequence, the individual DS for SAE and for AE of an SAEx-AEy-CD composition represents an average of the individual DS values of the population of individual molecules in the composition. For example, an SAE5.2-AE6.9-CD composition comprises a mixture of SAEx-AEy-CD molecules, wherein x (the DS for SAE groups) might range from 1 to 10-11 for individual CD molecules and y (the DS for AE groups) might range from 1 to 11-12 for individual CD molecules; however, the population of SAE-AE-CD molecules is such that the average value for x (the average DS for SAE groups) is 5.2 and for y (the average DS for AE groups) is 6.9. For this same composition, the average TDS is 12.1 (obtained from: 5.2+6.9).

An SAE-AE-CD composition can contain on average at least one to $\leq 3v+5$ SAE moieties per cyclodextrin molecule and on average at least one to $\leq 3v+5$ AE moieties per cyclodextrin molecule.

The invention also includes compositions containing cyclodextrin derivatives having a narrow or wide and high or low TDS (and/or DS). These combinations can be optimized as needed to provide cyclodextrin compositions having particular properties.

A parent cyclodextrin includes a secondary hydroxyl group on the C-2 and C-3 positions of the glucopyranose residues forming the cyclodextrin and a primary hydroxyl on the C-6 position of the same. Each of these hydroxyl moieties is available for derivatization by an SAE precursor or AE precursor. Depending upon the synthetic methodology employed in making an SAE-AE-CD, the SAE and AE moieties may be distributed randomly or in a somewhat ordered manner among the available hydroxyl positions. One embodiment of the invention includes an SAE-AE-CD molecule wherein a majority of the SAE moieties is located at the C-6 position, and a majority of the AE moieties is located at the C-2 and/or C-3 position. Another embodiment of the invention includes an SAE-AE-CD molecule wherein a majority of the SAE moieties is located at the C-2 and/or C-3 position, and a majority of the AE moieties is located at the C-6 position. Still another embodiment of the invention includes an SAE-AE-CD molecule wherein the SAE and AE moieties are substantially evenly distributed among the C-2, C-3 and C-6 positions. For low DS derivatives, the invention also provides an embodiment wherein a majority of the AE and SAE moieties is located at the C-2 and/or C-3 position, or an embodiment wherein a majority of the AE and SAE moieties is located at the C-6 position.

The SAE and AE moieties can have the same type of alkylene (alkyl) radical or the alkylene radicals can be different. By way of example and without limitation, the SAE moiety can be a sulfobutyl moiety, and the AE moiety can be an ethyl moiety. In a similar manner, the SAE moiety can be a sulfopropyl moiety, and the AE moiety can be a propyl moiety. In one embodiment, the alkylene radical of the SAE group is the same as the alkyl radical of the AE group. In another embodiment, the alkylene radical of the SAE group is different than the alkyl radical of the AE group.

By controlling the relative ratio of SAE moiety to AE moiety in a cyclodextrin, SAE-AE-CD molecules and compositions having different physical properties can be prepared. The hydrophobicity and hydrophilicity of the SAE-AE-CD can be balanced by preparing derivatives possessing a predetermined degree of substitution for each functional group, by preparing derivatives possessing a predetermined total degree of substitution, and/or by using predetermined AE and SAE precursors having different degrees of hydrophobicity and hydrophilicity relative to one another. For example, an SAE-AE-CD composition having a first TDS can possess greater solubilizing power for a particular compound than does a second SAE-AE-CD composition having a different TDS.

To the extent that the population of SAE-AE-CD molecules in the SAEx-AEy-CD composition each has the same SAE moiety and the same AE moiety, then the invention provides a composition containing a single type of cyclodextrin derivative. That said, it should be understood that the SAE-AE-CD of the invention can also comprise residual or small amounts of parent CD, SAE-CD and/or AE-CD. Where the amount of parent CD, SAE-CD, or AE-CD present in the SAEx-AEy-CD is ≦5% wt. (defined as a residual amount), the SAEx-AEy-CD is said to be substantially free of the parent CD, SAE-CD, or AE-CD, respectively.

If the SAEx-AEy-CD composition comprises greater than 5% of parent CD, SAE-CD and/or AE-CD, the properties of the SAEx-AEy-CD composition can be modified by independently or interdependently controlling the amount of each CD component in the composition. For example, where the parent CD or the AE-CD are known to be toxic, the SAEx-AEy-CD is processed to minimize their content. If the parent CD or the AE-CD are known to be non-toxic, SAEx-AEy-CDs containing 5% or more of the parent CD or the AE-CD can be prepared. Limitations other than safety also need to be considered such as solubility of the parent CD or the AE-CD. In one embodiment, the SAEx-AEy-CD comprises between about 5% to less than 50% of the sum total of SAE-CD, AE-CD and parent CD. Individually, the amounts of SAE-CD, AE-CD and parent CD in the SAE-AE-CD can range from 0 to 49.9% provided the sum total of their amounts is less than 50% thus ensuring that the SAE-AE-CD remains the major component.

The SAEx-AEy-CD derivatives of the invention include embodiments wherein the SAEx-AEy-CD comprises a majority of the cyclodextrin molecules present. In other words, the molar or weight percentage of SAEx-AEy-CD is greater than the sum total of SAE-CD, AE-CD and/or parent CD present. In this manner, the SAEx-AEy-CD is present as a major portion of the cyclodextrin molecules present in a cyclodextrin composition.

The term SAE is used to denote a sulfoalkyl (alkylsulfonic acid) ether moiety it being understood that the SAE moiety comprises a cation (T) unless otherwise specified. Accordingly, the terms SAE and SAET may, as appropriate, be used interchangeably herein.

Since SAE-CD and SAE-AE-CD are poly-anionic cyclodextrins, they can be provided in different salt forms. Suitable counterions include cationic organic atoms or molecules and cationic inorganic atoms or molecules. The SAE-AE-CD can include a single type of counterion or a mixture of different counterions. The properties of the SAE-AE-CD can be modified by changing the identity of the counterion present. For example, a first salt form of an SAE-AE-CD composition can possess greater osmotic potential than a different second salt form of same SAE-AE-CD, or a first salt form may be exhibit improved tabletting properties over a second salt form.

By "complexed" is meant "being part of a clathrate or inclusion complex with", i.e., a complexed therapeutic agent is part of a clathrate or inclusion complex with a cyclodextrin derivative. By "major portion" is meant greater than about 50% by weight or greater than about 50% on a molar basis. Thus, a formulation according to the present invention may contain an active agent of which more than about 50% by weight is complexed with a cyclodextrin. The actual percent of active agent that is complexed will vary according to the complexation equilibrium binding constant characterizing the complexation of a specific cyclodextrin with a specific active agent. The invention also includes embodiments wherein the active agent is not complexed with the cyclodextrin or wherein a minor portion of the active agent is complexed with the derivatized cyclodextrin. It should be noted that an SAE-AE-CD, or any other anionic derivatized cyclodextrin, can form one or more ionic bonds with a positively charged compound. This ionic association can occur regardless of whether the positively charged compound is complexed with the cyclodextrin by inclusion complexation.

SAE-AE-CD possesses greater water solubility than the corresponding parent cyclodextrin from which it is made. Underivatized α-CD has a water solubility of about 14.5% w/v at saturation. Underivatized β-CD has a water solubility of about 1.85% w/v at saturation. Underivatized γ-CD has a water solubility of about 23.2% w/v at saturation although this number has been in question, i.e., practically, clear 23.2% solutions of γ-CD cannot be made and maintained clear. The water solubility of the SAE-AE-CD is greater than 50% w/v. For example, all the SAE-AE-CDs prepared here (see examples that follow) have a water solubility of >50% w/v.

An SAE-AE-CD possesses greater water solubility than an AE-CD having the same AE functional group and degree of substitution thereof. For example, dimethyl-beta-cyclodextrin (Me2-β-CD, an AE-CD) forms a 43% w/w aqueous solution at saturation; however, SBE7-Me2-β-CD will have a greater water solubility due to its increased ionic nature. In addition, Me2-β-CD, is very toxic if administered parenterally as well as to mucous surfaces like the nasal cavity and the cornea of the eye. SBE7-Me2-β-CD is less irritating to mucous surfaces and presumably the kidney based on its lower red blood cell hemolysis.

Figure 6A:
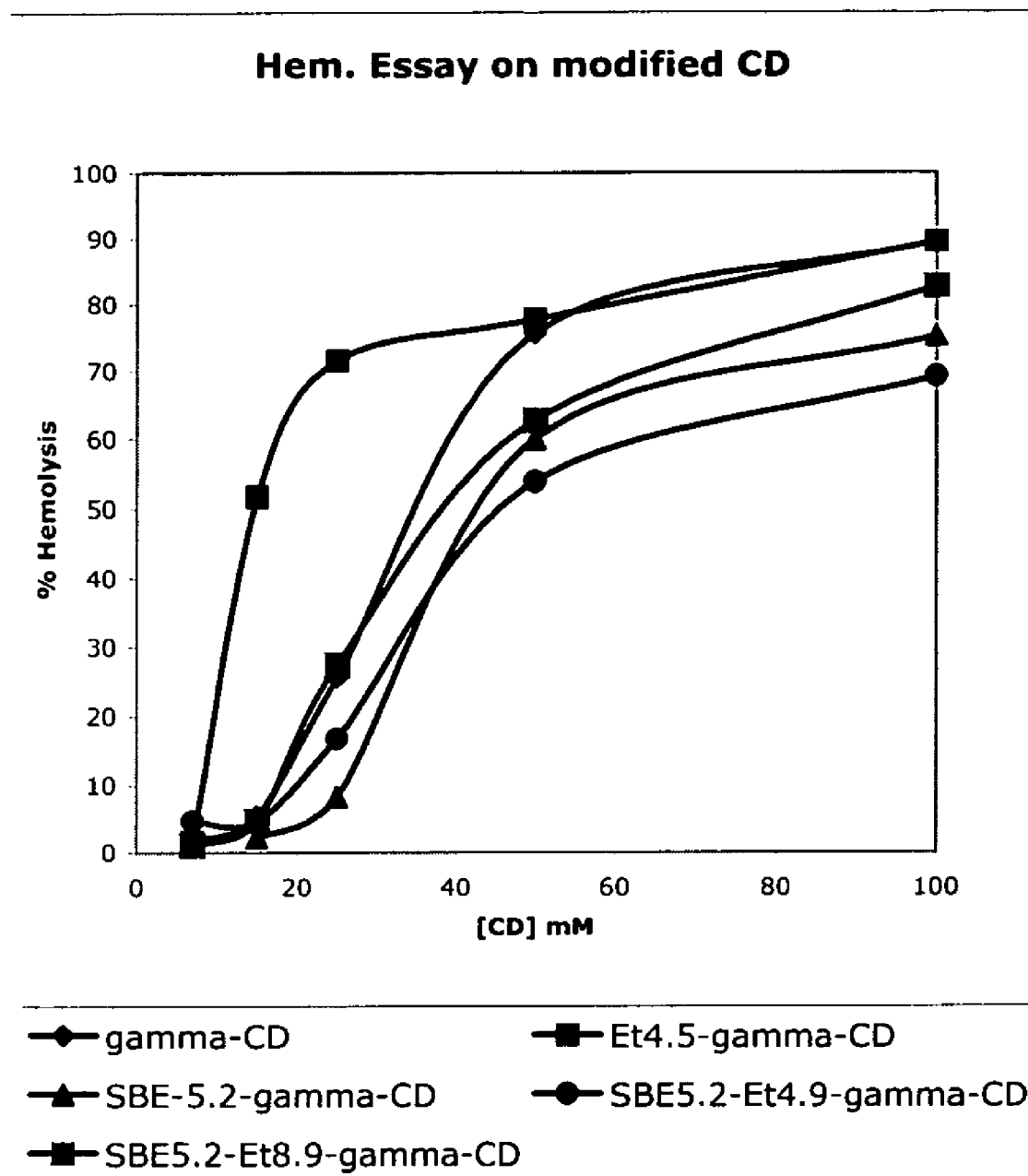
FIGS. 6a-6b depict a chart of concentration of cyclodextrin versus observed percentage of rabbit red blood cell hemolysis.
Figure 6B:
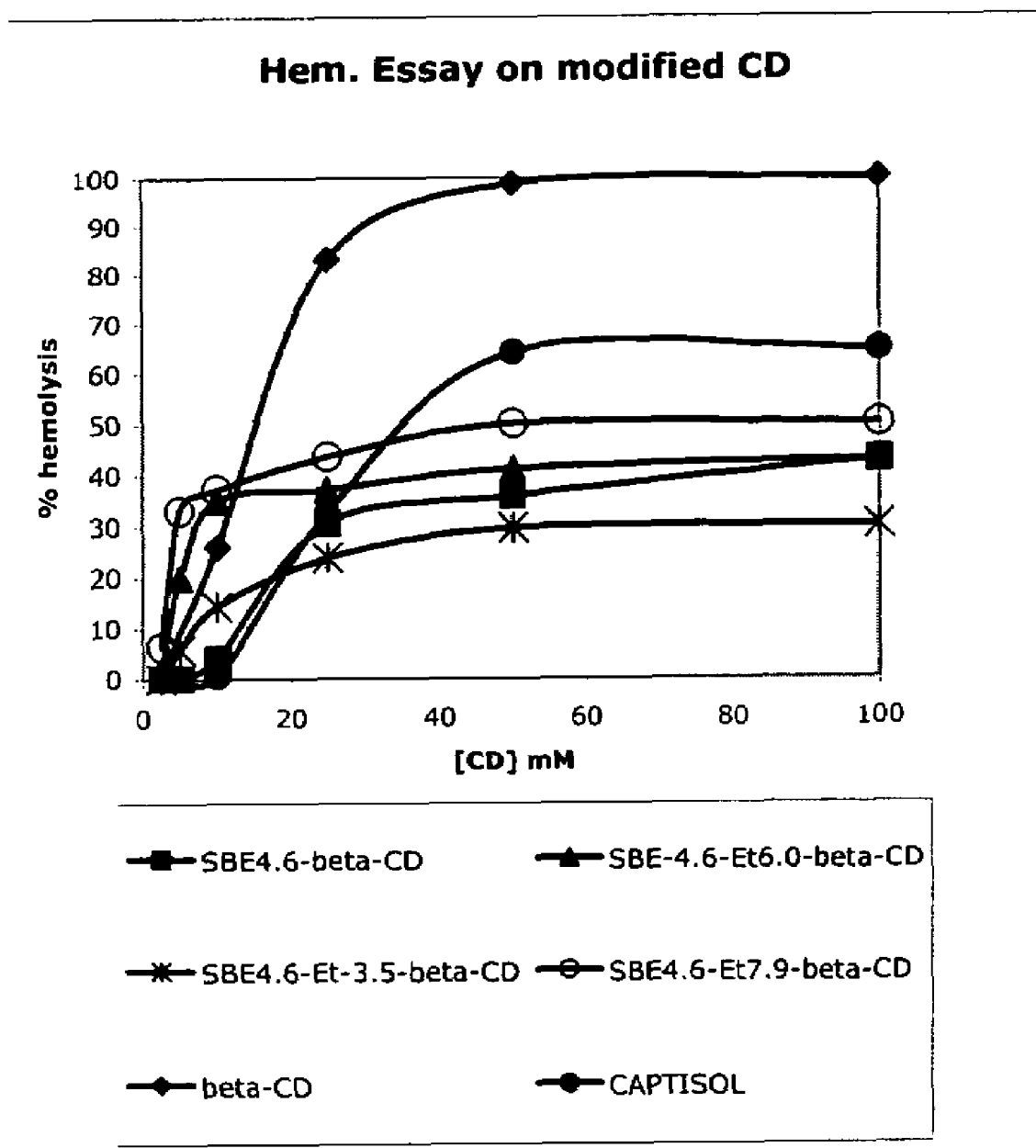
Figure 6C:
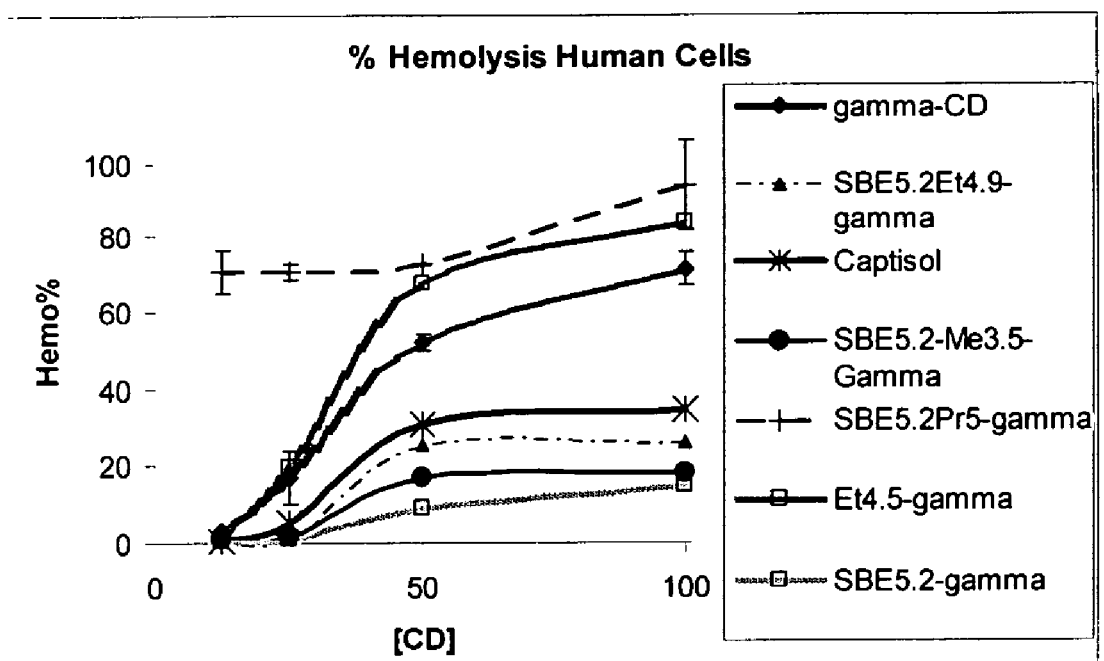
FIG. 6c depicts a chart of concentration of cyclodextrin versus observed percentage of human red blood cell hemolysis.

FIG. 6a depicts a chart of the effect that increasing the concentration of cyclodextrin has on the hemolysis of red blood cells. The chart includes data for γ-CD, SBE5.2-γ-CD, SBE5.2-Et8.9-γ-CD, Et4.5-γ-CD, and SBE5.2-Et4.9-γ-CD. FIG. 6b depicts the results of the same type of hemolysis assays for β-CD, SBE4.6-β-CD; SBE4.6-Et6.5-β-CD, SBE4.6-Et3.5-β-CD, SBE4.6-Et8.5-β-CD and CAPTISOL™. FIG. 6c depicts the results of hemolysis assays for γ-CD, SBE5.2-Et4.9-γ-CD, SBE6.5-β-CD, SBE5.2-Me3.5-γ-CD, and SBE5.2-Pr5-γ-CD, Et-γ-CD, and SBE5.2-γ-CD. The results demonstrate that sulfoalkylation of the Et4.5-γ-CD results in a safer CD having a lower hemolytic potential. Accordingly, the invention provides a method of reducing the hemolytic potential of an AE-CD, the method comprising the step of sulfoalkylating the AE-CD thereby converting it to an SAE-AE-CD having a reduced hemolytic potential as compared to the AE-CD.

The following tables detail some of the SAE-AE-CD's according to the invention. These products were made according to the examples below. The table indicates the inclusion complexes formed with the indicated drugs and cyclodextrins as well as their corresponding linear binding constants (K1:1) determined at 25° C.

| Substrate | Cyclodextrin SAEx-AEy-γ-CD | K1:1 25° C. |
|---|---|---|
| α-Me-Prednisolone | γ-CD | 3038(269) |
| | $(SBE)_{5.2}$-γ-CD | 1392.37(67.4) |
| | $(SBE)_{5.2}$-γ-$Et_{4.9}$-CD | 4630.4(10.3) |

-continued

| Substrate | Cyclodextrin SAEx-AEy-γ-CD | K1:1 25° C. |
|---|---|---|
| | (SBE)$_{5.2}$-γ-Et$_{6.9}$-CD | 1987.53(80.54) |
| | (SBE)$_{5.2}$-γ-Et$_{8.9}$-CD | 935.59(26.34) |
| Prednisolone | γ-CD | 3300.42(21) |
| | (SBE)$_{5.2}$-γ-CD | 1632(10) |
| | (SBE)$_{5.2}$-γ-Et$_{4.9}$-CD | 2338(26.11) |
| | (SBE)$_{5.2}$-γ-Et$_{6.9}$-CD | 2805.66(126) |
| | (SBE)$_{5.2}$-γ-Et$_{8.9}$-CD | 1371.25(27.5) |
| Nifedipine | γ-CD | 1416.1(162) |
| | (SBE)$_{5.2}$-γ-CD | 379.73(73.03) |
| | (SBE)$_{5.2}$-γ-Et$_{4.9}$-CD | 925.82(104.6) |
| | (SBE)$_{5.2}$-γ-Et$_{6.9}$-CD | 977.42(0.75) |
| | (SBE)$_{5.2}$-γ-Et$_{8.9}$-CD | 1367.8(19.37) |
| Nimodipine | γ-CD | 1780(190) |
| | (SBE)$_{5.2}$-γ-CD | 2925(300) |
| | (SBE)$_{5.2}$-γ-Et$_{4.9}$-CD | 5515(102) |
| | (SBE)$_{5.2}$-γ-Et$_{6.9}$-CD | 5814(219) |
| | (SBE)$_{5.2}$-γ-Et$_{8.9}$-CD | 6045(100) |
| Nitrendipine | γ-CD | 2508(59) |
| | (SBE)$_{5.2}$-γ-CD | 4288(6) |
| | (SBE)$_{5.2}$-γ-Et$_{4.9}$-CD | 6578.5(136) |
| | (SBE)$_{5.2}$-γ-Et$_{6.9}$-CD | 2138(81.9) |
| | (SBE)$_{5.2}$-γ-Et$_{8.9}$-CD | 1980(99) |
| Clotrimazole | γ-CD | 1015(30) |
| | (SBE)$_{5.2}$-γ-CD | 1592(55) |
| | (SBE)$_{5.2}$-γ-Et$_{4.9}$-CD | 3143.3(84) |
| | (SBE)$_{5.2}$-γ-Et$_{6.9}$-CD | 3015.2(70) |
| | (SBE)$_{5.2}$-γ-Et$_{8.9}$-CD | 1620.8(80) |
| Triamcinolone | γ-CD | 9769(560) |
| | (SBE)$_{5.2}$-γ-CD | 4172(258) |
| | (SBE)$_{5.2}$-γ-Et$_{4.9}$-CD | 4505(167) |
| | (SBE)$_{5.2}$-γ-Et$_{6.9}$-CD | 4383(378) |
| | (SBE)$_{5.2}$-γ-Et$_{8.9}$-CD | 3983(1081) |
| Camptothecin | γ-CD | 73 |
| | (SBE)$_{5.2}$-γ-CD | 50(18) |
| | (SBE)$_{5.2}$-γ-Et$_{4.9}$-CD | 90(20) |
| | (SBE)$_{5.2}$-γ-Et$_{6.9}$-CD | 20(7) |
| | (SBE)$_{5.2}$-γ-Et$_{8.9}$-CD | 20(7) |
| α-Me-Prednisolone | (SBE)$_{6.5}$-β-CD | 721(57) |
| | (SBE)$_{4.6}$-β-CD | 719(84) |
| | SBE)$_{4.6}$-β-Et$_{3.5}$-CD | 7958.8(494) |
| | (SBE)$_{4.6}$-Et$_{5.9}$-β-CD | 6080.5(649) |
| | (SBE)$_{4.6}$-Et$_{7.9}$-β-CD | 6567.2(345) |
| Prednisolone | (SBE)$_{6.5}$-β-CD | 1821(58) |
| | (SBE)$_{4.6}$-β-CD | 1131(85.28) |
| | SBE)$_{4.6}$-β-Et$_{3.5}$-CD | 3165(153.2) |
| | (SBE)$_{4.6}$-Et$_{5.9}$-β-CD | 2748(123) |
| | (SBE)$_{4.6}$-Et$_{7.9}$-β-CD | 1140(109) |
| Nifedipine | β-CD | 121.9(35) |
| | (SBE)$_{6.5}$-β-CD | 600.5(13.5) |
| | (SBE)$_{4.6}$-β-CD | 1369.25(52.75) |
| | (SBE)$_{4.6}$-Et$_{3.5}$-β-CD | 2845.53(360.83) |
| | (SBE)$_{4.6}$-Et$_{5.9}$-β-CD | 3260.6(568) |
| | (SBE)$_{4.6}$-Et$_{7.9}$-β-CD | 1480(101) |
| Nimodipine | (SBE)$_{6.5}$-β-CD | 717.9(24) |
| | (SBE)$_{4.6}$-β-CD | 679.75(106) |
| | SBE)$_{4.6}$-β-Et$_{3.5}$-CD | 4197.6(376) |
| | (SBE)$_{4.6}$-Et$_{5.9}$-β-CD | 5175.8(560) |
| | (SBE)$_{4.6}$-Et$_{7.9}$-β-CD | 4686(407) |
| Clotrimazole | (SBE)$_{6.5}$-β-CD | 604.8(98) |
| | (SBE)$_{4.6}$-β-CD | 1905(45) |
| | (SBE)$_{4.6}$Et$_{3.5}$-β-CD | 535.4(101) |
| | (SBE)$_{4.6}$Et$_{5.9}$-β-CD | 935.01(208) |
| | (SBE)$_{4.6}$Et$_{7.9}$-β-CD | 734(154) |
| Triamcinolone | (SBE)$_{6.5}$-β-CD | 3030.1(181.1) |
| | (SBE)$_{4.6}$-β-CD | 818.19(60) |
| | (SBE)$_{4.6}$Et$_{3.5}$-β-CD | 2698.4(209) |
| | (SBE)$_{4.6}$Et$_{5.9}$-β-CD | 4177.2(301) |
| | (SBE)$_{4.6}$Et$_{7.9}$-β-CD | 821(120) |
| Carbamazepine | (SBE)$_{6.5}$-β-CD | 612(66) |
| Nitrendipine | (SBE)$_{6.5}$-β-CD | 1238(350) |
| | (SBE)$_{4.6}$-β-CD | 2040(105) |
| | SBE)$_{4.6}$-Et$_{3.5}$-β-CD | 5898.1(726) |
| | (SBE)$_{4.6}$-Et$_{6.5}$-β-CD | 7028(284) |
| | (SBE)$_{4.6}$-Et$_{8.5}$-β-CD | 2260(220) |

In the above tables, the value of "x" ranges from 3 to 9, and the value of "y" ranges from 2 to 10. Specific embodiments of the invention include those wherein x is greater than one, and y is greater than one.

In general, the value of "y" ranges from 1 to 3v+5. Where v=4 (α-CD), "y" can range in value from 1 to 17. Where v=5 (β-CD), "y" can range in value from 1 to 20. Where v=6 (γ-CD), "y" can range in value from 1 to 23. In general, "y" also ranges in value from 1 to 3v+z, where z ranges in value from 0 to 5. "y" may also range from 1 to 2v+z, or from 1 to 1v+z.

In general, the value of "x" ranges from 1 to 3v+5. Where v=4 (α-CD), "x" can range in value from 1 to 17. Where v=5 (β-CD), "x" can range in value from 1 to 20. Where v=6 (γ-CD), "x" can range in value from 1 to 23. In general, "x" ranges in value from 1 to 3v+z, where z ranges in value from 0 to 5. "x" may also range from 1 to 2v+z, or from 1 to 1v+z.

Among other uses, an SAE-AE-CD can be used to solubilize and/or stabilize a wide range of different materials and to prepare formulations for particular applications. The present cyclodextrin derivative may provide enhanced solubility and/or enhanced chemical, thermochemical, hydrolytic and/or photochemical stability of other ingredients in a composition. For example, an SAE-AE-CD may be used to stabilize an active agent in an aqueous medium. An SAE-AE-CD may also be used to increase the solubility of an active agent in an aqueous medium. For example, an increase in the binding constant for a particular active agent is observed upon conversion of an SAE-CD to an SAE-AE-CD.

Figure 7A:
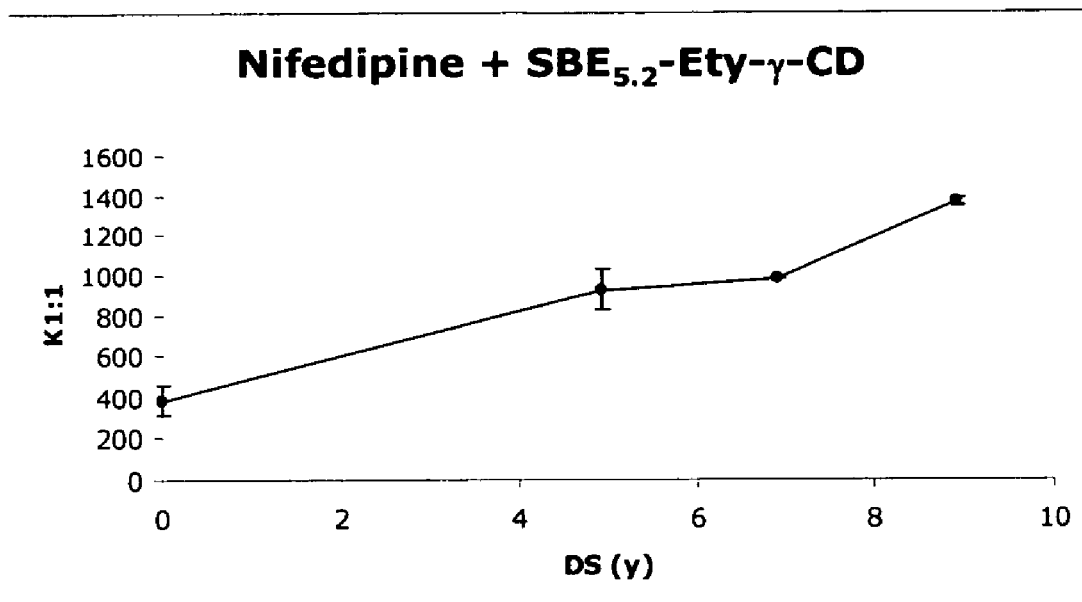
FIGS. 7a-7i depict charts containing the results of dissolution binding studies for SAE-AE-γ-CD's of the invention with various different drugs.
Figure 7B:
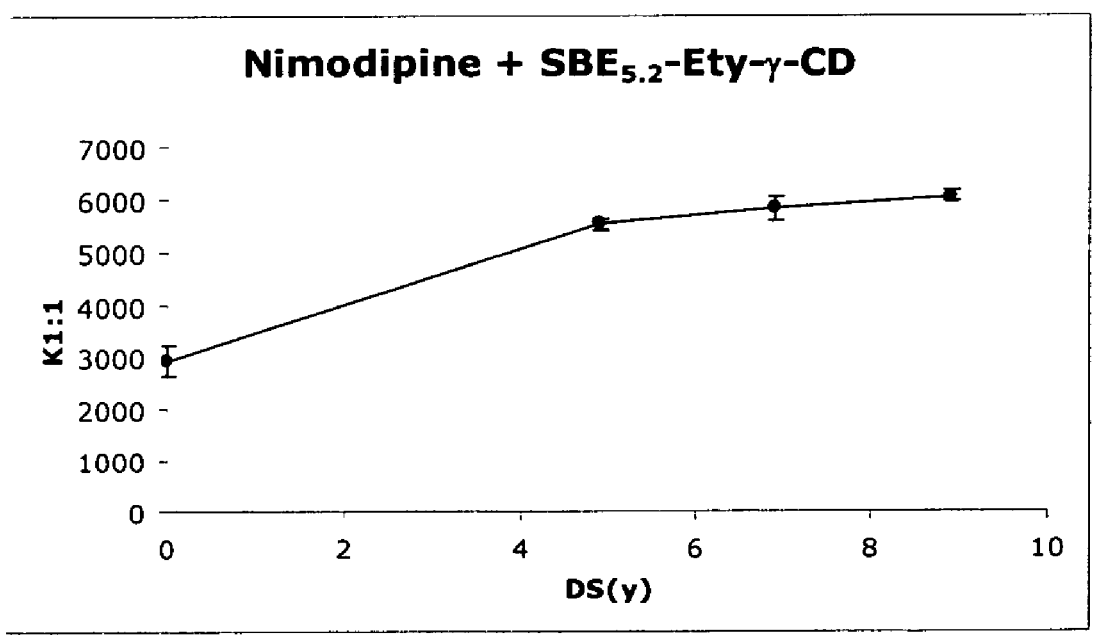
Figure 7C:
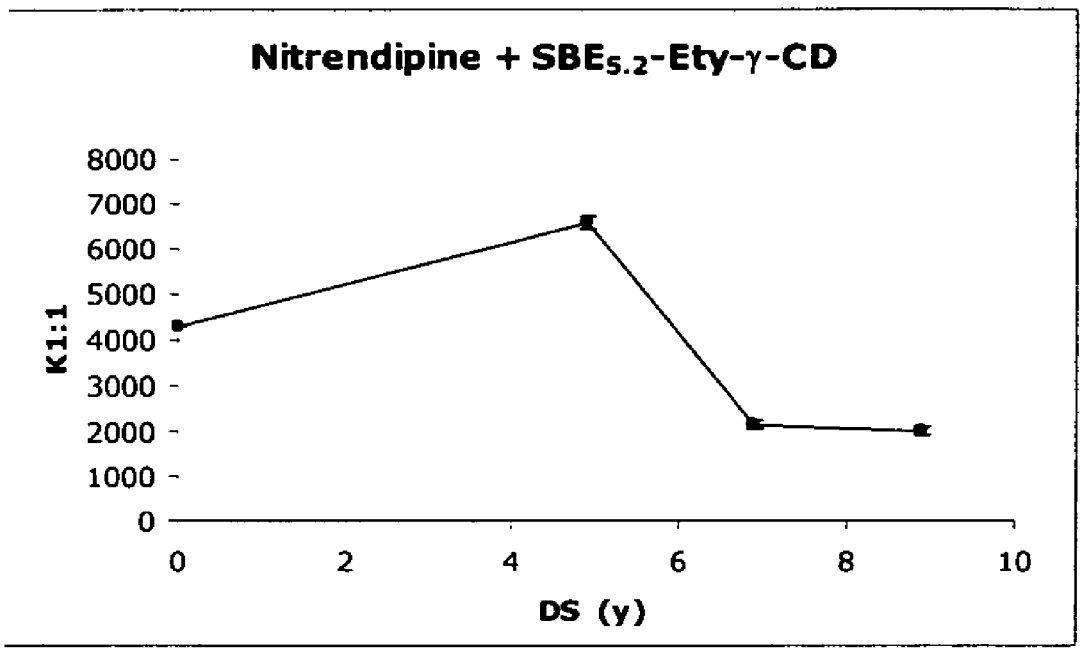
Figure 7D:
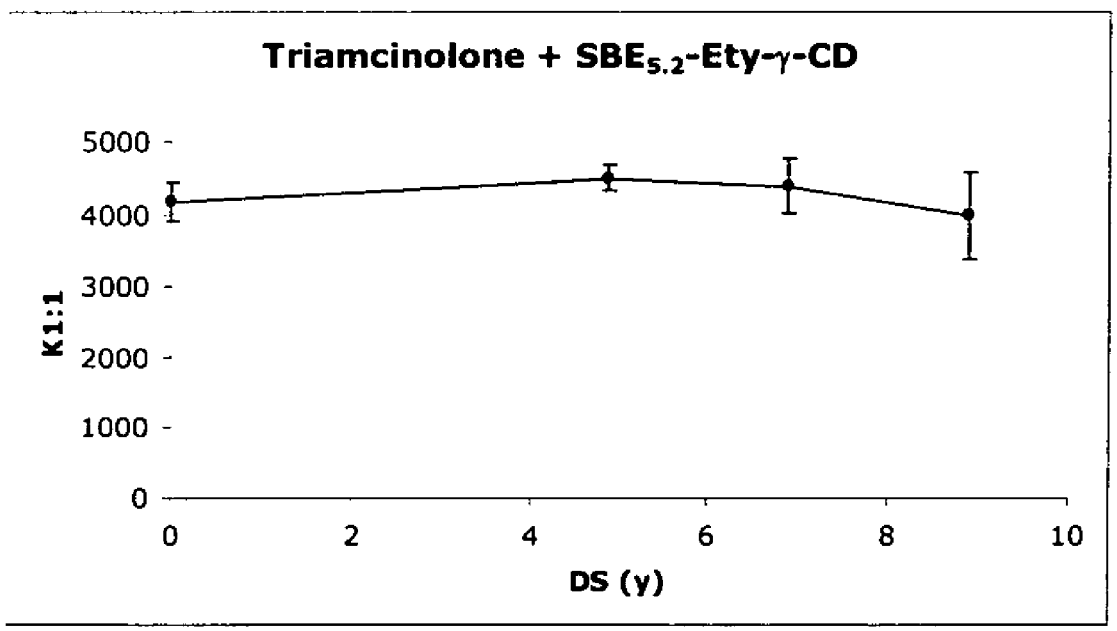
Figure 7E:
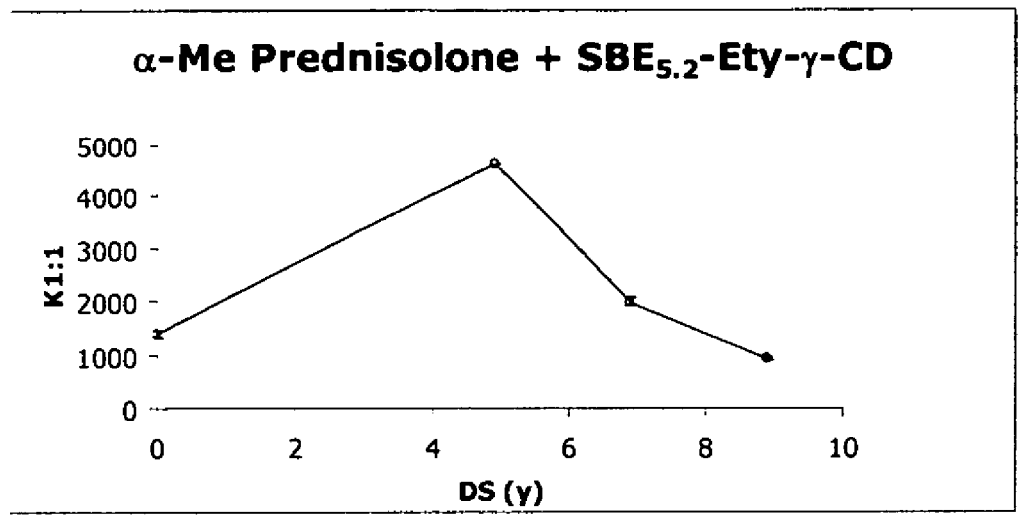
Figure 7F:
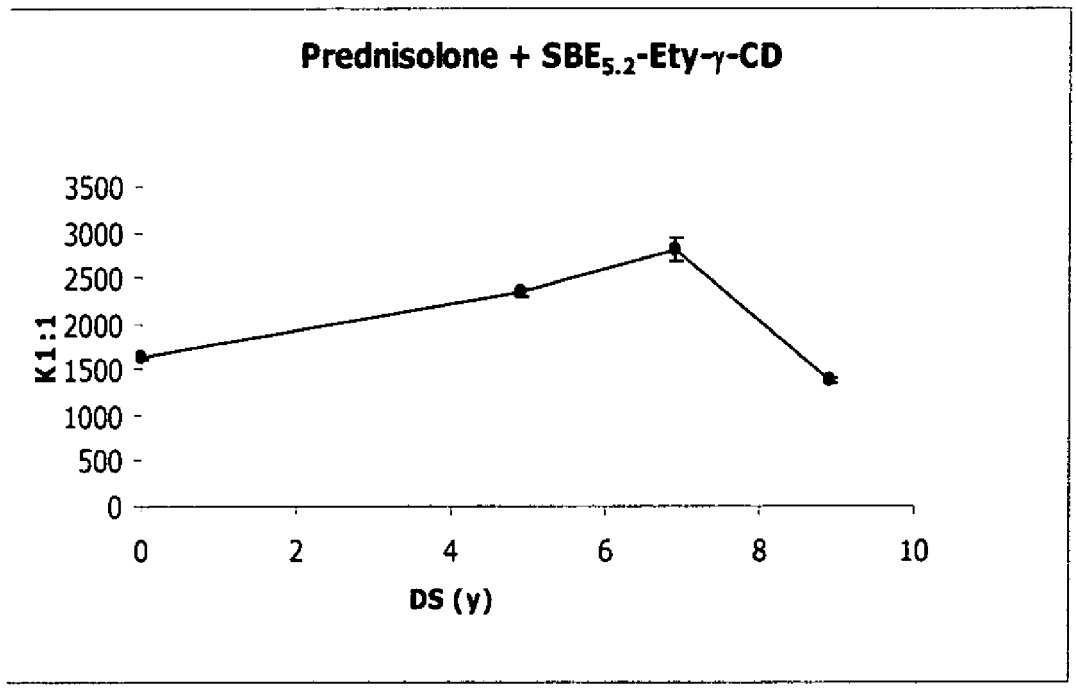
Figure 7G:
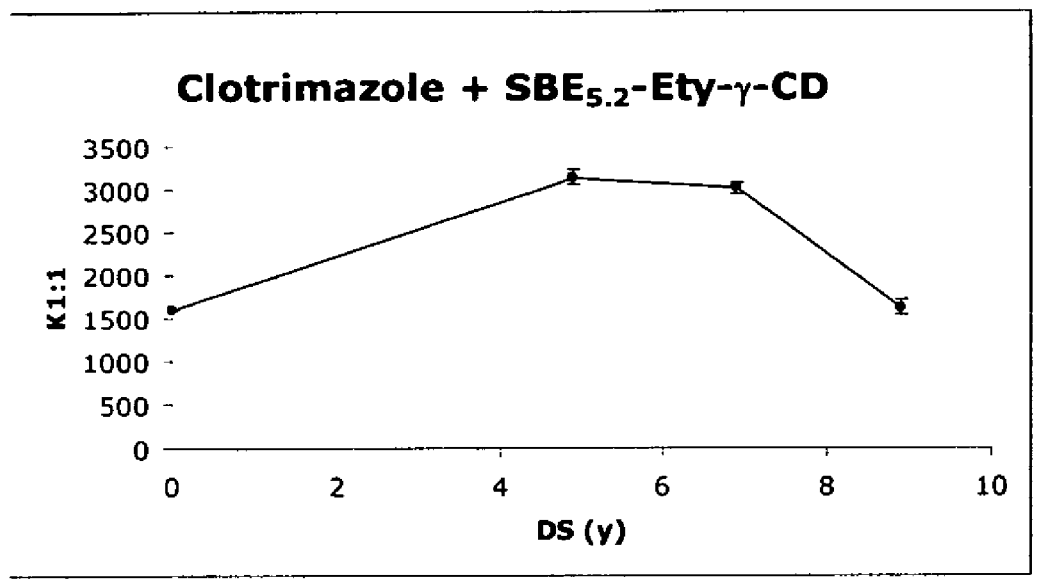
Figure 7H:
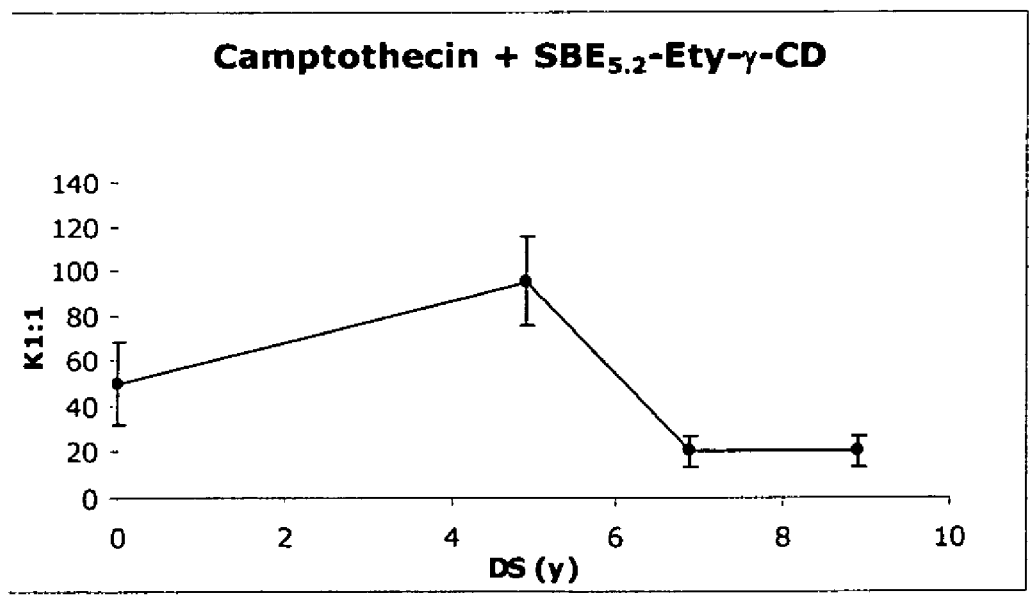
Figure 7I:
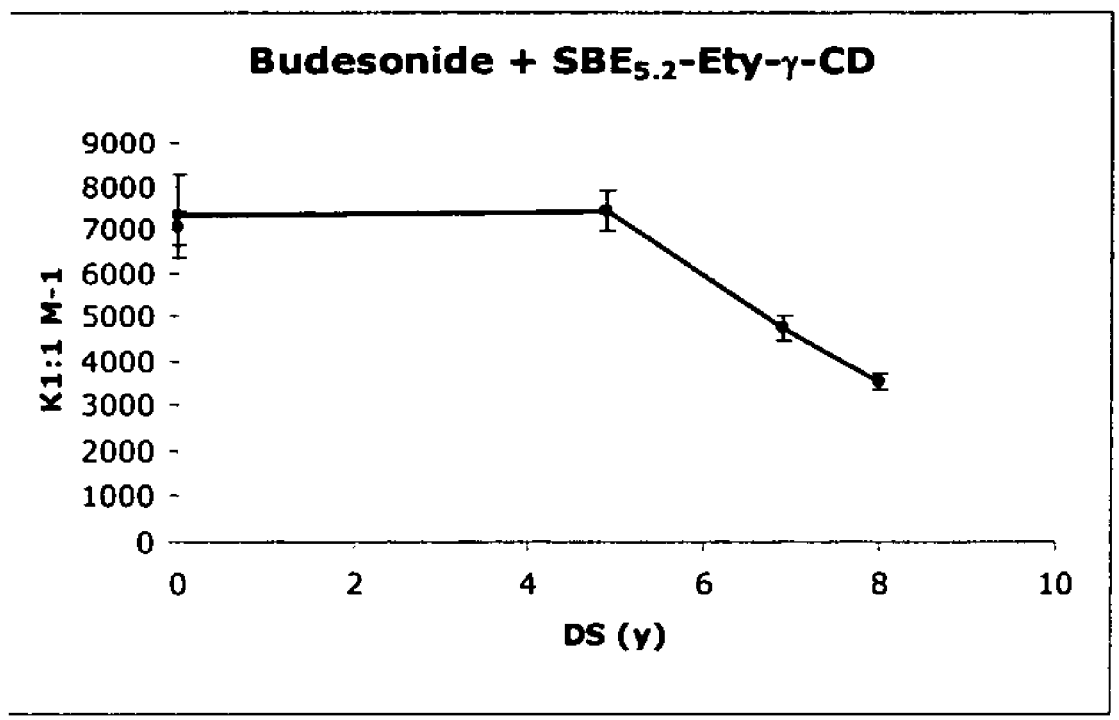
Figure 8A:
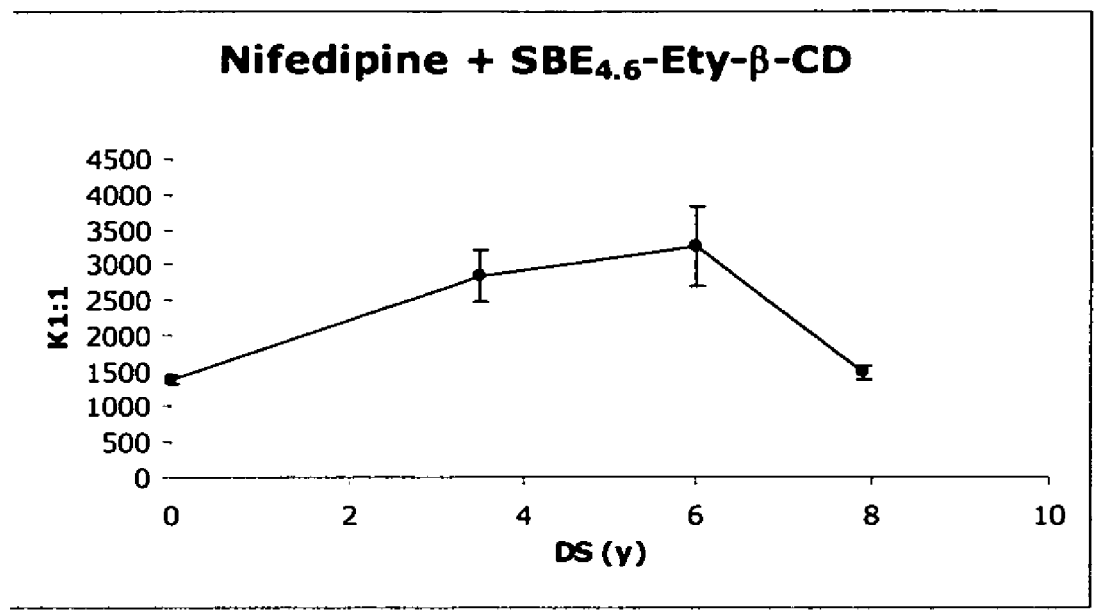
FIGS. 8a-8g depict charts containing the results of dissolution binding studies for SAE-AE-β-CD's of the invention with various different drugs.
Figure 8B:
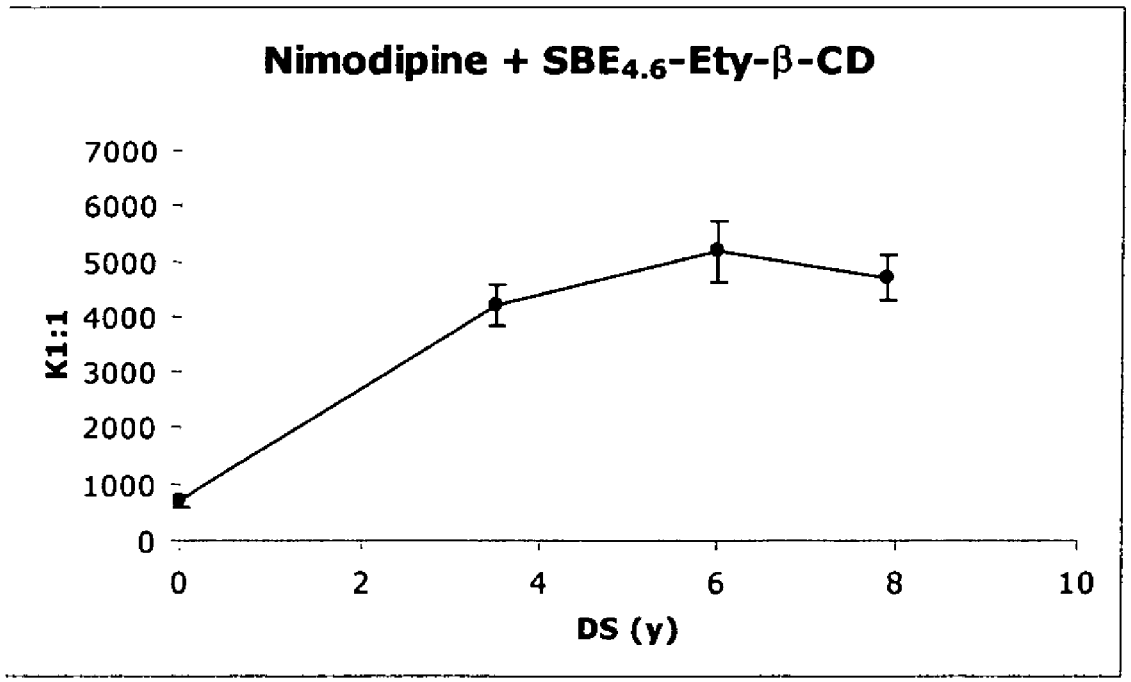
Figure 8C:
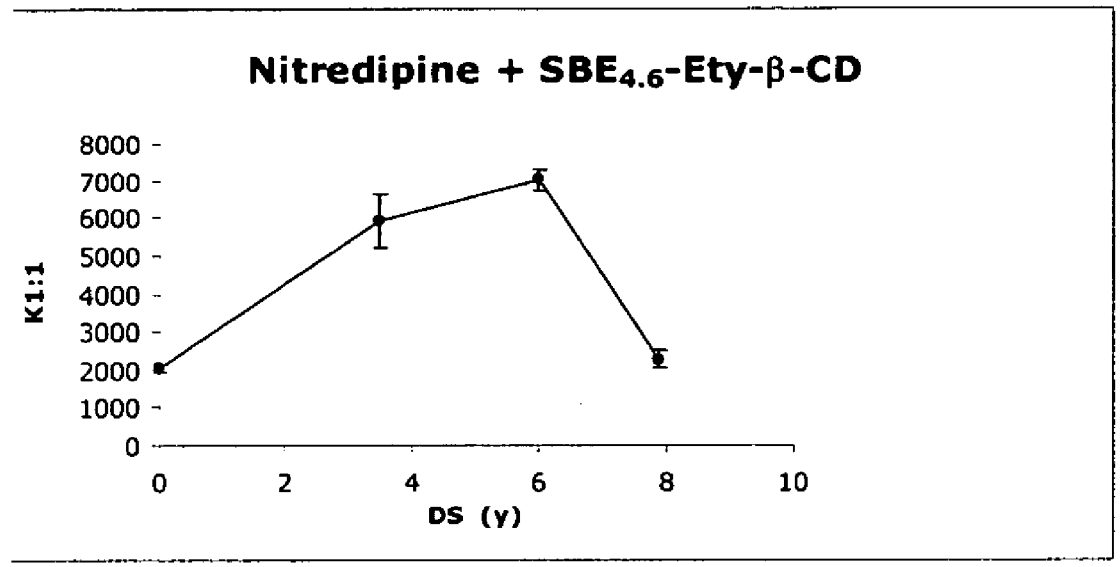
Figure 8D:
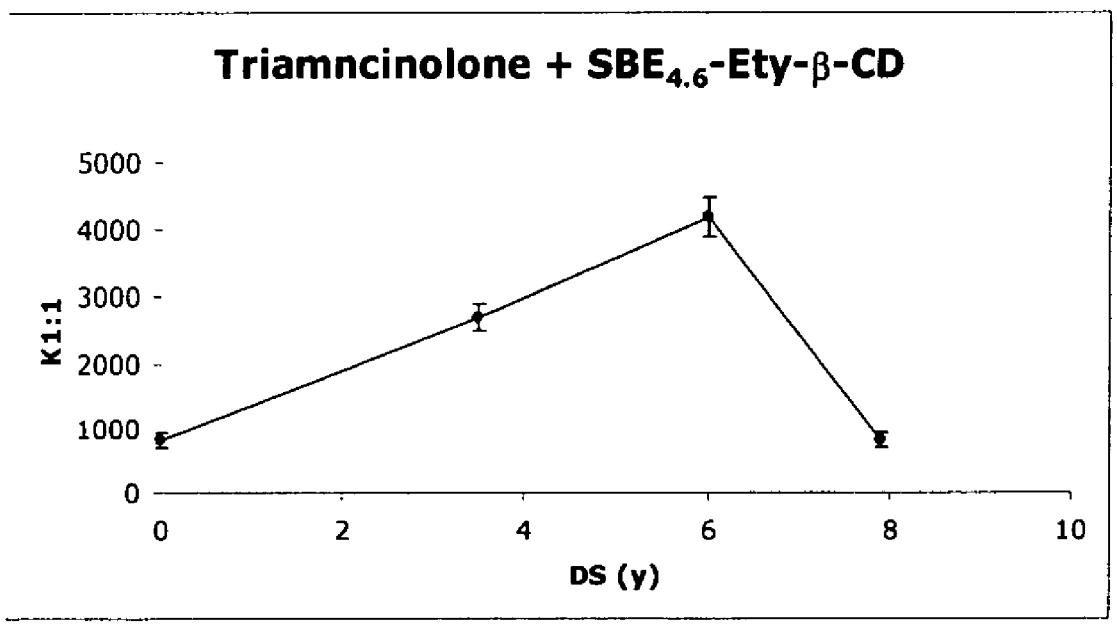
Figure 8E:
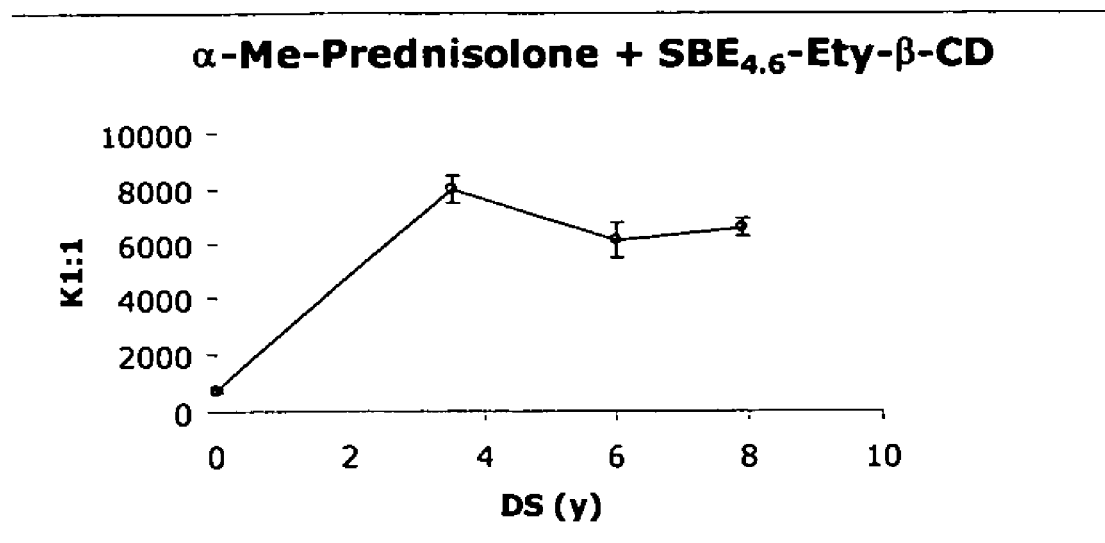
Figure 8F:
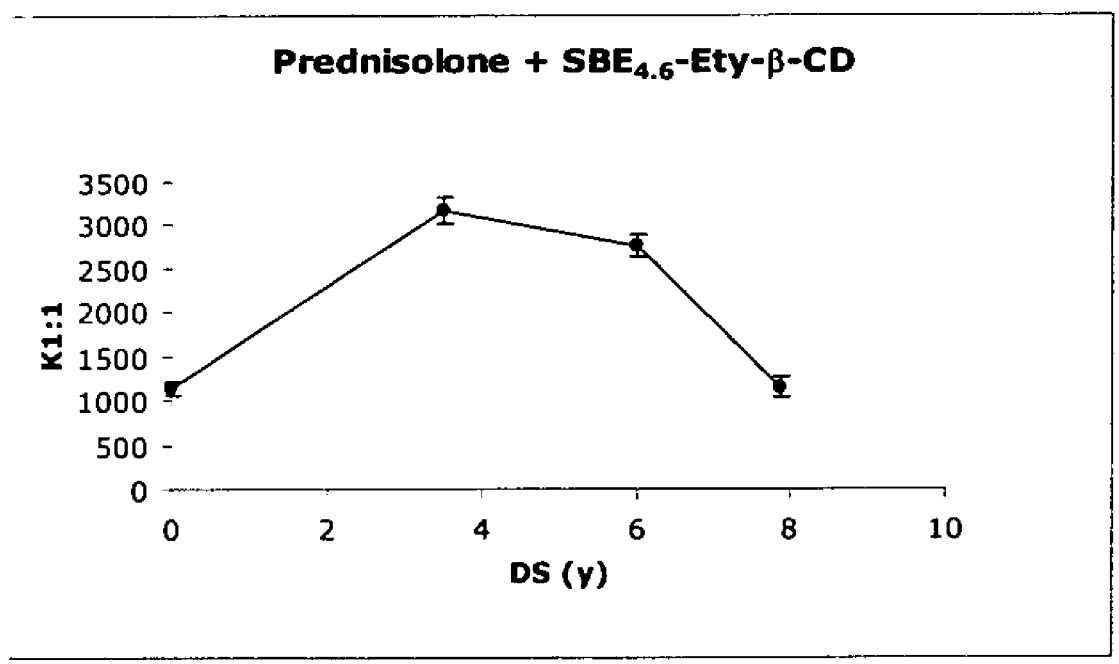
Figure 8G:
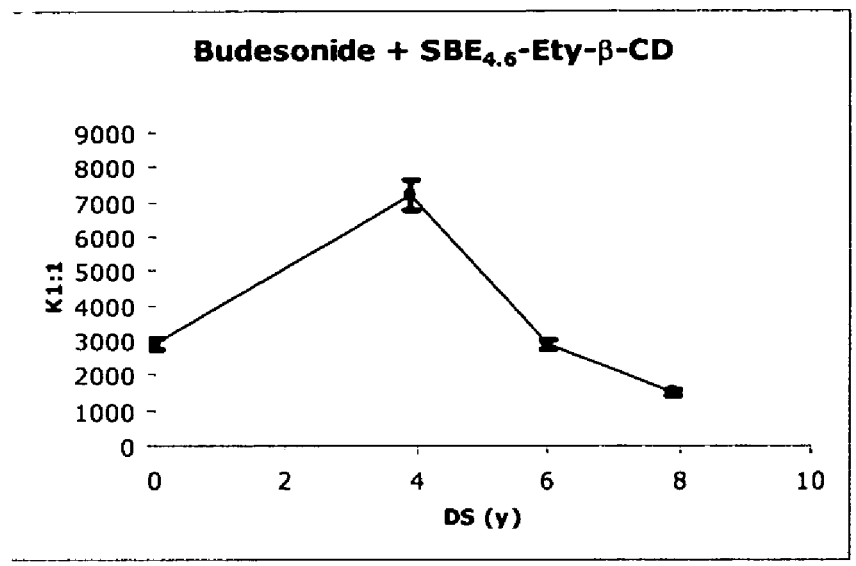

SAE-AE-CD's according to the invention were evaluated in terms of their ability to bind with different drugs as compared to the binding of the same drugs with structurally related SAE-CD's. FIGS. 7a-7h depict the results of binding studies of SAE-AE-γ-CD's with the drugs nifedipine (FIG. 7a), nimodipine (FIG. 7b), nitrendipine (FIG. 7c), triamcinolone (FIG. 7d), α-methyl-prednisolone (FIG. 7e), prednisolone (FIG. 7f), clotrimazole (FIG. 7g), camptothecin (FIG. 7h), and Budesonide (FIG. 7i). The binding constant of each SAE-AE-CD derivative with each drug was determined. The data are expressed in terms of DS (y) for ethylation (i.e., for SBEx-Ety-γ-CD) versus the observed binding constant for the above-mentioned drugs. In a similar fashion, FIGS. 8a-8f depict the results of binding studies of SAE-AE-β-CD's with the drugs nifedipine (FIG. 8a; SBE4.6-Ety-β-CD, where y=0, 3.5, 5.9, 7.9), nimodipine (FIG. 8b; SBE4.6-Ety-β-CD, where y=0. 3.5, 6.9, 8.9), nitrendipine (FIG. 8c; SBE4.6-Ety-β-CD, where y=0. 3.5, 6.9, 8.9), triamcinolone (FIG. 8d; SBE4.6-Ety-β-CD, where y=0. 3.5, 6.0, 8.9), α-methyl-prednisolone (FIG. 8e), prednisolone (FIG. 8f; SBE4.6-Ety-β-CD, where y=0. 3.5, 6.0, 7.9) and budesonide (FIG. 8g; SAE5.2-Ety-β-CD, where y=0. 4.9, 6.9, 8.9). In each of the figures, the SAE-AE-CD possesses improved binding (higher binding constant) to the above-mentioned drugs than does the structurally related SBE-CD. This apparently is true regardless of whether or not the cyclodextrin ring in the SAE-AE-CD is β-CD or γ-CD. In some embodiments, the high binding constants are observed when the DS (value for "y") for the Et (AE) substituent falls in the range of greater than 0 and less than or equal to about 10, about 1 to about 9, about 1 to about 9, or about 1 to about 8. The methyl and propyl ether derivatives, SAE-Me-CD and SAE-Pr-CD, respectively, may provide increased binding constants at "y" values similar to or different than the SAE-Et-CD.

The invention thus provides an SAEx-AEy-CD derivative having an increased binding constant for an active agent as compared to the binding constant of a structurally related SAE-CD with the same active agent. The invention also provides a method of increasing the binding constant of an SAEx-CD derivative for an active agent, the method comprising the step of derivatizing the SAEx-CD with an AE precursor to form an SAEx-AEy-CD having an increased binding constant for the active agent, wherein the SAEx-AEy-CD is optionally purified to remove unwanted materials.

The ring size of the parent CD and the degree of substitution and the length of the alkyl ether substituent can each have an effect upon the cyclodextrin's ability to solubilize a compound. The effects can be balanced to provide SAE-AE-CD derivatives that solubilize compounds to a great extent. The following table details the observed solubility (mg/ml) for camptothecin in the presence of the indicated cyclodextrins, present at a concentration of about 50 mM in water.

| Cyclodextrin | Camptothecin solubility (mg/ml) |
|---|---|
| Control (HP4.6-β-CD) | 0.022 |
| SBE4.6-β-CD | 0.025 |
| SBE4.6-Et6-β-CD | 0.025 |
| SBE4.6-Et8.5-β-CD | 0.028 |
| SBE5.2-γ-CD | 0.013 |
| SBE5.2-Me3.2-γ-CD | 0.013 |
| SBE5.2-Et3.9-γ-CD | 0.009 |
| SBE5.2-Et4.9-γ-CD | 0.012 |
| SBE5.2-Et8.9-γ-CD | 0.028 |

Figure 9:
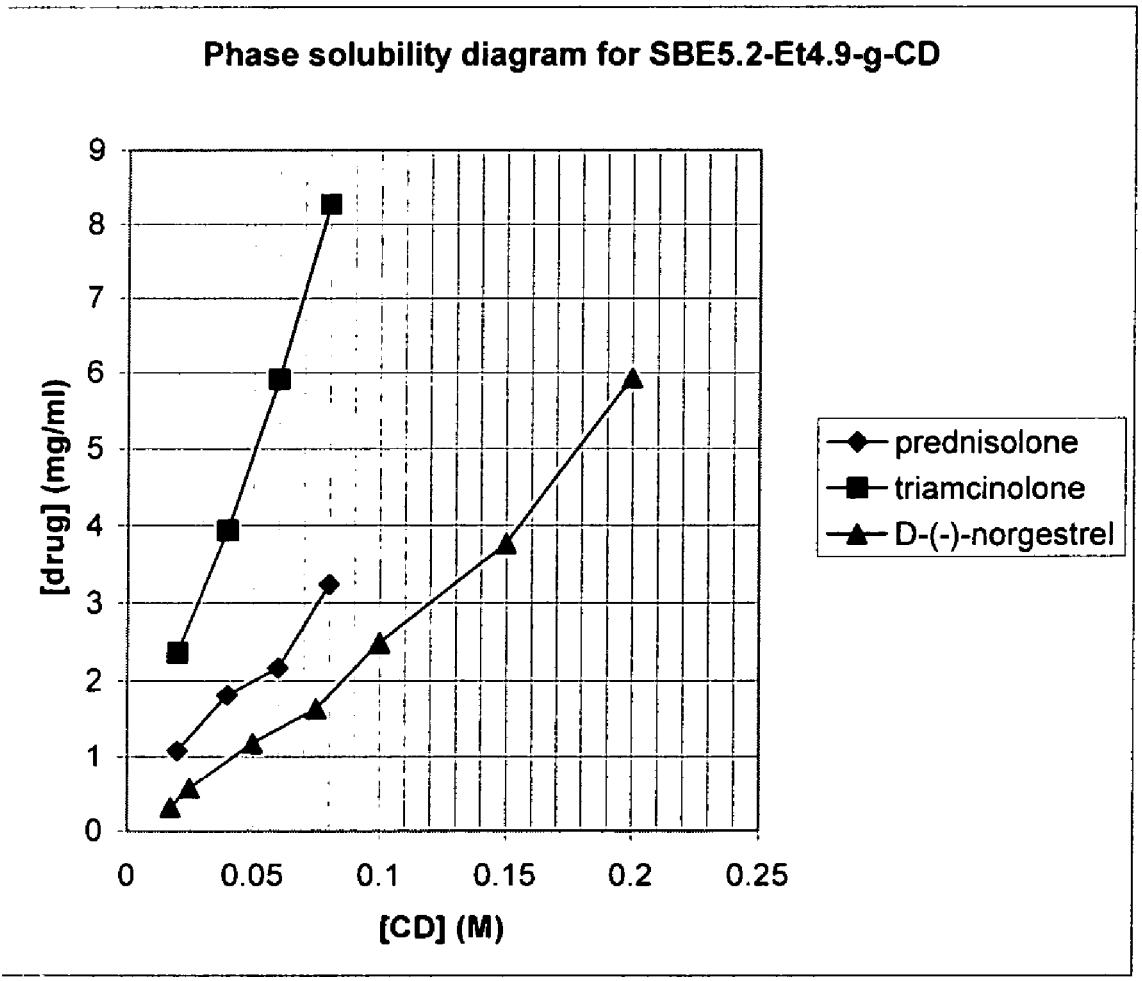
FIG. 9 depicts a phase solubility diagram for one SAE-AE-CD derivative and the drugs triamcinolone, prednisolone, and D-(−)-norgestrel.

It is well known that different CD derivatives possess different affinities with drugs that vary in structure. FIG. 9 depicts a phase solubility diagram for the derivative SBE5.2-Et4.9-γ-CD and the drugs triamcinolone, prednisolone, and D-(−)-norgestrel. This derivative behaves differently with each of the three drugs. The key structural difference between the drugs is the structure of the pendant side-chain at position 17.

Figure 10:
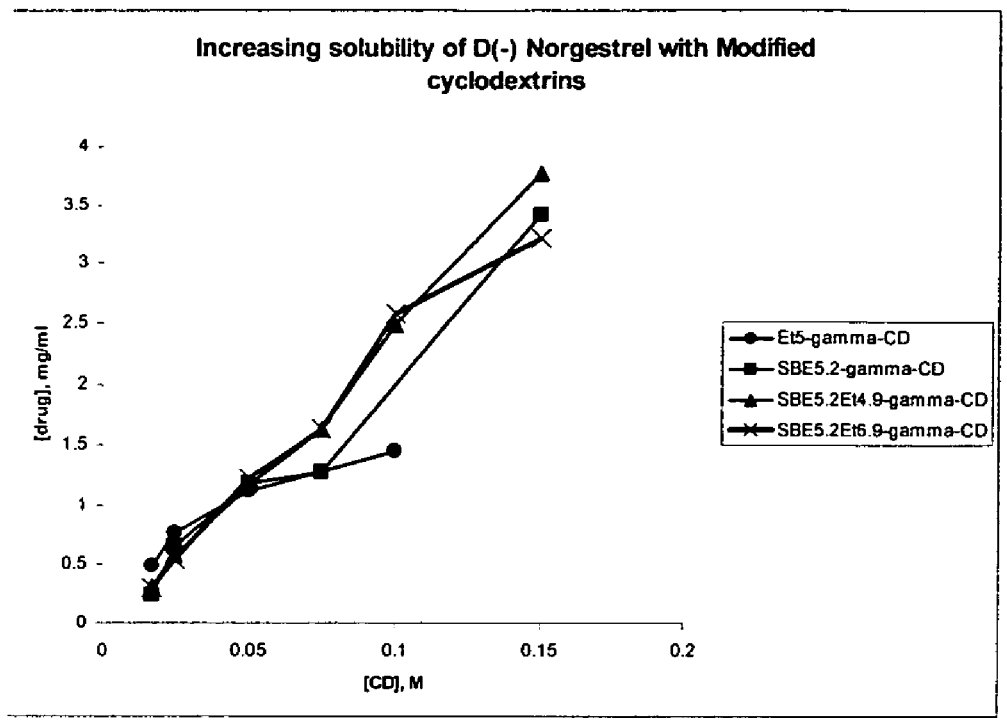
FIG. 10 depicts a phase solubility diagram for several different CD derivatives and the drug D-(−)-norgestrel.

FIG. 10 depicts a phase solubility diagram for the drug D-(−)-norgestrel and the following CD's: 1) γ-CD; 2) Et5.1-γ-CD; 3) SBE5.2-γ-CD; 4) SBE5.2-Et4.9-γ-CD; and 5) SBE5.2-Et6.9-γ-CD. The binding of γ-CD with norgestrel is improved by derivatization with an ethyl moiety and even more by derivatization with a sulfobutyl moiety. However, the combined derivatization, i.e. ethyl and sulfobutyl, provides an unexpectedly greater improvement in binding (see SBE5.2-Et4.9-γ-CD). Increasing the degree of substitution of the ethyl moiety provides even better binding with norgestrel (see SBE5.2-Et-6.9-γ-CD).

Figure 11:
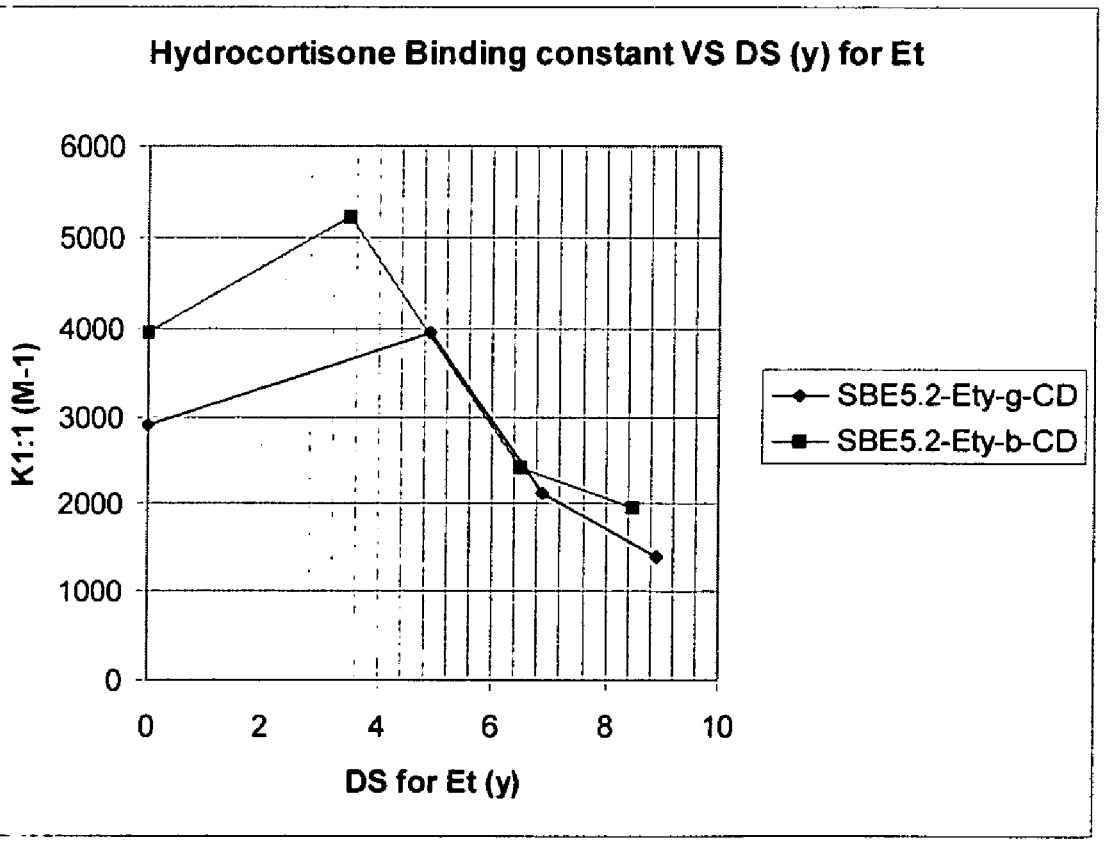
FIG. 11 depicts a chart showing the relationship between the binding constant for hydrocortisone and SAE-AE-CD and the degree of substitution for the derivatives SAE-AE-γ-CD and SAE-AE-β-CD.

FIG. 11 depicts a chart showing the relationship between the binding constant for hydrocortisone and SAE-AE-CD and the degree of substitution for the derivatives SAE-AE-γ-CD and SAE-AE-β-CD. The SBE-γ-CD has a lower binding constant for hydrocortisone than does SBE-β-CD indicating that the former has greater solubilizing power. As the degree of substitution (DS; y) for the ethyl ether substituent (Et) for SBE5.2-Ety-β-CD increases from 0 to 4.9, the binding constant increases significantly. However, further increasing the DS to 6.9 or 8.9 dramatically reduces the binding constant. Aside from the already lower affinity that SBE5.2-γ-CD already has for hydrocortisone, increasing the DS for the Et to 4.9, 6.9 or 8.9 also causes an initial increase and a subsequent decrease in the binding constant. The SAE-AE-CD possesses an optimal DS for the Et substituent when binding to hydrocortisone.

Figure 12:
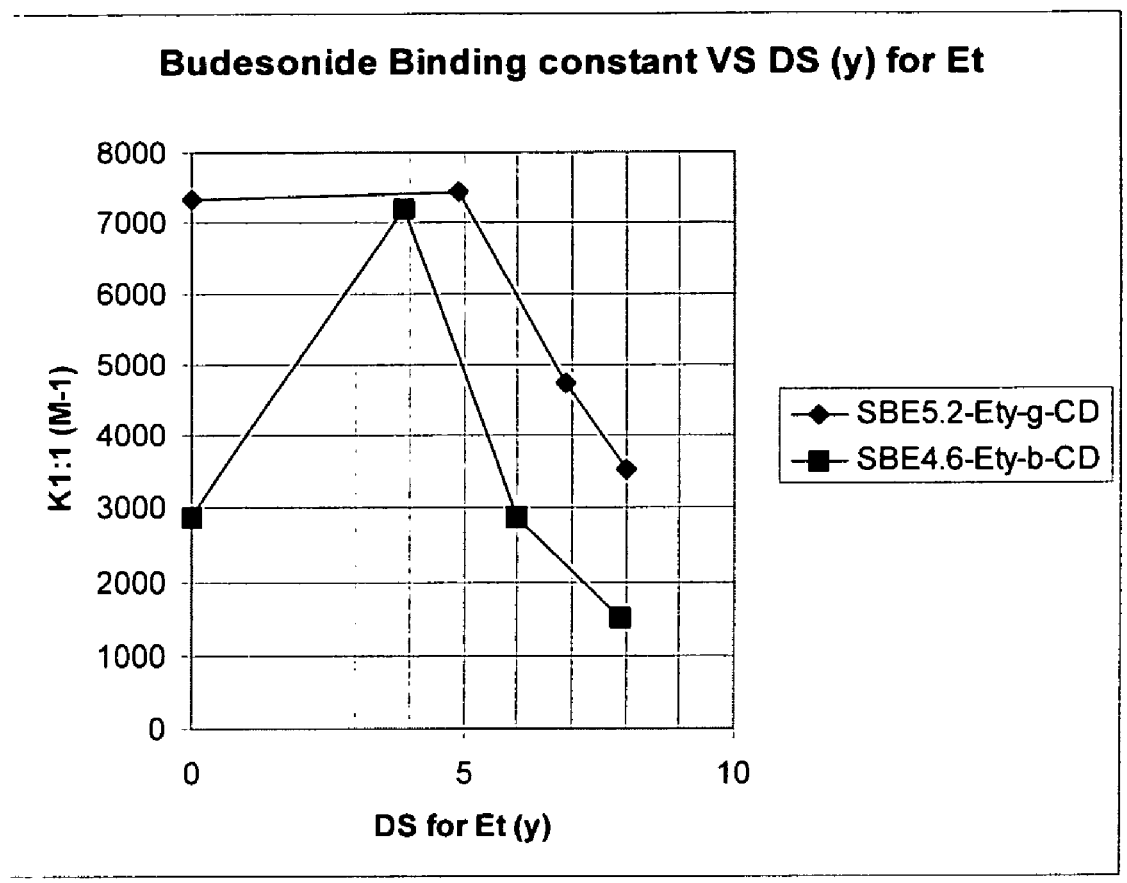
FIG. 12 depicts a chart showing the relationship between the binding constant for budesonide and SAE-AE-CD and the degree of substitution for the derivatives SAE-AE-γ-CD and SAE-AE-β-CD.

FIG. 12 depicts a chart showing the relationship between binding constant for budesonide and SAE-AE-CD and the degree of substitution for the derivatives SAE-AE-γ-CD and SAE-AE-β-CD. The SBE-β-CD has a lower binding constant for budesonide than does SBE-β-CD indicating that the former has greater solubilizing power. As the degree of substitution (DS; y) for the ethyl ether substituent (Et) for SBE4.6-Ety-β-CD increases from 0 to 3.5, the binding constant increases dramatically. However, further increasing the DS to 6.5 or 8.5 dramatically reduces the binding constant. Aside from the already high affinity that SBE5.2-γ-CD already has for budesonide, increasing the DS for the Et to 4.9, 6.9 or 8.9 also causes an initial increase and a subsequent decrease in the binding constant. The SAE-AE-CD possesses an optimal DS for the Et substituent when binding to budesonide.

Figure 13:
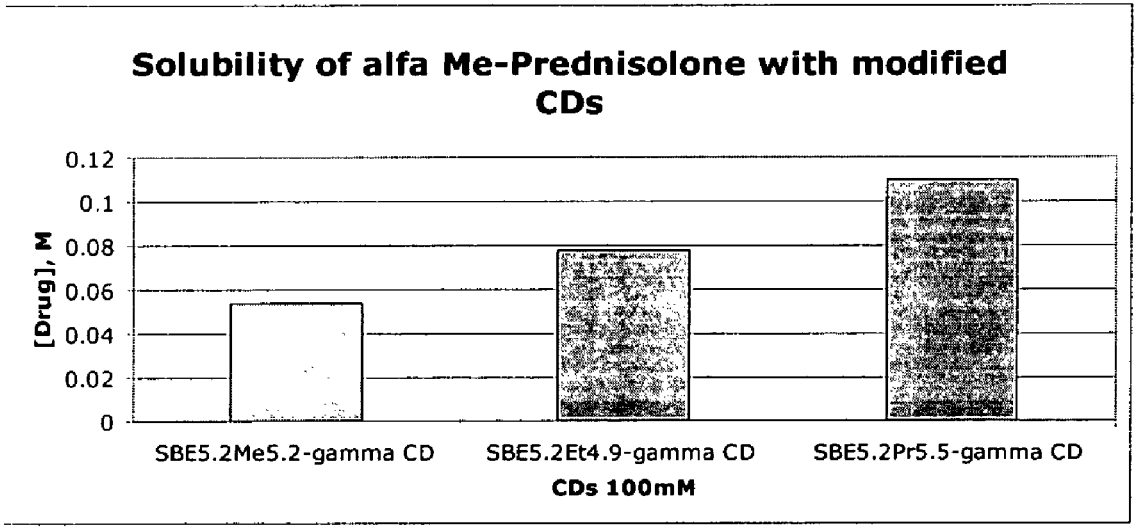
FIG. 13 depicts a chart of the change in maximum solubility of α-methyl prednisolone with respect to the alkyl chain length of the AE substituent in the γ-CD cyclodextrin derivatives with a DS for SBE chain of 5.2 and a DS for AE chain between 4-and 6.

A direct observation of the effect that chain length of the alkyl ether substituent might have on the solubilizing power of a CD is depicted in FIG. 13, which depicts the maximum concentration of α-methyl prednisolone dissolved in the presence of the same concentration (100 mM) of cyclodextrin derivative. For this model drug, increasing the chain length of the alkyl ether substituent increasing the binding affinity (binding constant) of the CD derivative for the drug. For example, for SBE5.2-AE5-γ-CD, changing the AE substituent from Me to Et to Pr results in a corresponding increasing in the solubilizing power for α-methyl prednisolone.

Figure 14:
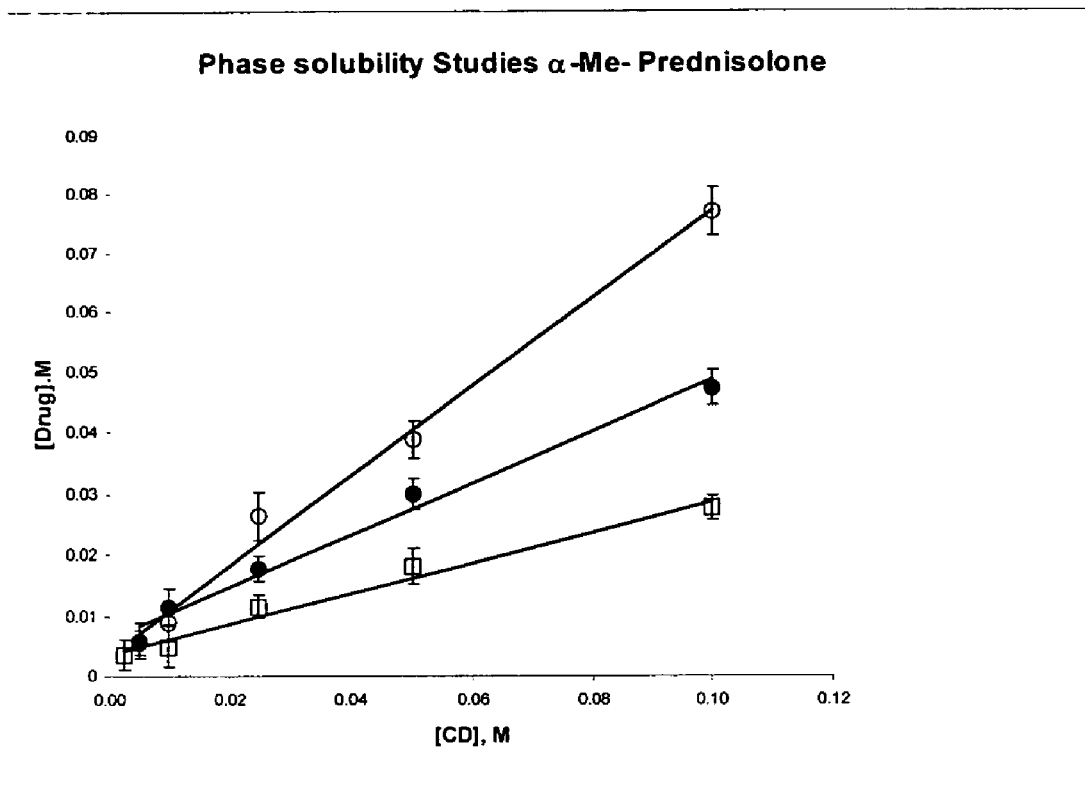
FIG. 14 depicts a phase solubility diagram for α-methyl prednisolone and three CD's: CAPTISOL™ (SBE6.5-β-CD), SBE5.2-γ-CD and SBE5.2-Et4.9-γ-CD.

FIG. 14 depicts a phase solubility diagram for α-methyl prednisolone and three CD's: CAPTISOL™ (SBE7-β-CD), SBE5.2-γ-CD and SBE5.2-Et4.9-γ-CD. The data indicates that the γ-CD ring binds more favorably with the drug than does the β-CD ring; however, conversion of the SBE5.2-γ-CD to SBE5.2-Et4.9-γ-CD results in even better binding with the drug.

The binding of paclitaxel (TAXOL®) with HP-β-CD, SBE4-β-CD, SBE4.6-Et6-β-CD, SBE4.6-Et8.5-β-CD, CAPTISOL®, SBE5.2-γ-CD, SBE5.2-Me3.2-γ-CD, SBE5.2-Et3.5-γ-CD, SBE45.2-Et4.9-γ-CD and SBE5.2-Et8.9-γ-CD was evaluated as follows. Stock solutions containing CD (10 mM or 50 mM, water, pH 4.5) were prepared and divided into portions. Excess amount of drug was added to the CD solutions that were then vortexed, sonicated for 5 minutes and equilibrated at 25° C. for 24 hours, after which equilibrium was reached. The solutions were centrifuged, and the concentration of drug in each supernatant was measured by HPLC after 1 and 5 days. The stability of paclitaxel in the presence of cyclodextrins, stored at 4° C. after 5 days of preparation was measured. The concentration of paclitaxel for solubility experiments was calculated based on a calibration curve obtained using an HPLC method interfaced with UV/Vis detector. The data is summarized in the table below.

| | 10 mM (CD) | | 50 mM (CD) | |
|---|---|---|---|---|
| CD (10 mM) | Taxol (μg/ml) 1 day | Taxol (μg/ml) 5 days | Taxol (μg/ml) 1 day | Taxol (μg/ml) 5 days |
| HP-β-CD | 1.94 | 1.47 | 14.35 | 14.89 |
| SBE4-β-CD | 3.25 | 1.08 | 9.39 | 10.11 |
| SBE4.6-Et6-β-CD | 1.68 | 2.01 | 17.32 | 16.15 |
| SBE4.6-Et8.5-β-CD | 2.27 | 2.81 | 13.71 | 13.29 |
| Captisol | 1.04 | 1.03 | 14.12 | 13.33 |
| SBE5.2-γ-CD | 0.96 | 1.44 | 8.14 | 7.73 |
| SBE5.2-Me3.2-γ-CD | 1.34 | 1.92 | 13.81 | 12.90 |
| SBE5.2-Et3.5-γ-CD | 3.53 | 3.74 | 20.06 | 18.36 |
| SBE5.2-Et4.9-γ-CD | 2.96 | 4.10 | 16.31 | 17.64 |
| SBE5.2-Et8.9-γ-CD | 7.29 | 7.52 | 40.29 | 40.18 |

Of the cyclodextrins tested, SBE5.2-Et8.9-γ-CD was found to be the best at solubilizing paclitaxel. Accordingly, the solubility of paclitaxel in the presence of SBE5.2-Et8.9-γ-CD was determined.

Figure 15:
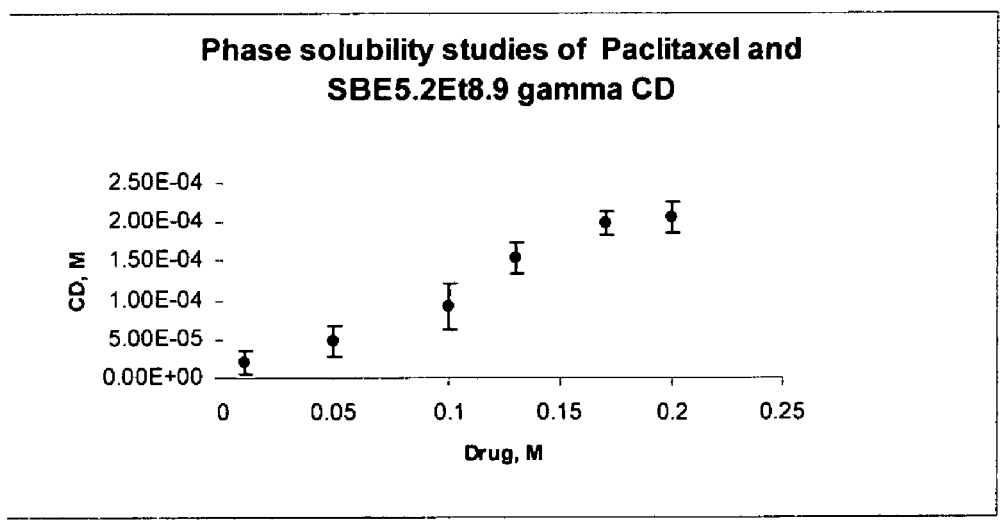
FIG. 15 depicts a phase solubility diagram for SBE5.2Et8.9Gamma CD derivative and the drug paclitaxel.
Figure 16:
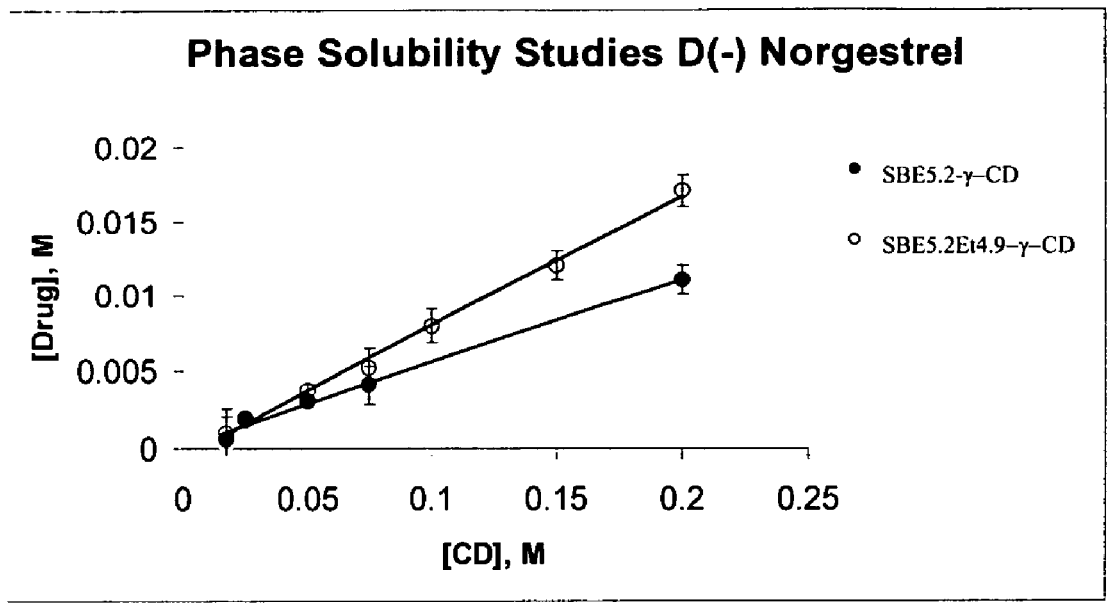
FIG. 16 depicts a phase solubility diagram two different CD derivatives and the drug D-(−)-norgestrel.
Figure 17:
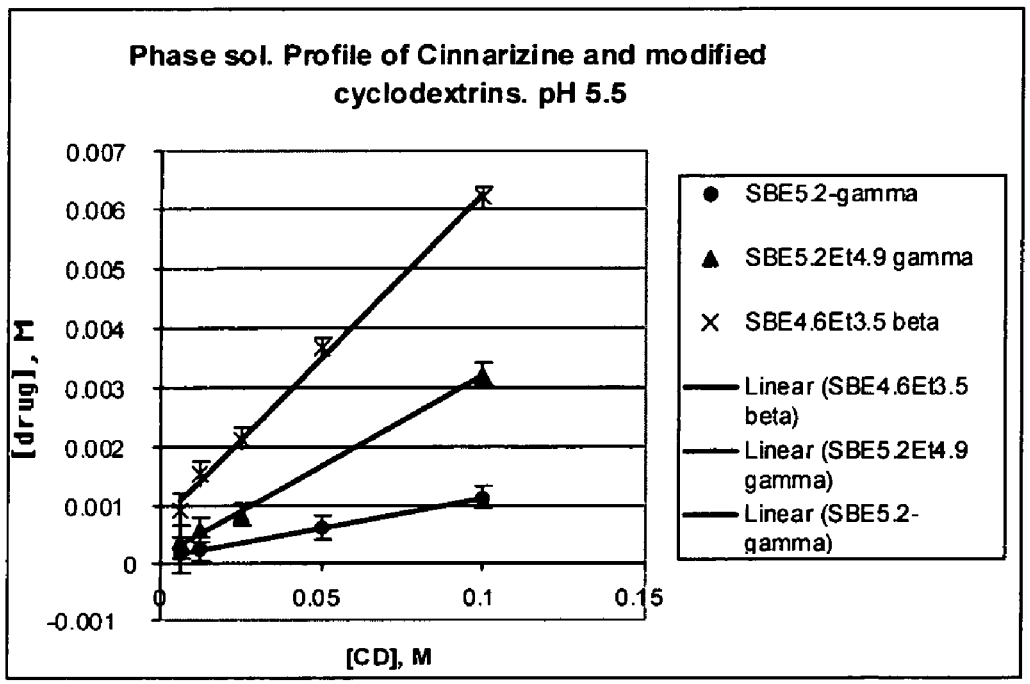
FIG. 17 depicts a phase solubility diagram for several different CD derivatives and the drug Cinnarizine.

The phase solubility diagram is detailed in FIG. 15. Similar analyses were conducted with docetaxel (TAXOTERE®) and SBE5.2-Et8.9-γ-CD and SBE5.2-Et4.9-γ-CD. The data taken at 25° C. after vortexing, sonication and equilibration for 24 hours are summarized in the table below.

| CDs | Max solubility of docetaxel (mg/ml) At (CD) = 10 mM | Max solubility of docetaxel (mg/ml) At (CD) = 50 mM | $K (M^{-1})$ docetaxel |
|---|---|---|---|
| SBE5.2-Et4.9-γ-CD | 0.022 | 0.066 | 115 |
| SBE5.2-Et8.9-γ-CD | 0.025 | 0.098 | 200 |

It is evident that the simultaneous presence of an AE and SAE chain on the same CD ring improves the binding potential of the parent CD or of an AE-CD and SAE CD.

The binding potential of all tested molecules varied with the DS (y) of the CD derivatives. The variability is not present only in molecules with different structure but also in molecules with similar structure, e.g. nimodipine, nitrendipine and nifedipine.

The formulation of the invention can include one or more active agents. The active agent included in the present invention can possess a wide range of values for water solubility, bioavailability and hydrophilicity. Active agents to which the present invention is particularly suitable include water insoluble, poorly water soluble, slightly water soluble, moderately water soluble, water soluble, very water soluble, hydrophobic, or hydrophilic therapeutic agents. It will be understood by the artisan of ordinary skill that an active agent used in the formulation of the present invention is independently selected at each occurrence from any known active agent and from those disclosed herein. It is not necessary that the active agent complex with the derivatized cyclodextrin or form an ionic association with the derivatized cyclodextrin.

Active agents generally include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents, pharmaceutically effective active agents, and other such compounds for pharmaceutical, veterinary, horticultural, household, food, culinary, agricultural, cosmetic, industrial, cleaning, confectionery and flavoring applications. The active agent can be present in its neutral, ionic, salt, basic, acidic, natural synthetic, diastereomeric, isomeric, enantiomerically pure, racemic, hydrate, chelate derivative, analog, or other common form.

Representative pharmaceutically effective active agents include nutrients and nutritional agents, hematological agents, endocrine and metabolic agents, cardiovascular agents, renal and genitourinary agents, respiratory agents, central nervous system agents, gastrointestinal agents, anti-infective agents, biologic and immunological agents, dermatological agents, ophthalmic agents, antineoplastic agents, and diagnostic agents. Exemplary nutrients and nutritional agents include as minerals, trace elements, amino acids, lipotropic agents, enzymes and chelating agents. Exemplary hematological agents include hematopoietic agents, anti-platelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous cysteamine bitartrate, sodium benzoate and sodium phenylacetate, bromocriptine mesylate, cabergoline, agents for gout, and antidotes.

Exemplary cardiovascular agents include nootropic agents, antiarrhythmic agents, calcium channel blocking agents, vasodilators, antiadrenergics/sympatholytics, renin angiotensin system antagonists, antihypertensive agent combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, respiratory inhalant products, nasal decongestants, respiratory enzymes, lung surfactants, antihistamines, nonnarcotic antitussives, and expectorants. Exemplary central nervous system agents include CNS stimulants, narcotic agonist analgesics, narcotic agonist-antagonist analgesics, central analgesics, acetaminophen, salicylates, nonnarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, injectable local anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including H pylori agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, cephalosporins and related antibiotics, carbapenem, monobactams, chloramphenicol, quinolones, fluoroquinolones, tetracyclines, macrolides, spectinomycin, streptogramins, vancomycin, oxalodinones, lincosamides, oral and parenteral aminoglycosides, colistimethate sodium, polymyxin b sulfate, bacitracin, metronidazole, sulfonamides, nitrofurans, methenamines, folate antagonists, antifungal agents, antimalarial preparations, antituberculosis agents, amebicides, antiviral agents, antiretroviral agents, leprostatics, antiprotozoals, anthelmintics, and cdc anti-infective agents. Exemplary biologic and immunological agents including immune globulins, monoclonal antibody agents, antivenins, agents for active immunization, allergenic extracts, immunologic agents, and antirheumatic agents. Exemplary dermatological agents include topical antihistamine preparations, topical anti-infectives, anti-inflammatory agents, anti-psoriatic agents, antiseborrheic products, arnica, astringents, cleansers, capsaicin, destructive agents, drying agents, enzyme preparations, topical immunomodulators, keratolytic agents, liver derivative complex, topical local anesthetics, minoxidil, eflornithine HCl, photochemotherapy agents, pigment agents, topical poison ivy products, topical pyrimidine antagonist, pyrithione zinc, retinoids, rexinoids, scabicides/pediculicides, wound healing agents, emollients, protectants, sunscreens, ointment and lotion bases, rubs and liniments, dressings and granules, and physiological irrigating solutions. Exemplary ophthalmic agents include agents for glaucoma, mast cell stabilizers, ophthalmic antiseptics, ophthalmic phototherapy agents, ocular lubricants, artificial tears, ophthalmic hyperosmolar preparations, and contact lens products. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, dna topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

The above-mentioned list should not be considered exhaustive and is merely exemplary of the many embodiments considered within the scope of the invention. Many other active agents can be administered with the formulation of the present invention.

The formulation of the invention can be used to deliver two or more different active agents. Particular combinations of active agents can be provided by the present capsule. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein.

An active agent contained within the present formulation can be present as its pharmaceutically acceptable salt. As used herein, "pharmaceutically acceptable salt" refers to derivatives of the disclosed compounds wherein the active agent is modified by reacting it with an acid or base as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic., isethionic, and others known to those of ordinary skill in the art. The pharmaceutically acceptable salts of the present invention can be synthesized from the parent active agent which contains a basic or acidic moiety by conventional chemical methods. Lists of other suitable salts are found in *Remington's Pharmaceutical Sciences*, 17$^{th}$. ed., Mack Publishing Company, Easton, Pa., 1985, the relevant disclosure of which is hereby incorporated by reference.

The SAE-AE-CD need not bind with another material, such as an active agent present in a formulation containing it. However, if an SAE-AE-CD binds with another material, such a bond can be formed as a result of inclusion complexation, ion pair formation, hydrogen bonding, and/or Van der Waals bonding.

An anionic derivatized cyclodextrin can complex or otherwise bind with an acid-ionizable agent. As used herein, the term acid-ionizable agent is taken to mean any compound that becomes or is ionized in the presence of an acid. An acid-ionizable agent comprises at least one acid-ionizable functional group that becomes ionized when exposed to acid or when placed in an acidic medium. Exemplary acid-ionizable functional groups include a primary amine, secondary amine, tertiary amine, quaternary amine, aromatic amine, unsaturated amine, primary thiol, secondary thiol, sulfonium, hydroxyl, enol and others known to those of ordinary skill in the chemical arts.

The degree to which an acid-ionizable agent is bound by non-covalent ionic binding versus inclusion complexation formation can be determined spectrometrically using methods such as $^1$HNMR, $^{13}$CNMR, or circular dichroism, for example and by analysis of the phase solubility data for the acid-ionizable agent and anionic derivatized cyclodextrin. The artisan of ordinary skill in the art will be able to use these conventional methods to approximate the amount of each type of binding that is occurring in solution to determine whether or not binding between the species is occurring predominantly by non-covalent ionic binding or inclusion complex formation. Under conditions where non-covalent ionic bonding predominates over inclusion complex formation, the amount of inclusion complex formation, measured by NMR or circular dichroism, will be reduced even though the phase solubility data indicates significant binding between the species under those conditions; moreover, the intrinsic solubility of the acid-ionizable agent, as determined from the phase solubility data, will generally be higher than expected under those conditions.

As used herein, the term non-covalent ionic bond refers to a bond formed between an anionic species and a cationic species. The bond is non-covalent such that the two species together form a salt or ion pair. An anionic derivatized cyclodextrin provides the anionic species of the ion pair and the acid-ionizable agent provides the cationic species of the ion pair. Since an anionic derivatized cyclodextrin is multi-valent, an SAE-AE-CD can form an ion pair with one or more acid-ionizable or otherwise cationic agents.

A liquid formulation of the invention may be converted to a solid formulation for reconstitution. A reconstitutable solid composition according to the invention comprises an active agent, a derivatized cyclodextrin and optionally at least one other pharmaceutical excipient. This composition is reconstituted with an aqueous liquid to form a liquid formulation that is preserved. The composition can comprise an admixture (minimal to no presence of an inclusion complex) of a solid derivatized cyclodextrin and an active agent-containing solid and optionally at least one solid pharmaceutical excipient, such that a major portion of the active agent is not complexed with the derivatized cyclodextrin prior to reconstitution. Alternatively, the composition can comprise a solid mixture of a derivatized cyclodextrin and an active agent, wherein a major portion of the active agent is complexed with the derivatized cyclodextrin prior to reconstitution. The reconstitutable solid can also comprise a derivatized cyclodextrin and an active agent where substantially all or at least a major portion of the active agent is complexed with the derivatized cyclodextrin.

The reconstitutable formulation can be prepared according to any of the following processes. A liquid formulation of the invention is first prepared, then a solid is formed by lyophilization (freeze-drying), spray-drying, spray freeze-drying, antisolvent precipitation, various processes utilizing supercritical or near supercritical fluids, or other methods known to those of ordinary skill in the art to make a solid for reconstitution.

A liquid vehicle included in a formulation of the invention comprises an aqueous liquid carrier, such as water, aqueous alcohol, or aqueous organic solvent, or a non-aqueous liquid carrier.

Although not necessary, the formulation of the present invention may include one or more pharmaceutical excipients selected from the group consisting of a conventional preservative, antifoaming agent, antioxidant, buffering agent, acidifying agent, alkalizing agent, bulking agent, colorant, complexation-enhancing agent, cryoprotectant, electrolyte, glucose, emulsifying agent, oil, plasticizer, solubility-enhancing agent, stabilizer, tonicity modifier, flavors, sweeteners, adsorbents, antiadherent, binder, diluent, direct compression excipient, disintegrant, glidant, lubricant, opaquant, polishing agent, complexing agents, fragrances, other excipients known by those of ordinary skill in the art for use in formulations, and a combination thereof.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide alkaline medium for product stability. Such compounds include by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include by way of example and without limitation, acetic acid, acidic amino acids, citric acid fumaric acid and other alpha hydroxy acids, hydrochloric acid, ascorbic acid, phosphoric acid, sulfuric acid, tartaric acid and nitric acid and others known to those of ordinary skill in the art.

As used herein, the term "antiadherent" is intended to mean an agent that prevents the sticking of solid dosage formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "binder" is intended to mean a substance used to cause adhesion of powder particles in solid dosage formulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the dosage forms. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC™ F68, PLURONIC™ F127), collagen, albumin, gelatin, cellulosics in nonaqueous solvents, combinations thereof and others known to those of ordinary skill in the art. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, a conventional preservative is a compound used to at least reduce the rate at which bioburden increases, but preferably maintains bioburden steady or reduces bioburden after contamination. Such compounds include, by way of example and without limitation, benzalkonium chloride, benzethonium chloride, benzoic acid benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate sorbic acid, thymol, and methyl, ethyl, propyl or butyl parabens and others known to those of ordinary skill in the art. It is understood that some preservatives may interact with the SAE-AE-CD thus reducing the preservative effectiveness. Nevertheless, by adjusting the choice of preservative and the concentrations of preservative and the SAE-AE-CD adequately preserved formulations can be found.

As used herein, the term "diluent" or "filler" is intended to mean an inert substance used as a filler to create the desired bulk, flow properties, and compression characteristics in the preparation of solid dosage forms. Such compounds include, by way of example and without limitation, dibasic calcium phosphate, kaolin, lactose, dextrose, magnesium carbonate, sucrose, mannitol, microcrystalline cellulose, powdered cellulose, precipitated calcium carbonate, sorbitol, and starch and other materials known to one of ordinary skill in the art.

As used herein, the term "direct compression excipient" is intended to mean a compound used in compressed solid dosage forms. Such compounds include, by way of example and without limitation, dibasic calcium phosphate (e.g., Ditab) and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophophorous acid, monothioglycerol, propyl gallate, sodium ascorbate, sodium citrate, sodium sulfide, sodium sulfite, sodium bisulfite, sodium formaldehyde sulfoxylate, thioglycolic acid, EDTA, pentetate, and sodium metabisulfite and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, HEPES, lactic acid, tartaric acid, potassium metaphosphate, potassium phosphate, monobasic sodium acetate, sodium bicarbonate, tris, sodium tartrate and sodium citrate anhydrous and dihydrate and others known to those of ordinary skill in the art.

A complexation-enhancing agent can be added to a formulation of the invention. When such an agent is present, the ratio of cyclodextrin/active agent can be changed. A complexation-enhancing agent is a compound, or compounds, that enhance(s) the complexation of the active agent with the cyclodextrin. Suitable complexation enhancing agents include one or more pharmacologically inert water soluble polymers, hydroxy acids, and other organic compounds typically used in preserved formulations to enhance the complexation of a particular agent with cyclodextrins.

Hydrophilic polymers can be used as complexation-enhancing, solubility-enhancing and/or water activity reducing agents to improve the performance of formulations containing a cyclodextrin-based preservative. Loftsson has disclosed a number of polymers suitable for combined use with a cyclodextrin (underivatized or derivatized) to enhance the performance and/or properties of the cyclodextrin. Suitable polymers are disclosed in *Pharmazie* (2001), 56(9), 746-747; *International Journal of Pharmaceutics* (2001), 212(1), 29-40; Cyclodextrin: From Basic Research to Market, International Cyclodextrin Symposium, 10th, Ann Arbor, Mich., United States, May 21-24, 2000 (2000), 10-15 (Wacker Biochem Corp.: Adrian, Mich.); PCT International Publication No. WO 9942111; *Pharmazie*, 53(11), 733-740 (1998); *Pharm. Technol. Eur.,* 9(5). 26-34 (1997); *J. Pharm. Sci.* 85(10), 1017-1025 (1996); European Patent Application EP0579435; Proceedings of the International Symposium on Cyclodextrins, 9th, Santiago de Comostela, Spain, May 31-Jun. 3, 1998 (1999), 261-264 (Editor(s): Labandeira, J. J. Torres; Vila-Jato, J. L. Kluwer Academic Publishers, Dordrecht, Neth); *S.T.P. Pharma Sciences* (1999), 9(3), 237-242; ACS Symposium Series (1999), 737(Polysaccharide Applications), 24-45; *Pharmaceutical Research* (1998), 15(11), 1696-1701; *Drug Development and Industrial Pharmacy* (1998), 24(4), 365-370; *International Journal of Pharmaceutics* (1998), 163(1-2), 115-121; Book of Abstracts, 216th ACS National Meeting, Boston, Aug. 23-27 (1998), CELL-016, American Chemical Society; *Journal of Controlled Release*, (1997), 44/1 (95-99); *Pharm. Res.* (1997) 14(11), S203; *Investigative Ophthalmology & Visual Science*, (1996), 37(6), 1199-1203; Proceedings of the International Symposium on Controlled Release of Bioactive Materials (1996), 23rd, 453-454: *Drug Development and Industrial Pharmacy* (1996), 22(5), 401405; Proceedings of the International Symposium on Cyclodextrins, 8th, Budapest, Mar. 31-Apr. 2, (1996), 373-376. (Editor(s): Szejtli, J.; Szente, L. Kluwer: Dordrecht, Neth.); *Pharmaceutical Sciences* (1996), 2(6), 277-279; *European Journal of Pharmaceutical Sciences*, (1996) 4(SUPPL.), S144; Third European Congress of Pharmaceutical Sciences Edinburgh, Scotland, UK Sep. 15-17, 1996; *Pharmazie*, (1996), 51(1), 3942; *Eur. J. Pharm. Sci.* (1996), 4(Suppl.), S143; U.S. Pat. No. 5,472,954 and U.S. Pat. No. 5,324,718; *International Journal of Pharmaceutics* (Netherlands), (Dec. 29, 1995) 126, 73-78; Abstracts of Papers of the American Chemical Society, (2 Apr. 1995) 209(1), 33-CELL; *European Journal of Pharmaceutical Sciences*, (1994) 2, 297-301; *Pharmaceutical Research* (New York), (1994) 11(10), S225; *International Journal of Pharmaceutics* (Netherlands), (Apr. 11, 1994) 104, 181-184; and *International Journal of Pharmaceutics* (1994), 110(2), 169-77, the entire disclosures of which are hereby incorporated by reference.

Other suitable polymers are well-known excipients commonly used in the field of pharmaceutical formulations and are included in, for example, *Remington's Pharmaceutical Sciences, 18th Edition*, Alfonso R. Gennaro (editor), Mack Publishing Company, Easton, Pa., 1990, pp. 291-294; Alfred Martin, James Swarbrick and Arthur Commarata, *Physical Pharmacy. Physical Chemical Principles in Pharmaceutical Sciences, 3rd edition* (Lea & Febinger, Philadelphia, Pa., 1983, pp. 592-638); A. T. Florence and D. Altwood, (*Physicochemical Principles of Pharmacy, 2nd Edition*, MacMillan Press, London, 1988, pp. 281-334. The entire disclosures of the references cited herein are hereby incorporated by references. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

As used herein, a fragrance is a relatively volatile substance or combination of substances that produces a detectable aroma, odor or scent. Exemplary fragrances include those generally accepted as FD&C.

As used herein, the term "glidant" is intended to mean an agent used in solid dosage formulations to promote flowability of the solid mass. Such compounds include, by way of example and without limitation, colloidal silica, cornstarch, talc, calcium silicate, magnesium silicate, colloidal silicon, tribasic calcium phosphate, silicon hydrogel and other materials known to one of ordinary skill in the art.

As used herein, the term "lubricant" is intended to mean a substance used in solid dosage formulations to reduce friction during compression. Such compounds include, by way of example and without limitation, calcium stearate, magnesium stearate, PEG talc, mineral oil, stearic acid, and zinc stearate and other materials known to one of ordinary skill in the art.

As used herein, the term "opaquant" is intended to mean a compound used to render a coating opaque. May be used alone or in combination with a colorant. Such compounds include, by way of example and without limitation, titanium dioxide, talc and other materials known to one of ordinary skill in the art.

As used herein, the term "polishing agent" is intended to mean a compound used to impart an attractive sheen to solid dosage forms. Such compounds include, by way of example and without limitation, carnauba wax, white wax and other materials known to one of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g., Avicel), carboxymethylcellulose calcium, croscarmellose sodium, alginic acid, sodium alginate, cellulose polyacrilin potassium (e.g., Amberlite), alginates, sodium starch glycolate, gums, agar, guar, locust bean, karaya, pectin, tragacanth, crospovidone and other materials known to one of ordinary skill in the art.

As used herein, the term "stabilizer" is intended to mean a compound used to stabilize the therapeutic agent against physical, chemical, or biochemical process which would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those of ordinary skill in the art. In one embodiment, the tonicity of the liquid formulation approximates the tonicity of blood or plasma.

As used herein, the term "antifoaming agent" is intended to mean a compound or compounds that prevents or reduces the amount of foaming that forms on the surface of the liquid formulation. Suitable antifoaming agents include dimethicone, simethicone, octoxynol and others known to those of ordinary skill in the art.

As used herein, the term "bulking agent" is intended to mean a compound used to add bulk to the solid product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

As used herein, the term "emulsifier" or "emulsifying agent" is intended to mean a compound added to one or more of the phase components of an emulsion for the purpose of stabilizing the droplets of the internal phase within the external phase. Such compounds include, by way of example and without limitation, lecithin, polyoxylethylene-polyoxypropylene ethers, polyoxylethylene-sorbitan monolaurate, polysorbates, sorbitan esters, stearyl alcohol, tyloxapol, tragacanth, xanthan gum, acacia, agar, alginic acid, sodium alginate, bentonite, carbomer, carboxymethyl cellulose sodium, cholesterol, gelatin, hydroxyethyl cellulose, hydroxypropyl cellulose, octoxynol, oleyl alcohol, polyvinyl alcohol, povidone, propylene glycol monostearate, sodium lauryl sulfate, and others known to those of ordinary skill in the art.

A solubility-enhancing agent can be added to the formulation of the invention. A solubility-enhancing agent is a compound, or compounds, that enhance(s) the solubility of the active agent when in a liquid formulation. When such an agent is present, the ratio of cyclodextrin/active agent can be changed. Suitable solubility enhancing agents include one or more organic solvents, detergents, soaps, surfactant and other organic compounds typically used in parenteral formulations to enhance the solubility of a particular agent.

Suitable organic solvents include, for example, ethanol, glycerin, polyethylene glycols, propylene glycol, poloxomers, and others known to those of ordinary skill in the art.

The formulation of the invention can also include oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides. It can also include alcohols, such as ethanol, isopropanol, hexadecyl alcohol, glycerol and propylene glycol; glycerol ketals, such as 2,2-dimethyl-1,3-dioxolane-4-methanol; ethers, such as poly(ethylene glycol) 450; with petroleum hydrocarbons, such as mineral oil and petrolatum; water; or with mixtures thereof; with or without the addition of a pharmaceutically suitable surfactant, suspending agent or emulsifying agent.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

The formulation of the invention can also include biological salt(s), sodium chloride, potassium chloride, or other electrolyte(s).

Since some active agents are subject to oxidative degradation, a liquid formulation according to the invention can have its oxygen removed. For example, the headspace of the container with the liquid formulation is made oxygen free, substantially oxygen free, or oxygen-reduced by purging the headspace with an inert gas, such as nitrogen or argon, or by bubbling the inert gas through the liquid formulation. For long-term storage, the liquid formulation containing an active agent subject to oxidative degradation is preferably stored in an oxygen-free or oxygen-reduced environment. Removal of oxygen from the formulation will enhance preservation of the formulation against aerobic microbes; whereas, addition of oxygen to the formulation will enhance preservation against anaerobic microbes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean warm blooded animals such as mammals, for example, cats, dogs, mice, guinea pigs, horses, bovine cows, sheep and humans.

A formulation of the invention will comprise an active agent present in an effective amount. By the term "effective amount", is meant the amount or quantity of active agent that is sufficient to elicit the required or desired response, or in other words, the amount that is sufficient to elicit an appreciable biological response when administered to a subject.

The examples below detail several different methods for preparing an SAE-CD, AE-CD and SAE-AE-CD. In general, a cyclodextrin starting material in neutral to alkaline aqueous media is exposed to an alkylating and/or sulfoalkylating agent. The alkylating and/or sulfoalkylating agent can be added incrementally or as a bolus and it can be added before, during or after exposure of the cyclodextrin starting material to the optionally alkaline aqueous media. Additional alkaline material or buffering material can be added as needed to maintain the pH within a desired range. The derivatization reaction can be conducted at ambient to elevated temperatures. Once alkylation and/or sulfoalkylation, respectively, has proceeded to the desired extent, the reaction is optionally quenched by addition of an acid. The reaction milieu is further processed (e.g., solvent precipitation, filtration, centrifugation, evaporation, concentration, drying, chromatography, dialysis, and/or ultra-filtration) to remove undesired materials and form the SAE-AE-CD composition. After final processing, the composition can be in the form of a solid, liquid, semi-solid, gel, syrup, paste, powder, aggregate, granule, pellet, compressed material, reconstitutable solid, suspension, glass, crystalline mass, amorphous mass, particulate, bead, emulsion, or wet mass.

When formulated into a dosage form, the SAE-AE-CD can be present in a reconstitutable solid, tablet, capsule, pill, troche, patch, osmotic device, stick, suppository, implant, gum, effervescent composition, injectable liquid, ophthalmic or nasal solutions, or inhalable powders or solutions.

The invention also provides methods of preparing a liquid formulation comprising the SAE-AE-CD and an active agent. A first method comprises the steps of: forming a first aqueous solution comprising a cyclodextrin derivative; forming a second solution or suspension comprising active agent; and mixing the first and second solutions to form the liquid formulation. A second method is similar to the first step except that the active agent is added directly to the first solution without formation of the second solution. A third method is similar to the first except that the cyclodextrin derivative is added directly to the second solution/suspension without formation of the first solution. A fourth method comprises the steps of: adding a solution comprising active agent to a powdered or particulate cyclodextrin derivative. A fifth method comprises the steps of: adding the active agent directly to the powdered or particulate cyclodextrin derivative; and adding a second solution. A sixth method comprises the steps of: creating the liquid formulation by any of the above methods and then isolating a solid material by lyophilization, spray-drying, spray-freeze-drying, antisolvent precipitation, a process utilizing a supercritical or near supercritical fluid, or other methods known to those of ordinary skill in the art to make a powder for reconstitution.

Specific embodiments of the methods of preparing a liquid formulation include those wherein: 1) the method further comprises the step of sterile filtering the formulation through a filtration medium having a pore size of 0.1 microns or larger; 2) the liquid formulation is sterilized by irradiation or autoclaving; 3) the method further comprises the step of isolating a solid from the solution; 4) the solution is purged with nitrogen or argon or other inert pharmaceutically acceptable gas such that a substantial portion of the oxygen dissolved in, and/or in surface contact with the solution is removed.

Still another aspect of the invention provides a reconstitutable solid pharmaceutical composition comprising an active agent, a cyclodextrin derivative and optionally at least one other pharmaceutical excipient. When this composition is reconstituted with an aqueous liquid to form a preserved liquid formulation, it can be administered by injection, infusion, topically, by inhalation or orally to a subject.

Specific embodiments of the reconstitutable solid pharmaceutical composition includes those wherein: 1) the composition comprises an admixture of a solid SAE-AE-CD and active agent-containing solid comprising an active agent and optionally at least one solid pharmaceutical excipient, such that a major portion of the active agent is not complexed with the SAE-AE-CD prior to reconstitution; and/or 2) the composition comprises a solid mixture of an SAE-AE-CD and an active agent, wherein a major portion of the active agent is complexed with the SAE-AE-CD prior to reconstitution.

An SAE-AE-CD of the invention can be used in a pharmaceutical dosage form, pharmaceutical composition or other such combination of materials. These CDs will also be useful are, but not limited to, as analytical reagents, in food and cosmetics and as environmental clean up agents.

In view of the above description and the examples below, one of ordinary skill in the art will be able to practice the invention as claimed without undue experimentation. The foregoing will be better understood with reference to the following examples that detail certain procedures for the preparation of molecules, compositions and formulations according to the present invention. All references made to these examples are for the purposes of illustration. The following examples should not be considered exhaustive, but merely illustrative of only a few of the many embodiments contemplated by the present invention.

Example 1

An exemplary SAEx-AEy-CD according to the invention can be made using the following general procedure, wherein an SAE-CD in an alkaline aqueous medium is derivatized with an AE precursor to form the SAEx-AEy-CD.

SAEx-CD is placed in an aqueous medium in the presence of an alkaline material present in an amount sufficient to render the resulting mixture alkaline and deprotonate at least one of the hydroxyl substituents of the cyclodextrin ring. An AE precursor is added to the mixture in a molar amount sufficient to etherify the SAEx-CD to form the SAEx-AEy-CD having the desired DS for AE. The alkaline material may be added before during or after exposure of the SAEx-CD to the AE precursor. The ratio of y:x may be determined by control of the molar ratio of AE precursor to SAEx-CD before or during the reaction period, or it can be determined after completion of the reaction or after completion of purification of the SAEx-AEy-CD by other methods described herein.

Example 2

An exemplary SAEx-AEy-CD according to the invention can be made using the following alternate general procedure, wherein an AE-CD in an alkaline aqueous medium is derivatized with an SAE precursor to form the SAEx-AEy-CD.

AEy-CD is placed in an aqueous medium in the presence of an alkaline material present in an amount sufficient to render the resulting mixture alkaline and deprotonate at least one of the hydroxyl substituents of the cyclodextrin ring. An SAE precursor is added to the mixture in a molar amount sufficient to etherify the AEy-CD to form the SAEx-AEy-CD having the desired DS for SAE. The alkaline material may be added before during or after exposure of the AEy-CD to the SAE precursor. The ratio of y:x might be determined by control of the molar ratio of SAE precursor to AEy-CD before or during the reaction period, or it can be determined after completion of the reaction or after completion of purification of the SAEx-AEy-CD by other methods described herein.

Example 3

An exemplary SAEx-AEy-CD according to the invention can be made using the following alternate general procedure, wherein an underivatized parent CD in an alkaline aqueous medium is derivatized with an SAE precursor and an AE precursor to form the SAEx-AEy-CD.

Parent cyclodextrin (CDz, wherein "z" indicated the number of moles) is placed in an aqueous medium in the presence of an alkaline material present in an amount sufficient to render the resulting mixture alkaline and deprotonate at least one of the hydroxyl substituents of the cyclodextrin ring. An SAE precursor, an AE precursor or a mixture thereof is added to the parent cyclodextrin in a molar amount sufficient to etherify the parent CD to form the SAE-CD, AE-CD or SAEx-AEy-CD, respectively. The alkaline material may be added before during or after exposure of the parent CD to the precursors. The SAE precursor and AE precursor can be added sequentially, simultaneously, or in an overlapping manner. The molar ratios of x:y, x:z, y:z and x:y:z might be determined by control of the molar ratio of SAE precursor and AE precursor to the parent CD before or during the reaction period, or it can be determined after completion of the reaction or after completion of purification of the SAEx-AEy-CD by other methods described herein.

This reaction can also be performed sequentially where by the SAE precursor is added and allowed to proceed to completion. Without further purification, the AE precursor is added and the reaction allowed to proceed.

Example 4

The following procedure was used to analyze the SAE-AE-CD by capillary electrophoresis.

A Beckman P/ACE 2210 capillary electrophoresis system coupled with a UV absorbance detector (Beckman instruments, Inc., Fullereton, Calif.) was used to analyze a 5 mM solution of each SBE-β and SBE-γ CD derivative. The separation was performed at 25° C. using a fused silica capillary (50 μm inner diameters total length of 57 cm and effective length of 50 cm) with a pH 7.0 running buffer 23 mM benzoic acid and 25 mm TRIS (tris-hydroxymethyl-aminomethano).

The capillary was treated with the following wash sequence before each injection with 7 volume exchanges (VEs) of water, 5 VEs 0.01N NaOH, 3VEs water, 5VEs running buffer. The detector was set at 230 nm. The current was 25-30 μA. Samples were introduced by pressure injections: 1 s at 5 psi.

Figure 2:
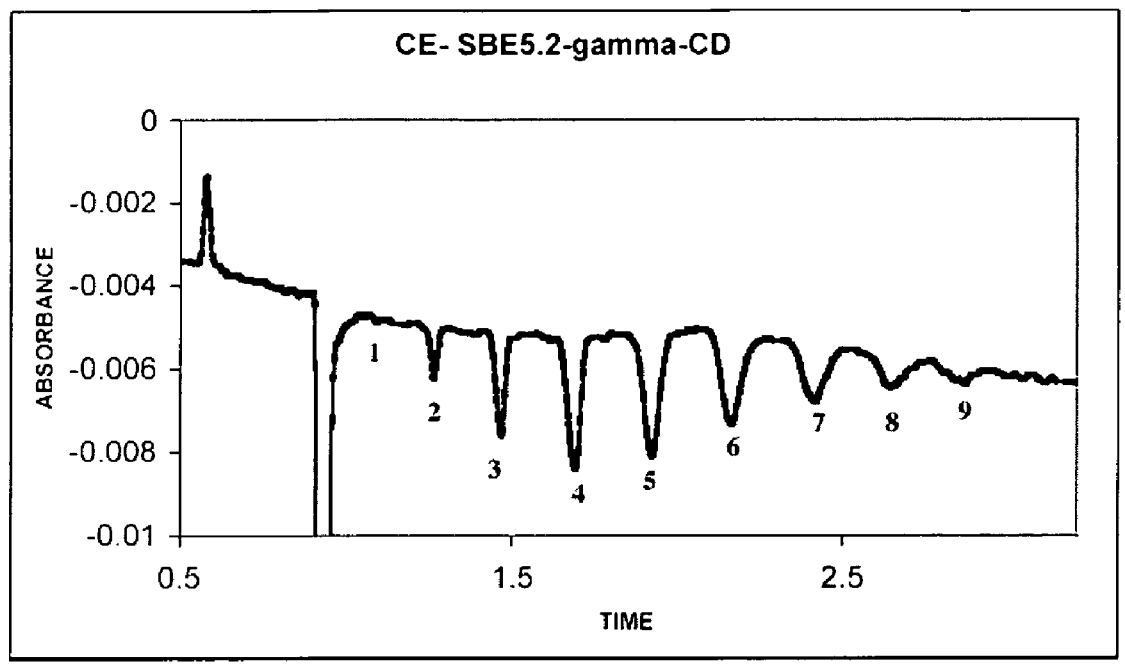
FIG. 2 depicts an electropherogram of SBE5.2-γ-CD, which was used as a starting material for the preparation of SBE5.2-Et4.9-γ-CD.
Figure 3:
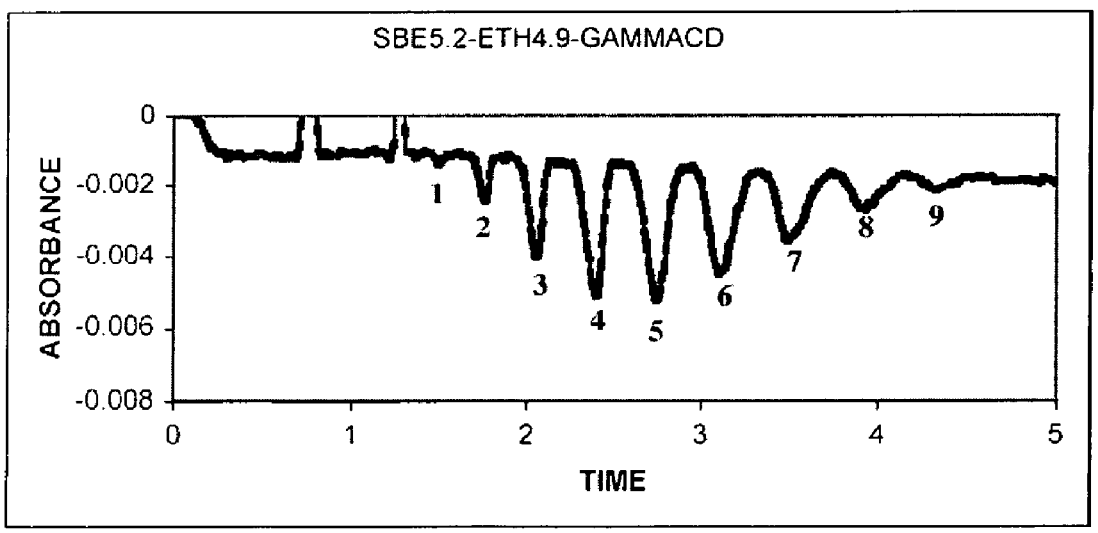
FIG. 3 depicts an electropherogram of SBE5.2-Et4.9-γ-CD made from the SBE5.2-γ-CD of FIG. 2.

FIGS. 2-3 depict electropherograms obtained for the analysis of SBE5.2-γ-CD (FIG. 2) and SBE5.2-Et4.9-γ-CD (FIG. 3). The electropherogram indicate the peaks corresponding to the various isomers. For example, FIG. 2 depicts nine numbered peaks, wherein each peak corresponds to an SBE-γ-CD having the degree of substitution indicated by the number at the apex of the peak. Accordingly, the SBE5.2-γ-CD starting material actually comprises about nine different species, i.e. $SBE_{1-9}$-γ-CD. The average TDS, however, for the SBE groups is 5.2 as determined by averaging peak areas.

FIG. 3 also depicts nine numbered peaks, since it is an electropherogram of the ethyl ether derivative derived from SBE5.2-γ-CD. The TDS for the ethyl ether substituent was determined with NMR by integration of the peaks of the spectra described below.

Example 5

The following procedure was used to evaluate the moisture content the cyclodextrin derivatives.

Determinations were performed in triplicate on 5-10 mg of each using a Brinkman 652 Karl-Fischer Coulometer (Brinkman Instruments Co., IL). A known weight of solid CD is added to the Karl-Fischer Coulometer and the total amount of water in the sample is read-out. This is then converted to a percentage of the solid thus giving the percent moisture content of the sample.

Example 6

The identity of the cyclodextrin derivatives was determined by $^1$HNMR, $^{13}$CNMR, COSY NMR and HMQC on a Bruker Avance 400 or 500 instrument in $D_2O$ solutions.

FIG. 1 depicts the HMQC spectrum of SBE4.6-Et6.0-β-CD. The peak assignments corresponding to the indicated carbon atoms of the glucopyranose carbons are indicated in the figure. The HMQC spectrum of compounds that have SBE sidechains, ethyl sidechains, and both, exhibit a consistent pattern of chemical shift changes resulting from substituents. The effects of SBE substitution and ethyl substitution are very similar, because in each case, an ether linkage is formed to a sugar carbon in which there is a —$CH_2$ group on the other side of the ether oxygen, and another carbon connected to that. The directly substituted sugar carbon shifts downfield about 8 ppm, while the proton attached to that carbon shifts upfield by ~0.2 ppm. The sugar carbon next to the site of substitution shifts upfield by 2-3 ppm, while the proton attached to that carbon shifts downfield by about 0.2 ppm. The effects of substitution at 2 are clearly seen on the C-1 and H-1 signal. The effects of substitution at 6 are also easy to see in the carbon spectrum, because C-6 is more than 10 ppm upfield of the other sugar carbons. The effect of a substitution at 3 is somewhat more difficult to observe. Substitution at C-2 or C-3 shifts that carbon signal out near the shift of C-4; however, substitution at C-3 shifts the C-4 signal upfield as well as shifting C-3 downfield.

Figure 4:
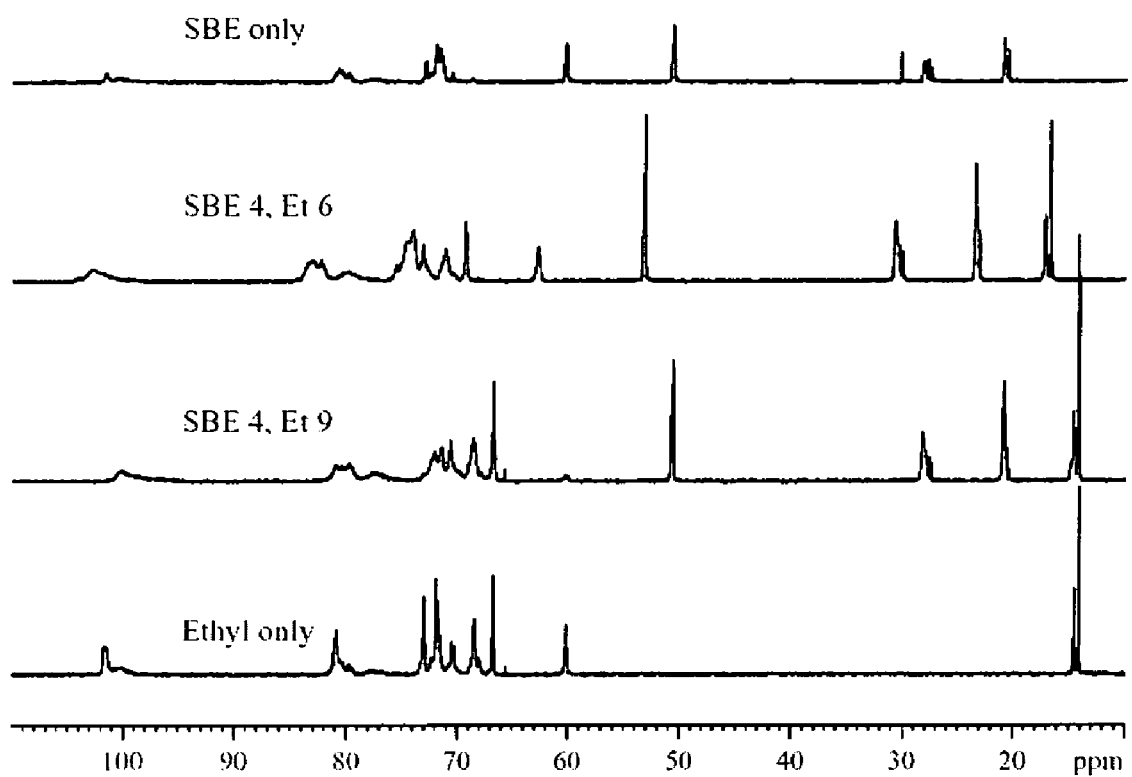
FIG. 4 depicts the $^{13}$CNMR spectrum of SBE4.6-β-CD, SBE4.6-Et6.0-β-CD, SBE4.6-Et9-β-CD, and Et-β-CD.

FIG. 4 depicts the $^{13}$CNMR spectrum of SBE4.6-β-CD, SBE4.6-Et6.0-β-CD, SBE4.6-Et9-β-CD, and Et-β-CD compositions.

Figure 5:
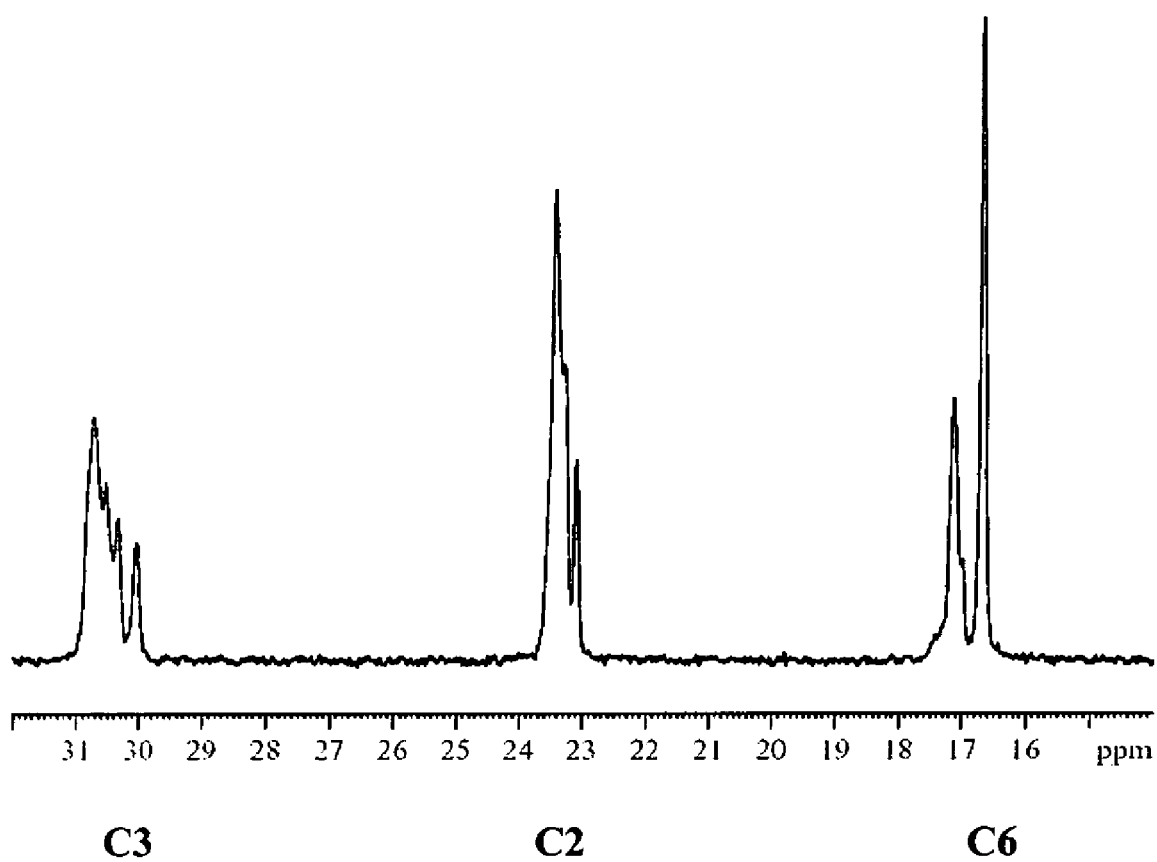
FIG. 5 depicts an expanded $^{13}$CNMR spectrum of the 15-32 ppm region for SBE4.6-Et6.0-β-CD.

FIG. 5 depicts an expanded $^{13}$CNMR spectrum of the C2, C3 and C6 carbon atoms of an SAE-AE-CD of the invention, in particular SBE4.6-Et6.0-β-CD. The peak amplitude was used to determine the degree of substitution. The 1D spectra is analyzed for quantitation (determination of DS). First, the inter-pulse delay is made greater than 5*T1, since the sugar carbons have short T1's. The side-chain carbons, which have internal mobility in addition to the overall molecular mobility, however, show much larger NOE's, and at the same time, have much longer T1's. The NOE's have a much larger effect on the observed signal intensity. This means that one cannot easily integrate carbon spectra taken with the usual parameters to determine the number of ethyl or SBE groups; those carbons will have disproportionately large signals relative to the sugar carbons. But the situation is better for integrating the unsubstituted 6 carbons against the substituted 6 carbons or one kind of ethyl CH3 against another. In this case the T1's and NOE's are very similar. So it is straightforward to determine the amount of substitution at 6 from the 6 signal, and the amount at 2 from the 1 signal. Additionally we know the total degree of substitution from the 1H spectrum, so the level of substitution at 3 is determined by difference of the product as compared to the starting material. It is apparent from the $^{13}$C spectrum of the SBE that the 2-position is extensively substituted while the 6-position reacts much less. The order of substitution appears to be 2>3>6. However, in the random ethyl, the 6-position is derivatized to a greater extent than the 2-position. Also, the ethyl $CH_3$ carbon signal is split into 3 signals. It is reasonable to assume that these correspond to an ethyl substitution at 2, 3, or 6, so we can measure the level of ethyl substitution directly from these carbon signals. In this case the order of substitution is 6>2>3.

It should be noted that there may be a slight difference in the DS or TDS reported for a specific cyclodextrin composition when using different methods of determination. Unless otherwise specified, the DS or TDS of a material is an accurate estimation of the experimentally determined value.

Example 7

The following general procedure was used to determine the phase solubility diagram for each active agent/cyclodextrin derivative combination.

Solubility studies were conducted using the phase solubility method described by Higuchi and Connors (T. Higuchi and K. A Connors, "Phase solubility techniques". *Advance in Analytical Chemistry and Instrumentation*, vol. 4 (1965), 117-212).

Excess amount of drug was added to a CD-containing aqueous solution (concentration ranging from 0 to 0.10M). The solution was equilibrated at room temperature for 24 hours after which time a suspension remained. The suspension was centrifuged for 5 min. at 3000 rpm (Dynac™ centrifuge, Clay Adams, Parsippany, N.J.). A 20 µL sample was obtained from the supernatant and diluted to 1-5-ml with glass double distilled water. After dilution the amount of drug in solution measured detected by HPLC with UV detection set at the particular wavelength ($\lambda$, nm) depending on the drug being analyzed.

The HPLC equipment consisted of a) an LC-10AT liquid chromatograph, SIL-10A auto injector, SPD-10A UV-Vis detector and a SCL-10 system controller (Schimadzu Scientific Instruments, Inc. Japan); b) an Hewlett Packard 1090 Series L, Rheodyne, (Cotati) injector, Diode Array Detector interfaced with an Agilent ChemStation data processor; The column was a 15 cm×4.6 mm i.d. C18 ODS Hypersil (5 µm pore size).

The mobile phase(s) was chosen in accordance with the properties of the analyzed drug and its behavior in interacting with the chromatographic support. Suitable exemplary conditions for specific drugs are detailed in the table below.

| DRUG | MOBILE PHASE | $\lambda$ nm |
|---|---|---|
| CAMPTOTHECIN | H$_2$0:CH$_3$CN:FORMIC:ACID (6.5:3.0:0.05 V/V) pH = 4.4 | 370 |
| α-Me-PREDNISOLONE | CH$_3$CN:ACETATE BUFFER(0.02 M) (30:70 V/V) pH = 4.7 | 254 |
| NIFEDIPINE | H$_2$0:CH$_3$CN (6.0:4.0 V/V) + ACEDICACID/ AMMONIUM ACETATE pH = 4.0 | 340 |
| CARBAMAZEPINE | CH$_3$CN:PHOSPHATE BUFFER (45:55 V/V) pH = 6.5 | 215 |

Example 8

The following general procedure was used to determine the extent of inclusion complex formation for an active agent/cyclodextrin derivative combination. The change in absorbance due to inclusion complex formation for a drug was monitored. The change in absorbance value as a function of total ligand concentration at a fixed concentration of substrate was measured. The wavelength for analysis was chosen appropriately depending on the analyzed drug. The analysis was performed using a Perkin Elmer double beam UV/Vis Lamda 6 instrument equipped with a data manager software and water jacketed multicell attachment. A circulating water bath was used to provide constant temperature during experiments. The data were linearized using the method described by Foster et al.: R. Foster, D. L. Hammich, A. A Wardley (Interaction of Polynitro compounds with Aromatic Hydroquinones and Bases. Part III. A New Method for Determining the Association Constants for Certain Interactions between Nitro Compounds and Bases in Solution. *J. Chem. Soc.* (1953) 3817-20).

1 µl aliquots of concentrated cyclodextrin solution (0.1M) to were added incrementally to a drug-containing (5×10$^{-5}$ M) solution and a reference solution not containing drug. The cyclodextrin was added one µl at time up to a maximum volume of 10 µl. Both the drug-containing and cyclodextrin-containing solutions were filtered by 0.45 µm Acrodisc filter. Matched quartz cuvettes of 1.5 ml in volume and 1 cm optical length were used. The cyclodextrin solution was titrated 1 µl at a time through a 5.0 µl Hamilton syringe directly in drug solution in cuvettes. The drug-containing cuvette was inverted to favor the complex formation and equilibrate for 5 minutes before measurement. The following conditions were used for the drugs indicated in the table below.

| DRUG | $\lambda$ max | pH |
|---|---|---|
| α-Me-prednisolone | 246 | 6.5 |
| Prednisolone | 246 | 6.5 |
| Nifedipine | 340 | 6.5 |
| Nimodipine | 340 | 6.5 |
| Nitredipine | 340 | 6.5 |
| Clotrimazole | 266 | 3.0 |
| Triamcinolone | 238 | 6.5 |
| Carbamazepine | 215 | 6.5 |

Example 9

An exemplary SBE-β-CD and SBE-γ-CD were made using the following procedure, wherein the parent CD in an alkaline aqueous medium was derivatized with an SBE precursor to form the SBEx-β-CD or SBE-γ-CD, respectively.

The β or γ CD was dissolved in 4N NaOH aqueous solution. The mixture was heated to 75° C., and stirred until complete dissolution. 1,4-Butanesultone was added in four equivalent portions every 10 minutes. The amount of equivalents added was proportional to the degree of substitution of the final product. The reaction pH was monitored for 1.5 hours, and adjusted to pH 9-10 with 4N NaOH aqueous solution as needed. The reaction was allowed to continue for an additional 16 hours. The reaction medium was diluted with water, cooled (50% of the reaction volume), cooled to room temperature and neutralized (pH 6.8-7.2), with a 3N HCL aqueous solution. The solution was filtered through a 0.45 µm filter, diluted to an approximate 5% solution and dialyzed against water. The ultra filtration end point was determined by capillary electrophoresis, wherein the filtrate showed no or substantially no presence of 4-hydroxybutensulfonate sodium salt and/or 4,4$^1$-disulfonobutyl ether disodium salt, and by precipitation reaction with a 0.1 M AgNO$_3$ solution, wherein the filtrate showed no or substantially no presence of chloride anion. The resulting solution was concentrated with a Rotavap at 50° C. under vacuum and freeze-dried. The equivalents of alkylating agent and the yields of the reaction are indicated in the tables above directed to SAE-AE-γ-CD and SAE-AE-β-CD.

Example 10

An exemplary SBE-Et-β-CD and SBE-Et-γ-CD were made using the following procedure, wherein the starting SBE-β-CD or SBE-γ-CD, respectively, in an alkaline aqueous medium was derivatized with an AE precursor to form the SBEx-Ety-β-CD or SBEx-Et-γ-CD, respectively.

The SBE-β or SBE-γ CD derivative, with the desired DS (degree of substitution) with regard to the SBE was dissolved in 4N NaOH aqueous solution. The mixture was stirred until complete dissolution at room temperature. The diethylsulfate was added in four equivalent portions every 10 minutes, or until a clear solution was formed. The amount of equivalents added was proportional to the degree of substitution for ethylation of the final products. The reaction pH was monitored for 1 hour, and adjusted to pH 9-12 with 4N NaOH aqueous solution as needed. The reaction was allowed to continue for an additional 72 hours. The reaction medium was diluted with water (50% of the reaction volume), cooled to room temperature and neutralized (pH 6.8-7.2), with a 3N HCL aqueous solution. The solution was filtered through a 0.45 μm filter, diluted to an approximate 5% solution and dialyzed (ultra-filtered) against water. The ultra filtration end point was determined by precipitation reaction with a 0.1 M $AgNO_3$ solution (the filtrate showed no presence of chloride anion). The resulting solution was concentrated with a Rotavap at 50° C. under vacuum and freeze-dried. The equivalents of alkylating agent and the yields of the reaction are indicated in the tables above directed to SAE-AE-γ-CD and SAE-AE-β-CD.

Example 11

An exemplary SBE-Me-β-CD and SBE-Me-γ-CD were made using the following procedure, wherein the starting SBE-β-CD or SBE-γ-CD, respectively, in an alkaline aqueous medium was derivatized with an AE precursor to form the SBEx-Mey-β-CD or SBEx-Me-γ-CD, respectively.

The SBE-β or SBE-γ CD derivative, with the desired DS with respect to SBE, was dissolved in 4N NaOH aqueous solution. The mixture was stirred until complete dissolution at room temperature. The reaction was cooled in an ice/water bath. Dimethylsulfate was added in four equivalent portions every 10 minutes, or until a clear solution was formed. The number of molar equivalents added was proportional to the degree of substitution for methylation of the final product. The reaction pH was monitored for 1 hour and adjusted to pH 9-12 with 4N NaOH aqueous solution as needed. The reaction was allowed to continue for an additional 48 hours at room temperature. The reaction medium was diluted with water, cooled (50% of the reaction volume), cooled to room temperature and neutralized (pH 6.8-7.2), with a 3N HCL aqueous solution. The solution was filtered through 0.45 μm filter, diluted to an approximate 5% solution and dialyzed (ultra-filtered) against water. The ultra filtration end point was determined by precipitation reaction with a 0.1 M $AgNO_3$ solution (the filtrate showed no presence of chloride anion). The resulting solution was concentrated with a Rotavap at 50° C. under vacuum and freeze-dried. The molar equivalents of alkylating agent and the yields of the reaction are indicated in the tables above directed to SAE-AE-γ-CD and SAE-AE-β-CD.

Example 12

Method A

An exemplary SBE-Et-β-CD and SBE-Et-γ-CD were made using the following "one-pot" procedure, wherein the parent β-CD or γ-CD, respectively, in an alkaline aqueous medium was derivatized with an SAE precursor to form the SBEx-β-CD or SBEx-γ-CD, respectively, which SBE-CD was then treated with an AE precursor to form the SBE-Et-β-CD and SBE-Et-γ-CD, respectively.

β-CD or γ-CD was dissolved in 4N NaOH aqueous solution. The mixture was heated to 75° C., and stirred until complete dissolution. 1,4-Butanesultone was added to the solution in four equivalent portions every 10 minutes. The amount of equivalents added was proportional to the degree of substitution of the final product. The reaction pH was monitored for 1.5 hours, and adjusted to pH 9-10 with 4N NaOH aqueous solution as needed. The reaction was allowed to continue for an additional 16 hours. After this time, the pH was monitored and adjusted to 10-12 with 4N NaOH (5 eq.) aqueous solution. The mixture was cooled to room temperature, and diethylsulfate was added in 4 equivalent portions. The amount added was proportional to the desired TDS. The reaction was allowed to continue at room temperature for 72 hours. The reaction medium was diluted with cool water (50% of the reaction volume), cooled to room temperature and neutralized (to pH 6.8-7.2) with a 3N HCL aqueous solution. The solution was filtered through 0.45 μm filter, diluted to an approximate 5% solution and dialyzed (ultra-filtered) against water. The ultra filtration end point was determined by capillary electrophoresis (the filtrate showed no or substantially no presence of 4-hydroxybutensulfonate sodium salt and/or $4,4^1$-disulfonobutyl ether disodium salt) and by precipitation reaction with a 0.1 M $AgNO_3$ solution (the filtrate showed no or substantially no presence of chloride anion). The resulting solution was concentrated with a Rotavap at 50° C. under vacuum and freeze-dried.

Method B

An exemplary SBE-Et-β-CD and SBE-Et-γ-CD were made using the following "one-pot" procedure, wherein the parent β-CD or γ-CD, respectively, in an alkaline aqueous medium was derivatized with an AE precursor to form the Ety-β-CD or Ety-γ-CD, respectively, which Et-CD was then treated with an SAE precursor to form the SBEx-Ety-β-CD and SBEx-Ety-γ-CD, respectively.

The procedure of Method A was followed except that the order of addition of starting materials was reversed. The AE precursor was reacted with the parent CD in alkaline medium, and the resulting AE-CD was reacted with the SAE precursor to form the desired product.

Example 13

Method A

An exemplary SBE-Me-β-CD and SBE-Me-γ-CD were made using the following "one-pot" procedure, wherein the parent β-CD or γ-CD, respectively, in an alkaline aqueous medium was derivatized with an SAE precursor to form the SBEx-β-CD or SBEx-γ-CD, respectively, which SBE-CD was then treated with an AE precursor to form the SBE-Me-β-CD and SBE-Me-γ-CD, respectively.

The procedure of Example 12 (Method A) was followed with the exception that dimethylsulfate rather than diethylsulfate was used as the AE precursor.

Method B

An exemplary SBE-Me-β-CD and SBE-Me-γ-CD were made using the following "one-pot" procedure, wherein the parent β-CD or γ-CD, respectively, in an alkaline aqueous medium was derivatized with an AE precursor to form the Mey-β-CD or Mey-γ-CD, respectively, which Me-CD was then treated with an SAE precursor to form the SBEx-Mey-β-CD and SBEx-Mey-γ-CD, respectively.

The procedure of Example 12 (Method B) was followed with the exception that dimethylsulfate rather than diethylsulfate was used as the AE precursor.

Example 14

An exemplary liquid formulation comprising an active agent and an SAEx-AEy-CD can be made according to the following general procedures.

Method A

An SAEx-AEy-CD and an active agent were placed in an aqueous solution, which was then mixed, optionally while heating for a period of time until at least a portion of the SAEx-AEy-CD and active agent was dissolved, optionally forming a complex between the SAEx-AEy-CD and active agent.

Method B

An SAEx-AEy-CD was added to an active agent in an aqueous solution while mixing, and optionally while heating, for a period of time until at least a portion of the SAEx-AEy-CD and active agent was dissolved, optionally forming a complex between the SAEx-AEy-CD and active agent.

Method C

An active agent was added to an SAEx-AEy-CD in an aqueous solution while mixing, optionally while heating, for a period of time until at least a portion of the SAEx-AEy-CD and active agent was dissolved, optionally forming a complex between the SAEx-AEy-CD and active agent.

Method D

A composition comprising an admixture of an active agent and an SAEx-AEy-CD was mixed with an aqueous solution while mixing, optionally while heating, for a period of time until at least a portion of the SAEx-AEy-CD and active agent was dissolved, optionally forming a complex between the SAEx-AEy-CD and active agent.

Method E

A composition comprising an inclusion complex of an active agent and an SAEx-AEy-CD was mixed with an aqueous solution while mixing, optionally while heating, for a period of time until at least a portion of the SAEx-AEy-CD and active agent was dissolved, optionally forming a complex between the SAEx-AEy-CD and active agent.

Heating of a solution can be conducted at elevated temperatures (above 25-30 C) provided a substantial amount of the SAE-AE-CD and/or active agent does not degrade under those conditions.

Example 15

The following procedure was used to evaluate the hemolytic potential of an SAE-AE-CD of the invention.

Erythrocytes were separated from freshly drawn citrated rabbit blood and separated by centrifugation (Dynac™ centrifuge, Clay Adams, Parsippany, N.J.) at 1000×g for 10 minutes. After that time the plasma was removed and the red blood cells were washed three times with phosphate buffered saline (pH 7.4) and resuspended in the buffered solution to give a hematocrit of 5%. The red blood cells suspension (0.1 ml) was added to different concentration of 2 ml CD buffer solutions (range of concentration: 0.01 to 0.1 M). After 30 minutes of incubation at 37° C. the release of hemoglobin was measured spectrophotometrically at 543 nm. (Perkin Elmer double beam UV/Vis Lamda 6 instrument). The degree of hemolysis was reported as a percentage of total release heme. The 100% released heme was obtained by substitution of the CD solution with 2 mL distilled water.

The disclosures of the references cited herein are hereby incorporated in their entirety.

LIST OF SYMBOLS AND ABBREVIATIONS

| | |
|---|---|
| AEy-CD | Alkyl ether cyclodextrin wherein the degree of substitution for alkyl ether groups is defined by "y", which is a number. |
| CD | Cyclodextrin |
| CE | Capillar electrophoresis |
| DS | Degree of substitution |
| eq. | Equivalent(s) |
| HMQC | Heteronuclear multiple-quantum correlation |
| HPLC | High performance liquid chromatography |
| K1:1 | Binding constant of a 1:1 cyclodextrin:drug complex |
| MW | Molecular weight |
| NMR | Nuclear magnetic resonance |
| SAEx-CD | Sulfoalkyl ether cyclodextrin wherein the degree of substitution for sulfoalkyl ether groups is defined by "x", which is a number. |
| SBE-CD | Sulfobutyl ether cyclodextrin |
| SAE-AE-CD | Sulfoalkyl ether-alkyl ether cyclodextrin |
| SBE-AE-CD | Sulfobutyl ether-alkyl ether cyclodextrin |
| SBE-Et-CD | Sulfobutyl ether-Ethyl ether cyclodextrin |
| SBE-Me-CD | Sulfobutyl ether-Methyl ether cyclodextrin |
| SPE-Me-CD | Sulfopropyl ether-Methyl ether cyclodextrin |
| SEE-Pr-CD | Sulfoethyl ether-Propyl ether cyclodextrin |
| SPtE-Me-CD | Sulfopentyl ether-Methyl ether cyclodextrin |
| SHE-Me-CD | Sulfohexyl ether-Methyl ether cyclodextrin |
| TDS | Total degree of substitution |
| UV | Ultraviolet |

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A composition comprising an (SAET)x-(AE)y-CD of the Formula 3:

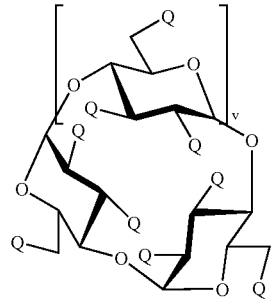

Formula 3 wherein:

v is 4, 5 or 6; and

Q is independently selected at each occurrence from the group consisting of —OH, -SAET" and -AE";

x is the degree of substitution for the SAET moiety and is 1 to 3v+z;

y is the degree of substitution for the AE moiety and is 1 to 3v+z;

z is 0 to 5;
-SAE is —O—(C$_2$-C$_6$ alkylene)-SO$_3^-$;
T is independently at each occurrence a cation; and
AE is —O(C$_1$-C$_3$ alkyl);
provided that at least one -SAET moiety and at least one -AE moiety are present; and the sum of x, y and the total number of —OH groups in a cyclodextrin derivative is 3v+6; wherein the composition excludes a permethylated β-CD comprising a single —SBE moiety.

2. A composition according to claim 1, wherein the SAEx-AEy-CD is selected from the group consisting of:
SEEx-Mey-α-CD, SEEx-Mey-β-CD, SEEx-Mey-γ-CD,
SEEx-Lty-α-CD, SEEx-Ety-β-CD, SEEx-Ety-γ-CD,
SEEx-Pry-α-CD, SEEx-Pry-β-CD, SEEx-Pry-γ-CD,
SPEx-Mey-α-CD, SPEx-Mey-β-CD, SPEx-Mey-γ-CD,
SPEx-Ety-α-CD, SPEx-Ety-β-CD, SPEx-Ety-γ-CD,
SPEx-Pry-α-CD, SPEx-Pry-β-CD, SPEx-Pry-γ-CD,
SBEx-Mey-α-CD, SBEx-Mey-β-CD, SBEx-Mey-γ-CD,
SBEx-Lty-α-CD, SBEx-Ety-β-CD, SBEx-Ety-γ-CD,
SBEx-Pry-α-CD, SBEx-Pry-β-CD, SBEx-Pry-γ-CD,
SPtEx-Mey-α-CD, SPtEx-Mey-β-CD, SPtEx-Mey-γ-CD,
SPtEx-Ety-α-CD, SPtEx-Ety-β-CD, SPtEx-Ety-γ-CD,
SPtEx-Pry-α-CD, SPtEx-Pry-β-CD, SPtEx-Pry-γ-CD,
SHEx-Mey-α-CD, SHEx-Mey-β-CD, SHEx-Mey-γ-CD,
SHEx-Ety-α-CD, SHEx-Ety-β-CD, SHEx-Ety-γ-CD,
SHEx-Pry-α-CD, SHEx-Pry-β-CD, and SHEx-Pry-γ-CD.

3. A composition according to claim 1, wherein x equals y.

4. A composition according to claim 1, wherein x is greater than y.

5. A composition according to claim 1, wherein x is less than y.

6. A composition according to claim 1, wherein
x is from 1 to 11; and
y is from 1 to 11.

7. A composition according to claim 1, wherein more than half of the Q groups are -SAET or -AE.

8. A composition according to claim 1, wherein half or less than half of the Q groups are -SAET or -AE.

9. A composition according to claim 1, wherein the alkylene radical of the SAE group is the same as the alkyl radical of the AE group.

10. A composition according to claim 1, wherein the alkylene radical of the SAE group is different than the alkyl radical of the AE group.

11. A composition according to claim 1, wherein the composition further comprises an AE-CD.

12. A composition according to claim 11, wherein the composition comprises less than 50% wt. of AE-CD.

13. A composition according to claim 11, wherein the composition further comprises an SAE-CD.

14. A composition according to claim 13, wherein the composition further comprises an underivatized parent CD.

15. A composition according to claim 14, wherein the composition comprises less than 50% wt. total of SAE-CD, AE-CD and underivatized parent CD.

16. A composition according to claim 1, wherein the composition further comprises an SAE-CD.

17. A composition according to claim 16, wherein the composition comprises less than 50% wt. of SAE-CD.

18. A composition according to claim 16, wherein the composition further comprises an underivatized parent CD.

19. A composition according to claim 1, wherein the composition further comprises an underivatized parent CD.

20. A composition according to claim 19, wherein the composition comprises less than 50% wt. of underivatized parent CD.

21. A composition according to claim 1, wherein a majority of the hydroxyl groups of the parent cyclodextrin is derivatized by an SAE moiety.

22. A composition according to claim 1, wherein a majority of the hydroxyl groups of the parent cyclodextrin is derivatized by an AE moiety.

23. A composition according to claim 1, wherein the majority of the SAE groups present are located at the C-6 positions of the parent cyclodextrin.

24. A composition according to claim 1, wherein the majority of the SAE groups present are located at one or both of the C-2 or C-3 positions of the parent cyclodextrin.

25. A composition according to claim 1, wherein the majority of the AE groups present are located at the C-6 positions of the parent cyclodextrin.

26. A composition according to claim 1, wherein the majority of the AE groups present are located at one or both of the C-2 or C-3 positions of the parent cyclodextrin.

27. A composition according to claim 1, wherein the SAE and AE moieties are substantially evenly distributed among the C-2, C-3 and C-6 positions of the parent cyclodextrin.

28. A composition according to claim 1, wherein the SAE-AE-CD contains on average at least one to ≦3v+5 SAE moieties per cyclodextrin molecule and on average at least one to ≦3v+5 AE moieties per cyclodextrin molecule.

29. An active composition comprising an (SAET)x-(AE)y-CD-containing composition according to claim 1 and at least one active agent.

30. An active composition according to claim 29, wherein the at least one active agent is present in a molar excess as compared to the (SAET)x-(AE)y-CD.

31. An active composition according to claim 29, wherein the (SAET)x-(AE)y-CD is present in a molar excess as compared to the at least one active agent.

32. An active composition according to claim 29, wherein a major portion of the at least one active agent is complexed with the (SAET)x-(AE)y-CD.

33. An active composition according to claim 29, wherein a major portion of the at least one active agent is not complexed with the (SAET)x-(AE)y-CD.

34. An active composition according to claim 29 further comprising at least one pharmaceutical excipient.

35. An active composition according to claim 29, wherein the active agent is selected from the group consisting of a pesticide, herbicide, insecticide, antioxidant, plant growth instigator, sterilization agent, catalyst, chemical reagent, food product, nutrient, cosmetic, vitamin, sterility inhibitor, fertility instigator, microorganism, flavoring agent, sweetener, cleansing agent, pharmaceutically effective active agent, and other such compounds for pharmaceutical, veterinary, horticultural, household, food, culinary, agricultural, cosmetic, industrial, cleaning, confectionery and flavoring use.

36. The active composition of claim 35, wherein the active agent is present in its neutral, ionic, salt, basic, acidic, natural, synthetic, diastereomeric, isomeric, enantiomerically pure, racemic, hydrate, chelate, derivative, or analog form.

37. The active composition of claim 35, wherein the pharmaceutically effective active agent is selected from the group consisting of nutrients, nutritional agents, hematological agents, endocrine agents, metabolic agents, cardiovascular agents, renal agents, genitourinary agents, respiratory agents, central nervous system agents, gastrointestinal agents, anti-infective agents, biologic agents, immunological agents, dermatological agents, ophthalmic agents, antineoplastic agents, and diagnostic agents.

38. A method of preparing an SAE-AE-CD containing composition of claim 1, wherein the SAE-AE-CD is a compound of the formula 3, the method comprising the steps of:
exposing an SAE-CD, wherein the SAE-CD comprises at least one underivatized hydroxyl moiety, in aqueous alkaline media to an AE precursor for a period of time sufficient, at a temperature sufficient and at a solution pH sufficient to permit formation of an SAE-AE-CD compound; and processing the media containing the SAE-AE-CD compound to remove undesired components thereby forming an SAE-AE-CD containing composition.

39. A method of preparing an SAE-AE-CD containing composition of claim 1, wherein the SAE-AE-CD is a compound of the formula 3, the method comprising the steps of:
a) exposing an underivatized parent CD in aqueous alkaline media to an AE precursor, an SAE precursor, or a combination of both for a period of time sufficient, at a temperature sufficient and at a solution pH sufficient to permit formation of an AE-CD, SAE-CD, or SAE-AE-CD compound, respectively; and
b) if no SAE precursor was present in step a), exposing the AE-CD compound, wherein the AE-CD compound comprises at least one underivatized hydroxyl moiety, in aqueous alkaline media to an SAE precursor for a period of time sufficient, at a temperature sufficient and at a solution pH sufficient to permit formation of an SAE-AE-CD compound; or
b) if no AE precursor was present in step a), exposing the SAE-CD compound, wherein the SAE-CD compound comprises at least one underivatized hydroxyl moiety, in aqueous alkaline media to an AE precursor for a period of time sufficient, at a temperature sufficient and at a solution pH sufficient to permit formation of an SAE-AE-CD compound; and
c) processing the media containing the SAE-AE-CD compound to remove undesired components thereby forming an SAE-AE-CD containing composition.

40. A method of preparing an SAE-AE-CD containing composition of claim 1, the method comprising the steps of:
a) exposing an SAE-CD compound of the formula 1

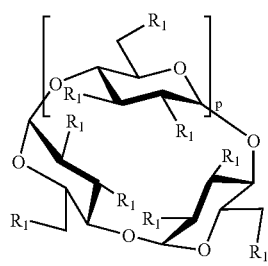

Formula 1 wherein:

p is 4, 5 or 6;

$R_1$ is independently selected at each occurrence from —OH or -SAET;

-SAE is —O—($C_2$-$C_6$ alkylene)-$SO_3^-$;

T is independently selected at each occurrence a cation; and provided that at least one $R_1$ is a hydroxyl moiety and at least one $R_1$ is SAET;

in aqueous alkaline media to an AE precursor for a period of time sufficient, at a temperature sufficient and at a solution pH sufficient to permit formation of SAE-AE-CD compound; and b) processing the media containing the SAE-AE-CD compound to remove undesired components thereby forming an SAE-AE-CD containing composition.

41. A method of preparing an SAE-AE-CD containing composition of claim 1, the method comprising the steps of:
a) exposing an AE-CD compound of the formula 2

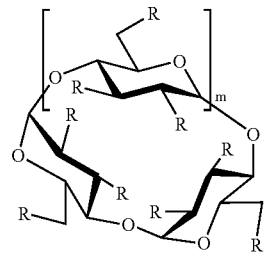

Formula 2 wherein:

m is 4, 5 or 6; and

R is independently selected at each occurrence from the group consisting of —OH and AE;

AE is —O($C_1$-$C_3$ alkyl);

provided that at least one R is —OH; and at least one AE is present;

in aqueous alkaline media to an SAE precursor for a period of time sufficient, at a temperature sufficient and at a solution pH sufficient to permit formation of SAE-AE-CD compound; and b) processing the media containing the SAE-AE-CD compound to remove undesired components thereby forming an SAE-AE-CD containing composition.

* * * * *